US010493125B2

(12) United States Patent
Palani et al.

(10) Patent No.: US 10,493,125 B2
(45) Date of Patent: Dec. 3, 2019

(54) CO-AGONISTS OF THE GLUCAGON AND GLP-1 RECEPTORS

(71) Applicants: Merck Sharp & Dohme Corp., Rahway, NJ (US); Anandan Palani, Bridgewater, NJ (US); Paul E. Carrington, San Mateo, CA (US); Antonello Pessi, Rome (IT); Armin Lahm, Rome (IT); Elisabetta Bianchi, Pomezia (IT); Anna Demartis, Pomezia (IT)

(72) Inventors: Anandan Palani, Bridgewater, NJ (US); Paul E. Carrington, San Mateo, CA (US); Antonello Pessi, Rome (IT); Armin Lahm, Rome (IT); Elisabetta Bianchi, Pomezia (IT); Anna Demartis, Pomezia (IT)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/774,622

(22) PCT Filed: Dec. 5, 2016

(86) PCT No.: PCT/US2016/064882
§ 371 (c)(1),
(2) Date: May 9, 2018

(87) PCT Pub. No.: WO2017/100107
PCT Pub. Date: Jun. 15, 2017

(65) Prior Publication Data
US 2018/0339017 A1 Nov. 29, 2018

Related U.S. Application Data

(60) Provisional application No. 62/264,928, filed on Dec. 9, 2015.

(51) Int. Cl.
*A61K 38/16* (2006.01)
*C07K 14/575* (2006.01)
*A61P 1/16* (2006.01)
*A61P 3/10* (2006.01)
*A61K 38/00* (2006.01)

(52) U.S. Cl.
CPC ............ *A61K 38/16* (2013.01); *A61P 1/16* (2018.01); *A61P 3/10* (2018.01); *C07K 14/575* (2013.01); *A61K 38/00* (2013.01)

(58) Field of Classification Search
CPC . A61K 38/00; A61K 38/16; A61P 1/16; A61P 3/10; C07K 14/575
See application file for complete search history.

(56) References Cited

U.S. PATENT DOCUMENTS

| 6,852,690 | B1 | 2/2005 | Nauck et al. |
| 8,703,701 | B2 | 4/2014 | Dimarchi et al. |
| 9,593,155 | B2 * | 3/2017 | Carrington ........... C07K 14/605 |
| 2011/0190200 | A1 | 8/2011 | Dimarchi et al. |
| 2015/0307580 | A1 | 10/2015 | Carrington et al. |

FOREIGN PATENT DOCUMENTS

| WO | WO2003022304 | | 3/2003 |
| WO | WO2004062685 | | 7/2004 |
| WO | WO2006134340 | | 12/2006 |
| WO | WO2007100535 | A2 | 9/2007 |
| WO | WO2008101017 | | 8/2008 |
| WO | WO2009155258 | | 12/2009 |
| WO | WO2010096052 | | 8/2010 |
| WO | WO2010096142 | | 8/2010 |
| WO | 2010148089 | A1 | 12/2010 |
| WO | WO2011075393 | | 6/2011 |
| WO | WO2011143208 | A1 | 11/2011 |
| WO | WO2012177443 | | 12/2012 |
| WO | WO2012177444 | | 12/2012 |
| WO | WO2017100107 | A2 | 6/2017 |

OTHER PUBLICATIONS

Baggio et al., Oxyntomodulin and Glucagon-Like Peptide-1 Differentially, Gastroenterol., 2004, pp. 546-558, 127.
Bhat, Vikas, K. et al., A novel GIP-oxyntomodulin hybrid peptide acting through GIP, Glucagon and GLP-1 receptors exhibits weight reducing and anti-diabetic properties, Biochemical Pharmacology, 2013, p. 1655-1662, vol. 35.
Bikkavilli, Rama, Kamesh, et al., Identification and characterization of surrogate peptide ligand for orphan G protein-coupled receptor mas using phage-displated peptide library, Biochemical Pharmacology, 2006, p. 319-337, vol. 71.
Binetruy-Tournaire, Roselyne, et al., Identification of a peptide blocking vascular endothelial growth factor (VEGF)-mediated angiogenesis, The EMBO Journal, 2000, p. 1525-1533, vol. 19, No. 7.
Chaudhri, Owais, B. et al., Differential hypothalamic neuronal activation following peripheral injection of GLP-1 and oxyntomodulin in mice detected by managanese-enhanced magnetic resonance imaging, Biochemical and Biophysical Research Communications, 2006, p. 298-306, vol. 350.
Chen, Jiaqi, et al., Identifying glucagon-like peptide-1 mimetics using a novel funtional reporter gene high-throughput screening assay, Peptides, 2007, p. 928-934, vol. 28.
Clemmensen, Christoffer, et al., GLP-1/Glucagon Coagonism Restores Leptin Responsiveness in Obese Mice Chronically Maintained on an Obesogenic Diet, Diabetes, 2014, p. 1422-1427, vol. 63.
Chen et al., Oxyntomodulin Suppresses Appetite and Reduces Food intake in Humans, J. Clin. Endocrinol. Metab., 2003, pp. 4696-4701, 88.
Cortese, Riccardo, et al., Identification of biologically active peptides using random libraries displated on phage, Current Opinion in Biotechnology, 1995, p. 73-80, vol. 6.

(Continued)

*Primary Examiner* — Marcela M Cordero Garcia
(74) *Attorney, Agent, or Firm* — Baerbel R. Brown; Catherine D. Fitch

(57) ABSTRACT

Co-agonists of the glucagon and GLP-1 receptors are described.

20 Claims, 3 Drawing Sheets

Specification includes a Sequence Listing.

(56) References Cited

OTHER PUBLICATIONS

Dakin et al., Oxyntomodulin Inhibits Food Intake in the Rat, Endocrinology, 2001, pp. 4244-4250, 142.

Dakin et al., Peripheral Oxyntomodulin Reduces Food Intake and Body Weight Gain in Rats, Endocrinology, 2004, pp. 2687-2695, 145.

Dakin et al., Repeated ICV administration of oxyntomodulin causes a greater reduction in body weight gain than in pair-fed rats, Am. J. Physiol. Endocrinol. Metab., 2002, pp. E1173-E1177, 283.

Dalboge, Lousie, S. et al., The Novel GLP-1-Gastrin Dual Agonist ZP3022 Imprives Glucose Homeostasis and Increases B-Cell Mass without Affecting Islet Number in db/db Mice, The Journal of Pharmacology and Experimental Therapeutics, 2014, p. 353-360, vol. 350.

Day, Jonathan W., A New Glucagon and GLP 1 co agonist eliminates obesity in rodents, Nature Chemical Biology, 2009, No. 10 pp. 749-757, 5.

Day, Jonathan, W. et al., Optimization of Co-Agonism at GLP-1 and Glucagon Receptors to Safely Maximize Weight Reduction in DIO-Rodents, Biopolymers (Pept Sci), 2012, p. 443-450, vol. 98.

Drucker et al., Biologic actions and therapeutic potential of the proglucagon-derived peptides, J. Nat. Clin. Pract. Endocrinol. Metab., 2005, pp. 22-31, 1.

Finan, Brian, et al., A rationally designed monomeric peptide triagonist corrects obesity and diabetes in rodents, Nature Medicine, 2015, p. 27-39, vol. 21, No. 1.

Finan, Brian, et al., Unimolecular Dual Incretins Maximize Metabolic Benefits in Rodents, Monkeys, and Humans, Science Translational Medicine, 2013, p. 1-18, vol. 5, Issue 209.

Fosgerau, K. et al., The novel GLP-1-Gastrin dual agonist, ZP3022, increases B-cell mass and prevents diabetes in db/db mice, Diabetes, Obesity and Metabolism, 2013, p. 62-71, vol. 15.

Gao, Zhihui, et al., A novel DPP-IV-resistant analog of glucagon-like peptide-1 (GLP-1): KGLP-1 Alone or in combination with long-acting PLGA microspheres, Peptides, 2009, p. 1874-1881, vol. 30.

Gault, Victor, A. et al., A Novel Glucagon-like Peptide-1 (GLP-1)/Glucagon Hybrid Peptide with Triple-action Agonist Activity at Glucose-dependent Insulinotropic Polypeptide, GLP-1, and Glucagon Receptors and Therapeutic Potential in High Fat-fed Mice, The Journal of Biological Chemistry, 2013, p. 35581-35591, vol. 288, No. 49.

Habegger et al., The metabolic actions of glucagon revisited, Nat. Rev. Endocrinol., 2010, pp. 689-697, 6.

Hamzeh-Mivehroud, Maryam, et al., Phage display as a technology delivering on the promise of peptide drug discovery, Drug Discovery Today, 2013, p. 1144-1157, vol. 18, No. 23/24.

Harikumar, Kaleeckal, G. et al., Glucagon-like peptide-1 receptor dimerization differentially regulates agonist signaling but does not affect small molecule allostery, PNAS, 2012, p. 18607-18612, vol. 109, No. 45.

Holst, Gut hormones as pharmaceuticals From enteroglucagon to GLP-1 and GLP-2, Regul. Pept., 2000, pp. 45-51, 93.

Holst, J. J. et al., Combining GLP-1 Receptor agonists with insulin: therapeutic rationales and clinical findings, Diabetes, Obesity and Metabolism, 2013, p. 3-14, vol. 15.

International Search Report for PCT/US2016/064882 dated Jul. 7, 2017, 13 pages.

Jarrousse, C. et al., A Pure Enteroglucagon, Oxyntomodulin (Glucagon 37), Stimulates Insulin Release in Perfused Rat Pancreas, Endocrinology, 1984, p. 102-105, vol. 115, No. 1.

Jiang et al., Glucagon and regulation of glucose metabolism, Am. J. Physiol. Endocrinol. Metab., 2003, pp. E671-E678, 284.

Jonas, Kim, C. et al., Single Molecule Analysis of Functionally Asymmetric G Protein-coupled Receptor (GPCR) Oligomers Reveals Diverse Spatial and Structural Assemblies, The Journal of Biological Chemistry, 2015, p. 3875-3892, vol. 290, No. 7.

Jorgensen et al., Oxyntomodulin Differentially Affects Glucagon-Like Peptide-1 Receptor Beta-Arrestin Recruitment and Signaling through G alpha s, J. Pharma. Exp. Therapeut., 2007, pp. 148-154, 322.

Koivunen, Erkki, et al., Selection of Peptides Binding to the a5B1 Integrin from Phage Display Library, The Journal of Biological Chemistry, 1993, p. 20205-20210, vol. 268, No. 27.

Koth, Christopher, M. et al., Molecular basis for negative regulation of the glucagon receptor, PNAS, 2012, p. 14393-14398, vol. 109, No. 36.

Lykkegaard, Kirsten, et al., Central Administration of Oxyntomodulin Inhibits Food Intake without Causing a Conditioned Taste Aversion, Integrated Physiology—Regulation of Food Intake, 2003, p. A348.

O'Neil, Karyn, T. et al., Identification of Novel Peptide Antagonists for GPIIb/IIIa From a Conformationally Constrained Phage Peptide Library, Proteins: Structure, Function, and Genetics, 1992, p. 509-515, vol. 14.

Pan, Clark, Q. et al., Design of a Long Acting Peptide Functioning as Both a Glucagon-like Peptide-1 Receptor Agonist and a Glucagon Receptor Antagonist, The Journal of Biological Chemistry, 2006, p. 12506-12515, vol. 281, No. 18.

Parlevliet, Edwin, T. et al., Oxyntomodulin ameliorates glucose intolerance in mice fed a high-fat diet, Am J Physiol Endocrinol Metab, 2008, p. E142-E147, vol. 294.

Pocai et al., Glucagon-Like Peptide 1/Glucagon Receptor Dual Agonism Reverses Obesity in Mice, Diabetes, 2009, pp. 2258-2266, 58.

Roed, Sarah, Noerklit, et al., Functional Consequences of Glucagon-like Peptide-1 Receptor Cross-talk and Trafficking, the Journal of Biological Chemistry, 2015, p. 1233-1243, vol. 290, No. 2.

Roth, Jonathan, D. et al., Leptin responsiveness restored by amylin agonism in diet-induced obesity: Evidence from nonclinical and clinical studies, PNAS, 2008, p. 7257-7262, vol. 105, No. 20.

Rousch, Mat, et al., Somatostatin displayed on filamentous phage as a receptor-specific agonist, British Journal of Pharmacology, 1998, p. 5-16, vol. 125.

Sadry, Sharon, A., Emerging combinatorial hormone therapies for the treatment of obesity and T2DM, Nature Reviews Endocrinology, 2013, p. 423-433, vol. 9.

Salter, Metabolic Effects of Glucagon in the Wistar Rat, Am. J. Clin. Nutr., 1960, pp. 535-539, 8.

Santoprete, Alessia, et al., DPP-IV-resistant, long-acting oxyntomodulin derivatives, Journal of Peptide Science, 2011, p. 270-280, vol. 17.

Schjoldager et al., Oxyntomodulin: a potential hormone from the distal gut. Pharmacokinetics and effects on gastric acid and insulin secretion in man, Eur. J. Clin. Invest., 1988, pp. 499-503, 18.

Schwyzer, Robert, 100 Years Lock- and Key Concept: Are Peptide Keys Shaped and Guided to Their Receptors by the Target Cell Membrane?, Biopolymers (Peptide Science), 1995, p. 5-16, vol. 37.

Schwyzer, Robert, Estimated Conformation, Orientation, and Accumulation of Dynorphin A-(1-13)-tridecapeptide on the Surface of Neutral Lipid Membranes, Biochemistry, 1986, p. 4281-4286, vol. 25.

Schwyzer, Robert, Membrane-assisted molecular mechanism of neurokinin receptor subtype selection, The EMBO Journal, 1987, p. 2255-2259, vol. 6, No. 8.

Sidhu, Schdev, S. et al., Phage Display for Selection of Novel Binding Peptides, Methods in Enzymology, 2000, p. 333-363, vol. 328.

Siu, et al, Structure of the human glucagon class B G-protein-coupled receptor, Nature, Jul. 2013, 444-451, vol. 499.

Smith, George, P. et al., Phage Display, Chem. Rev, 1997, p. 391-410, vol. 97.

Sowden et al., Oxyntomodulin increases intrinsic heart rate in mice independent of the glucagon-like peptide-1 receptor, Am. J. Physiol. Regul. Integr. Comp. Physiol., 2007, pp. R962-R970, 292.

Szardenings, Michael, et al., Phage Display Selection on Whole Cells Yields a Peptide Specific for Melanocortin Receptor 1, The Journal of Biological Chemistry, 1997, p. 27943-27948, vol. 272, No. 44.

Underwood, Christina, Rye, et al., Crystal Structure of Glucagon-like Peptide-1 in Complex with the Extracellular Domain of the

(56) References Cited

OTHER PUBLICATIONS

Glucagon-like Peptide-1 Receptor, The Journal of Biological Chemistry, 2010, p. 723-730, vol. 285, No. 1.
Wynne et al., Subcutaneous Oxyntomodulin Reduces Body Weight in Overweight and Obese Subjects, Diabetes, 2005, pp. 2390-2395, 54.
Yagodkink, Andrey, et al., Improved Synthesis of Trinucleotide Phosphoramidites and Generation of Randomized Oligonucleotide Libraries, Nucleosides, Nucleotides, and Nucleic Acids, 2007, p. 473-497, vol. 26.
Yin, Xiaopu, et al., Screening of a Phage Display Library of Exendin-4 Mutants with the Extracellular Domain of Rat GLP-1 Receptor, Protein & Peptide Letters, 2007, p. 816-821, vol. 14.
Zhu, Lan, et al., The Role of Dipeptidyl Peptidase IV in the Cleavage of Glucagon Family Peptides, The Journal of Biological Chemistry, 2003, p. 22418-22423, vol. 278, No. 25, Issue of Jun. 20.
Kalra, S., Newer Basal insulin analogues: Degludec, Detemir, Glargine, Pakistan Medical Association, 2013, 1442-1444, vol. 63, No. 11.

\* cited by examiner

```
                  1         10        20     29
Glucagon    HSQGTFTSDYSKYLDSRRAQDFVQWLMNT
Libr 1      XXXXXXXFTSDYSKYLDSRRAQDFVQWLXXT
Libr 2      XXXXXXXSDYSKYLDSRRAQDFVQWLXXT
Libr 3      HSQGTFXXXXXXXLDSRRAQDFVQWLXXT
Libr 4      HSQGTFTSDYSKYXXXXXXXDFVQWLXXT
Libr 5      HSQGTFTSDYSKYLDSRRAQXXXXXXXXX
```

| $X_n$ | Description | Codons |||||||||||||||||||
|---|---|---|---|---|---|---|---|---|---|---|---|---|---|---|---|---|---|---|---|---|
| | | Lys | Asn | Thr | Ile | Met | Gln | His | Pro | Arg | Leu | Glu | Asp | Ala | Gly | Val | Tyr | Ser | Trp | Phe |
| X10 | all 5.26 (no Cys) | AAA | AAT | ACT | ATA | ATG | CAG | CAT | CCG | CGT | CTG | GAA | GAT | GCT | GGT | GTT | TAC | TCT | TGG | TTT |
| X1 | Asp 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X2 | Gln 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X3 | Gly 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X4 | His 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X5 | Lys 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X6 | Phe 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X7 | Ser 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X8 | Thr 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X9 | Tyr 45% other 3% (no Cys) | AAA | AAT | ACT | ATA | ATG | CAG | CAT | CCG | CGT | CTG | GAA | GAT | GCT | GGT | GTT | TAC | TCT | TGG | TTT |
| X11 | Rev: Ala 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X12 | Rev: Arg 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X13 | Rev: Asn 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X14 | Rev: Asp 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X15 | Rev: Gln 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X16 | Rev: Leu 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X17 | Rev: Met 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X18 | Rev: Phe 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X19 | Rev: Ser 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X20 | Rev: Thr 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X21 | Rev: Trp 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |
| X22 | Rev: Val 45% other 3% (no Cys) | TTT | GTT | CGT | AAT | CAT | CTG | ATG | CGG | TCT | CAG | TTC | ATC | TGC | ACC | AAC | ATA | ACT | CCA | AAA |

CO-AGONISTS OF THE GLUCAGON AND GLP-1 RECEPTORS

CROSS-REFERENCE TO RELATED APPLICATIONS

This application is a U.S. National Phase application under 35 U.S.C. § 371 of PCT Application PCT/US16/064882, filed Dec. 5, 2016, which claims priority from and the benefit of US Provisional Application U.S. Provisional Application No. USSN 62/264,928 filed Dec. 9, 2015.

BACKGROUND OF THE INVENTION (1) Field of the Invention

The present invention is related to co-agonist peptides of the glucagon and GLP-1 receptors.

(2) Description of Related Art

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1 (7-36) amide or GLP-1 (7-37) acid are biologically potent forms of GLP-1, that demonstrate essentially equivalent activity at the GLP-1 receptor.

During hypoglycemia, when blood glucose levels drop below normal, glucagon signals the liver to break down glycogen and release glucose, causing blood glucose levels to rise toward a normal level. Hypoglycemia is a common side effect of insulin therapy in patients with hyperglycemia (elevated blood glucose levels) due to diabetes. Thus, glucagon's most recognized role in glucose regulation is to counteract the action of insulin and maintain blood glucose levels.

GLP-1 has different biological activities compared to glucagon. Its actions include stimulation of insulin synthesis and secretion, inhibition of glucagon secretion, and inhibition of food intake. GLP-1 has been shown to reduce hyperglycemia in diabetics. Exendin-4, a peptide from lizard venom that shares about 50% amino acid identity with GLP-1, activates the GLP-1 receptor and likewise has been shown to reduce hyperglycemia in diabetics.

There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

Glucagon is a peptide hormone structurally related to GLP-1 that is well recognized for its acute ability to increase blood glucose through stimulation of glycogenolysis and gluconeogenesis (Jiang & Zhang, Am. J. Physio.l Endocrinol. Metab. 284: E671-E678 (2003)). Of lesser appreciation are the chronic effects of glucagon pharmacology characterized by increases in thermogenesis, satiety, lipolysis, fatty acid oxidation, and ketogenesis (Habegger et al., Nat. Rev. Endocrinol. 6: 689-697 (2010)). Repeated administration of glucagon was first reported decades ago to yield improvements in rodent metabolism, accompanied with lower body weight (Salter, Am. J. Clin. Nutr. 8: 535-539 (1960)). Nonetheless, the inherent risk of hyperglycemia, especially in insulin resistant states such T2DM, has complicated the translation of these observations to human study.

The hormone oxyntomodulin (OXM, glucagon-37) is a posttranslational product of preproglucagon processing in the intestine and central nervous system (CNS) and is secreted from L-cells in the gut in response to food intake. Discovered in 1983, 0) CM has been implicated in the regulation of food intake and energy expenditure (Jarrouse et al., Endocrinol. 115: 102-105 (1984); Schjoldager et al., Eur. J. Clin. Invest., 18: 499-503 (1988)). Central or peripheral administration of OXM in rats causes a decrease in short term food intake with minimal effects on gastric emptying (Dakin et al. Endocrinology, 142: 4244-4250 (2001), Dakin et al. Endocrinology, 145: 2687-2695 (2004)). Repeated intracerebroventricular administration of OXM in rats results in elevated core temperatures and reduced weight gain compared to pair-fed animals, suggesting effects on both caloric intake and energy expenditure (Dakin et al. Am. J. Physiol. Endocrinol. Metab., 283: E1173-E1177 (2002)).

In related studies, peripheral administration of OXM dose-dependently inhibited both fast-induced and dark phase food intake, but unlike GLP-1, had no effect on gastric emptying. OXM also reduced levels of fasting ghrelin and increased c-fos immunoreactivity, in the arcuate nucleus (ARC). Repeated seven-day IP administration of OXM caused a reduction in the rate of body weight gain and adiposity in rats (See Dakin et al. Endocrinology, 145: 2687-2695 (2004)).

Studies of OXM action in mice have demonstrated that although OXM can activate both the glucagon (GCG) and the GLP-1 receptors, the anorectic actions of OXM require only the GLP-1 receptor, as icy OXM inhibits food intake in glucagon receptor knockout mice. However, the anorectic effects of OXM are completely absent in GLP-1 receptor knockout mice. Furthermore, exendin-4, but not OXM, regulates energy expenditure in mice. Hence, OXM appears to be a weak agonist at the GLP-1 receptor, when used in pharmacological concentrations (See Baggio et al., Gastroenterol. 127: 546-58 (2004)). OXM was also found to ameliorate glucose intolerance in mice fed a high fat diet (Dakin et al., Am. J. Physiol. Endocrinol. Metab. 294: E142-E147 (2008) and increase the intrinsic heart rate in mice independent of the GLP-1 receptor (Sowden et al., Am. J. Physiol. Regul. Integr. Comp. Physiol. 292: R962-R970 (2007). OXM has also been shown to differentially affect GLP-1 receptor beta-arrestin recruitment and signaling through Galpha (Jorgensen et al., J. Pharma. Exp. Therapeut. 322: 148-154 (2007)) and to differentially affect hypothalamic neuronal activation following peripheral injection of OXM (Choudhri et al., Biochem. Biophys. Res. Commun. 350: 298-306 (2006)).

In humans, a single 90 minute intravenous infusion of OXM in normal weight healthy subjects reduced hunger scores and food intake at a buffet meal by about 19%. Cumulative twelve-hour caloric intake was reduced by about 11% with no reports of nausea or changes in food palatability (Cohen et al., J. Clin. Endocrinol. Metab., 88: 4696-4701 (2003); Lykkegaard et al., ADA Scientific Sessions, Abstract #1506-P (2003)). More recently, pre-prandial injections of OXM over a four-week period in obese healthy volunteers (BMI about 33) led to a significant reduction of caloric intake on the first day of treatment (about 25%) that was maintained over the course of the study (35% reduction after four weeks) (Wynne et al., Diabetes 54: 2390-2395 (2005)). Robust weight loss was observed at the end of the study in treated subjects (1.9%, placebo-corrected). Plasma levels of OXM were similar to that observed in the infusion study (peak concentration about 950 pM). The absence of any tachyphylaxis and a low incidence of mild and transient nausea (about 3%) despite the relatively high doses necessitated by the poor in vivo stability of OXM (plasma t½<12 minutes) renders this hormone one of the few obesity targets with both human validation and an attractive tolerability profile.

OXM has a very short half-life and is rapidly inactivated by the cell surface dipeptidyl peptidase IV (DPP-IV) (Zhu et al., J. Biol. Chem. 278: 22418-22423 (2002). However, DPP-IV inhibitors are weight-neutral in the clinic, suggesting that supraphysiological levels of OXM (900-1000 pM) may be required to achieve weight loss in humans. OXM peptide analogs for inducing weight loss in humans have been the object of Published International Application Nos. WO03/022304, WO2004/062685, WO2006/134340, and WO2010/096052.

Recently, two independent and simultaneous papers reported the use of relatively balanced GLP-1 receptor/GCG receptor co-agonists as being of enhanced efficacy and safety relative to pure GLP1R agonists in the treatment of rodent obesity, with simultaneous improvement in glycemic control (Day et al., Nat. Chem. Biol. 5: 749-757 (2009); Pocai et al., Diabetes 58: 2258-2266 (2009)). Of related significance is work with oxyntomodulin (OXM), an endogenous precursor to glucagon, which is secreted postprandially by L-cells of the jejuno-ileum together with GLP-1 (Hoist, Regul. Pept. 93: 45-51 (2000); Drucker, Nat. Clin. Pract. Endocrinol. Metab. 1: 22-31 (2005).

Glucagon peptide analogs and derivatives modified to have various degrees of activity at the GLP-1 receptor and GCG receptor have been disclosed in Published International Application Nos. WO2008/1010017, WO2009/155258, WO2011/075393, WO2012/177444, and WO2012/177443. Some of the disclosed glucagon peptide analogs were reported therein to have activity at both the GLP-1 receptor and GCG receptor; however, there remains a need for co-agonist peptides that have activity or potency at the GLP-1 receptor and GCG receptor.

BRIEF SUMMARY OF THE INVENTION

The present invention provides co-agonist peptides of the human glucagon (GCG) receptor and the human glucagon-like protein 1 (GLP-1) receptor that include substitution of one or more amino acids of the native glucagon peptide with an L-amino acid not native to glucagon to produce a non-native glucagon peptide that is a co-agonist at the glucagon and GLP-1 receptors. Native human glucagon has about 10-fold greater activity at the glucagon receptor than at the GLP-1 receptor. Phage display technology was used to construct libraries of randomly mutagenized human glucagon peptides, which were screened for activity at both the human glucagon receptor and the human GLP-1 receptor. The technology has enabled the inventors to discover peptides that have co-agonist activity at the glucagon and GLP-1 receptors. The co-agonist peptides identified by the phage display screens may be stabilized against inactivation in vivo by dipeptidyl peptidase-4 (DPP-IV) cleavage at the N-terminus by replacing the serine residue at position 2 of the co-agonist peptide with an amino acid that inhibits DPP-IV cleavage. For example an amino acid selected from the group consisting of Val, Ile, Asp, Glu, Met, Trp, Asn, D-Ala, D-Ser, and alpha-aminoisobutyric (aib). The co-agonist peptides further include amidation of the C-terminus amino acid to stabilize the co-agonist peptide from potential degradation in vivo by carboxypeptidases.

The co-agonist peptides may have a blood serum half-life of at least one day, two days, three days, four days, five days, six days, or seven days. The co-agonist peptides further comprise modifications that control the relative activity at the GLP-1 receptor versus the glucagon receptor. Thus, yet another aspect of the invention provides co-agonist peptides that have higher activity at the glucagon receptor versus the GLP-1 receptor, co-agonist peptides that have approximately equivalent activity at both receptors, and co-agonist peptides that have higher activity at the GLP-1 receptor versus the glucagon receptor. The latter category of co-agonist peptides may be engineered to exhibit little or no activity at the glucagon receptor, and yet retain ability to activate the GLP-1 receptor with the same or better potency than native GLP-1. Any of these analogs may also include modifications that confer enhanced biophysical stability and/or aqueous solubility. The co-agonist peptides herein are useful for the treatment of metabolic diseases or disorders, such as but not limited to, diabetes (e.g., type 1 diabetes, Type 2 diabetes, or gestational diabetes), non-alcoholic fatty liver disease (NAFLD), non-alcoholic steatohepatitis (NASH), and/or obesity.

The present invention provides a co-agonist peptide comprising a peptide selected from following peptides

| SEQ ID NO: | Name | Sequence |
|---|---|---|
| 1 | PD17 | HSVGNFWSDYSKYLDSRRAQDFVQWLMLT-CONH$_2$ |
| 2 | PD18 | HSQGTFTSDSKYVEDRRAHDFVQWLMNT-CONH$_2$ |
| 3 | PD19 | HSQGTFTSDYRKYLDERAAWDFVQWLMNT-CONH$_2$ |
| 4 | PD20 | HSQGTFTSDYSKYLNSWMTQDFVQWLMNT-CONH$_2$ |
| 5 | PD21 | HSQGTFTSDYSKYLDIGRAQDFVQWLLNT-CONH$_2$ |
| 6 | PD22 | HSQGTFTSDYSKYLDSLMAQDFVQWLMST-CONH$_2$ |
| 7 | PD23 | HSQGTFTSDYSKYLDWRRAQDFVQWLLNT-CONH$_2$ |
| 8 | PD24 | HSQGTFTSDYIKLLDSRRAQDFVQWLMNT-CONH$_2$ |
| 9 | PD25 | HSQGTFTSDYSKYLDARRAQDFVQWLIRT-CONH$_2$ |
| 10 | PD26 | HSQGTFTSDYSKYLDVRRAQDFVQWLMNT-CONH$_2$ |
| 11 | PD27 | HSQGTFTSDYSKYLDELRAYDFVQWLMNT-CONH$_2$ |
| 12 | PD28 | HSQGTFTSDYSKYLDYMRAYDFVQWLMNT-CONH$_2$ |
| 13 | PD29 | HSQGTFTSDYSKYLDSRRAHDFVQWLLNT-CONH$_2$ |
| 14 | PD30 | HSQGTFTSDYSKYLDSRRAQDFVQWLMNP-CONH$_2$ |
| 15 | PD31 | HSQGTFTSDYSKYLDSRRAQDFVQWLINY-CONH$_2$ |
| 16 | PD32 | INHEQWAFTSDYSKYLDSRRAQDFVQWLMNT-CONH$_2$ |
| 17 | PD33 | ASMFTFFSDYSKYLDSRRAQDFVQWLMLT-CONH$_2$ |
| 18 | PD34 | HSQGTFLSDYSKLLDSRRAQDFVQWLMQT-CONH$_2$ |
| 19 | PD35 | HSQGTFLHDYYYYLDSRRAQDFVQWLMDT-CONH$_2$ |
| 20 | PD36 | HSQGTFTSDYSKYLDSIRAQDFVQWLMDT-CONH$_2$ |
| 21 | PD37 | HSQGTFTSDYSKYLDNKRAQDFVQWLMQT-CONH$_2$ |
| 22 | PD38 | HSQGTFTSDYSKYLDSRRAQDFVDWLMNE-CONH$_2$ |

| SEQ ID NO: | Name | Sequence |
|---|---|---|
| 23 | PD39 | HSQGTFTSDYSKYLDSRRAQEFVEWLMDE-CONH₂ |
| 24 | PD40 | HSQGTFTSDYSKYLDSRRAQDFVQWLINT-CONH₂ |
| 25 | PD41 | KALGQFTFTSDYSKYLDSRRAQDFVQWLMNT-CONH₂ |
| 26 | PD42 | HSQGTFFHDYSKYLDSRRAQDFVQWLLNT-CONH₂ |
| 27 | PD43 | HSQGTFFSDYSHWLDSRRAQDFVQWLMNT-CONH₂ |
| 28 | PD44 | HSQGTFTSDYSKYLDWRRAQDFVQWLQNT-CONH₂ |
| 29 | PD45 | HSQGTFTSDYSKYLDSKRAHDFVQWLLNT-CONH₂ |
| 30 | PD46 | HSQGTFTSDYSKYLDSRRAQDFWIDLMNT-CONH₂ |
| 31 | PD47 | HSQGTFTSDYSKYLDSRRAQDFVMTSMNT-CONH₂ |
| 32 | PD48 | HSQGTFTSDYSKYLDSRRAQDFVDWLLNA-CONH₂ |
| 33 | PD49 | HSQGTFTSDYSKYLDSRRAQDFVEWLMNN-CONH₂ |
| 34 | PD50 | HSQGTFTSDYSKYLDSRRAQDFVDWLINS-CONH₂ |
| 35 | PD51 | HSHGTFTSDYSKYLDSRRAQDFVQWLMTT-CONH₂ |
| 36 | PD52 | HSQGIFFSDYSKYLDSRRAQDFVQWLMNT-CONH₂ |
| 37 | PD53 | HSQGTFLSDYSKYLDSRRAQDFVQWLMNT-CONH₂ |
| 38 | PD54 | HSQGTFTSDYSWYLDSRRAQDFVQWLMNT-CONH₂ |
| 39 | PD55 | HSQGTFTSDYSKYLDMQRAHDFVQWLMNT-CONH₂ |
| 40 | PD56 | HSQGTFTSDYSKYLDSRMAYDFVQWLMNT-CONH₂ |
| 41 | PD57 | HSQGTFTSDYSKYLDSRRAQDFVQWLLNQ-CONH₂ |
| 42 | PD58 | HSQGTFFSDYSKYLDSRRAQDFVQWLLET-CONH₂ |
| 43 | PD59 | HSQGTFTSDYSKYLDSRRAQDFVQWLLDS-CONH₂ | wherein the L-Serine at position 2 is replaced with Val, Ile, Asp, Glu, Met, Trp, Asn, D-Ala, D-Ser, or α-aminoisobutyric acid (aib), the Tyrosine at position 10 is replaced with a Lysine residue conjugated to a fatty acid or fatty diacid via a linking moiety, wherein CONH₂ indicates the C-terminal amino acid carboxy group is amidated, and the peptide may comprise 0, 1, 2, 3, 4, 5, 6, 7, 8, 9, or 10 additional amino acid substitutions.

In particular embodiments, the co-agonist peptide of claim 1, wherein the fatty acid or fatty diacid comprises 14 to 20 methylene groups. In a further embodiment, the fatty acid or fatty diacid comprises 16 carbon atoms.

In particular embodiments, the linking moiety comprises a PEG₂ (8-amino-3,6-dioxaoctanoic acid) Gamma-Glutamic acid (γGlu), a γGlu, a γGluγGlu, or a PEG₂PEG₂ γGlu.

The present invention further provides a co-agonist peptide comprising a peptide selected from the following peptides

| SEQ ID NO: | Name | Sequence |
|---|---|---|
| 44 | TP534 | HsQGTFTSDK(γEγEC16) SKYLDNKRAQDFVQWLMQT-CONH₂ |
| 45 | TP535 | HsQGTFTSDK(γEγEC16) SKYLDSRRAHDFVQWLLNT-CONH₂ |
| 46 | TP536 | HsQGTFLSDK(γEγEC16) SKLLDSRRAQDFVQWLMQT-CONH₂ |
| 47 | TP552 | HsQGTFLSDYSKLLDSRAAQDFVQWLLQT-CONH₂ |
| 48 | TP559 | HsQGTFTSDK(γEγEC16) SKYLDARAAHDFVQWLLNT-CONH₂ |
| 49 | TP572 | HUQGTFTSDK(γEγEC16) SKYLDSRRAHDFVQWLLNTKγE-CONH₂ |
| 50 | TP573 | HUQGTFTSDK(γEγEC16) SKYLDARAAHDFVQWLLNTKγE-CONH₂ |
| 51 | TP574 | HUQGTFTSDK(γEγEC16) SKYLDNKRAQDFVQWLMQTKγE-CONH₂ | wherein U is aminoisobutyric acid, s is D-Ser, γE=γ-glutamic acid, and C16=—CO—(CH₂)₁₄—CH₃ and wherein CONH₂ indicates the C-terminal amino acid carboxy group is amidated.

In particular embodiments, the present invention provides a composition comprising one or more co-agonist peptides of claims 1-6 and a pharmaceutically acceptable carrier and/or pharmaceutically acceptable salt.

The present invention further provides a method for treating a patient for a metabolic disease or disorder comprising administering the patient an effective amount of any one or more of the co-agonist peptides of claims 1-6 to treat the metabolic disease or disorder in the patient.

In particular aspects, the metabolic disease or disorder comprises diabetes, non-alcoholic fatty liver disease (NAFLD), non-alcoholic steatohepatitis (NASH), or obesity. In particular aspects, the diabetes comprises Type I diabetes, Type II diabetes, or gestational diabetes. In a further aspect, the patient has more than one metabolic disease or disorder, which may be for example, a metabolic disease or disorder which comprises, diabetes and NASH, NAFLD, or obesity; obesity and NASH or NAFLD; diabetes, NASH, and obesity; diabetes, NAFLD, and obesity; or diabetes and obesity.

The present invention further provides a method for treating a patient for a metabolic disease or disorder comprising administering the patient an effective amount of the composition of claim 6 to treat the metabolic disease or disorder in the patient.

In particular aspects, the metabolic disease or disorder comprises diabetes, non-alcoholic fatty liver disease (NAFLD), non-alcoholic steatohepatitis (NASH), or obesity. In particular aspects, the diabetes comprises Type I diabetes, Type II diabetes, or gestational diabetes. In a further aspect, the patient has more than one metabolic disease or disorder, which may be for example, a metabolic disease or disorder which comprises, diabetes and NASH, NAFLD, or obesity; obesity and NASH or NAFLD; diabetes, NASH, and obesity; diabetes, NAFLD, and obesity; or diabetes and obesity.

The present invention further provides for the use of one or more co-agonist peptides of claims 1-6 for manufacture of a medicament for the treatment of a metabolic disease or disorder.

In particular aspects, the metabolic disease or disorder comprises diabetes, non-alcoholic fatty liver disease (NA- FLD), non-alcoholic steatohepatitis (NASH), or obesity. In particular aspects, the diabetes comprises Type I diabetes, Type II diabetes, or gestational diabetes. In a further aspect, the use may be for treatment of more than one metabolic disease or disorder, which may be for example, a metabolic disease or disorder which comprises, diabetes and NASH, NAFLD, or obesity; obesity and NASH or NAFLD; diabetes, NASH, and obesity; diabetes, NAFLD, and obesity; or diabetes and obesity.

The present invention further provides a method for treating a metabolic disease or disorder in a patient or individual comprising: administering to the patient or individual an effective amount of any one of the aforementioned compositions comprising a co-agonist peptide agonist and administering to the patient or individual an effective amount of a composition comprising an insulin or insulin analog to treat the metabolic disease or disorder in the patient or individual.

In particular aspects, the insulin analog comprises insulin detemir, insulin glargine, insulin levemir, insulin glulisine, insulin degludec, or insulin lispro.

In particular aspects, the metabolic disease or disorder comprises diabetes, non-alcoholic fatty liver disease (NAFLD), non-alcoholic steatohepatitis (NASH), or obesity. In particular aspects, the diabetes comprises Type I diabetes, Type II diabetes, or gestational diabetes. In a further aspect, the patient has more than one metabolic disease or disorder, which may be for example, a metabolic disease or disorder which comprises, diabetes and NASH, NAFLD, or obesity; obesity and NASH or NAFLD; diabetes, NASH, and obesity; diabetes, NAFLD, and obesity; or diabetes and obesity.

The present invention further provides a composition comprising one or more of any one of the aforementioned co-agonist peptides and a pharmaceutically acceptable carrier and/or pharmaceutically acceptable salt.

The present invention further provides a method for treating a patient for a metabolic disease or disorder comprising administering the patient an effective amount of any one or more of the aforementioned co-agonist peptides to treat the metabolic disease or disorder in the patient.

The present invention further provides method for treating a patient for a metabolic disease or disorder comprising administering the patient an effective amount of a composition comprising any one or more of the co-agonist peptides to treat the metabolic disease or disorder in the patient.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned co-agonist peptides for manufacture of a medicament for the treatment of a metabolic disease or disorder.

The present invention further provides for the use of any one of the aforementioned co-agonist peptides or compositions for manufacture of a medicament for the treatment of a metabolic disease or disorder.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the medicament is for treatment of more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

Further provided is method for treating a metabolic disease or disorder in a patient or individual comprising: administering to the patient or individual an effective amount of any one of the aforementioned compositions comprising a co-agonist peptide agonist and administering to the patient or individual an effective amount of a composition comprising an insulin or insulin analog to treat the metabolic disease or disorder in the patient or individual.

In particular aspects, the composition comprising the co-agonist peptide is administered at a time prior to the time the composition comprising the insulin or insulin analog is administered. In another aspect, the composition comprising the insulin or insulin analog is administered at a time prior to the time the composition comprising the co-agonist peptide is administered. In a further still aspect, the composition comprising the co-agonist peptide is administered at the same time as the composition comprising the insulin or insulin analog is administered.

In particular aspects, the insulin analog is insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides a composition comprising any one of the aforementioned co-agonist peptides; an insulin or insulin analog; and, a pharmaceutically acceptable carrier. In particular aspects, the insulin analog is insulin detemir, insulin glargine (U100 or U300), insulin levemir, insulin glulisine, insulin degludec, or insulin lispro.

The present invention further provides for the use of a composition comprising any one of the aforementioned co-agonist peptides; an insulin or insulin analog; and, a pharmaceutically acceptable carrier for the treatment of a metabolic disease or disorder. In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes. The present invention further provides for the use of a composition comprising any one of the aforementioned co-agonist peptides; an insulin or insulin analog; and, a pharmaceutically acceptable carrier for the manufacture of a medicament for the treatment of a metabolic disease or disorder. In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

In particular aspects, the insulin analog is insulin detemir, insulin glargine (U100 or U300), insulin levemir, insulin glulisine, insulin degludec, or insulin lispro.

Definitions

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a glucagon peptide refers to a nontoxic but sufficient amount of the peptide to provide the desired effect. For example one desired effect would be the prevention or treatment of hyperglycemia, e.g., as measured by a change in blood glucose level closer to normal, or inducing weight loss/preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route, e.g., subcutaneous, intramuscular, intraspinal, or intravenous.

As used herein, the term "peptide" encompasses a chain of 3 or more amino acids and typically less than 100 amino acids, wherein the amino acids are naturally occurring or coded or non-naturally occurring or non-coded amino acids. Non-naturally occurring amino acids refer to amino acids that do not naturally occur in vivo but which, nevertheless, can be incorporated into the peptide structures described herein. "Non-coded" as used herein refers to an amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. "Coded" as used herein refers to an amino acid that is an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. In some embodiments, the peptides and variant peptides described herein are about the same length as SEQ ID NO: 1 (which is 29 amino acids in length), e.g. 25-35 amino acids in length. Exemplary lengths include 29, 30, 31, 32, 33, 34, 35, 36, 37, 38, 39, 40, 41, 42, 43, 44, 45, 46, 47, 48, 49, or 50 amino acids in length. The term further includes peptides wherein one or more amino acids is conjugated to a second molecule via a linker.

Typically, polypeptides and proteins have a polymer length that is greater than that of "peptides."

Amino acid "modification" refers to an insertion, deletion or substitution of one amino acid with another. In some embodiments, the amino acid substitution or replacement is a conservative amino acid substitution, e.g., a conservative substitution of the amino acid at one or more of positions 2, 5, 7, 10, 11, 12, 13, 14, 16, 17, 18, 19, 20, 21, 24, 27, 28 or 29. As used herein, the term "conservative amino acid substitution" is the replacement of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues: Ala, Ser, Thr, Pro, Gly;
II. Polar, negative-charged residues and their amides and esters:
Asp, Asn, Glu, Gln, cysteic acid and homocysteic acid;
III. Polar, positive-charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine In some embodiments, the amino acid substitution is not a conservative amino acid substitution, e.g., is a non-conservative amino acid substitution.

As used herein the term "charged amino acid" or "charged residue" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an $EC_{50}$ of 1 nM at a first receptor and an $EC_{50}$ of 100 nM at a second receptor has 100-fold selectivity for the first receptor relative to the second receptor.

As used herein, "glucagon potency" or "potency compared to native glucagon" of a molecule refers to the inverse ratio of the $EC_{50}$ of the molecule at the glucagon receptor divided by the $EC_{50}$ of native glucagon at glucagon receptor.

As used herein, "GLP-1 potency" or "potency compared to native GLP-1" of a molecule refers to the inverse ratio of the $EC_{50}$ of the molecule at GLP-1 receptor divided by the $EC_{50}$ of native GLP-1 at GLP-1 receptor.

BRIEF DESCRIPTION OF THE DRAWINGS

FIG. 1: Phage display library used to select GCGR/GLP1R co-agonists is composed of five sub-libraries, each one with nine randomized positions. For selection on GCGR+ and GLP1R+ cells, the five libraries were pulled and selected together. X=any amino acid with the proviso that for each library X is not Cys and at least one X in each series of Xs in the library is not a wild-type amino acid. Glucagon=SEQ ID NO:52; Libr 1=SEQ ID NO:53; Libr 2=SEQ ID NO:54; Libr 3=SEQ ID NO:55; Libr 4=SEQ ID NO:56; and Libr 5=SEQ ID NO:57.

FIG. 3 is a table showing the composition for each of the codon mixes.

DETAILED DESCRIPTION OF THE INVENTION

Figure 2:
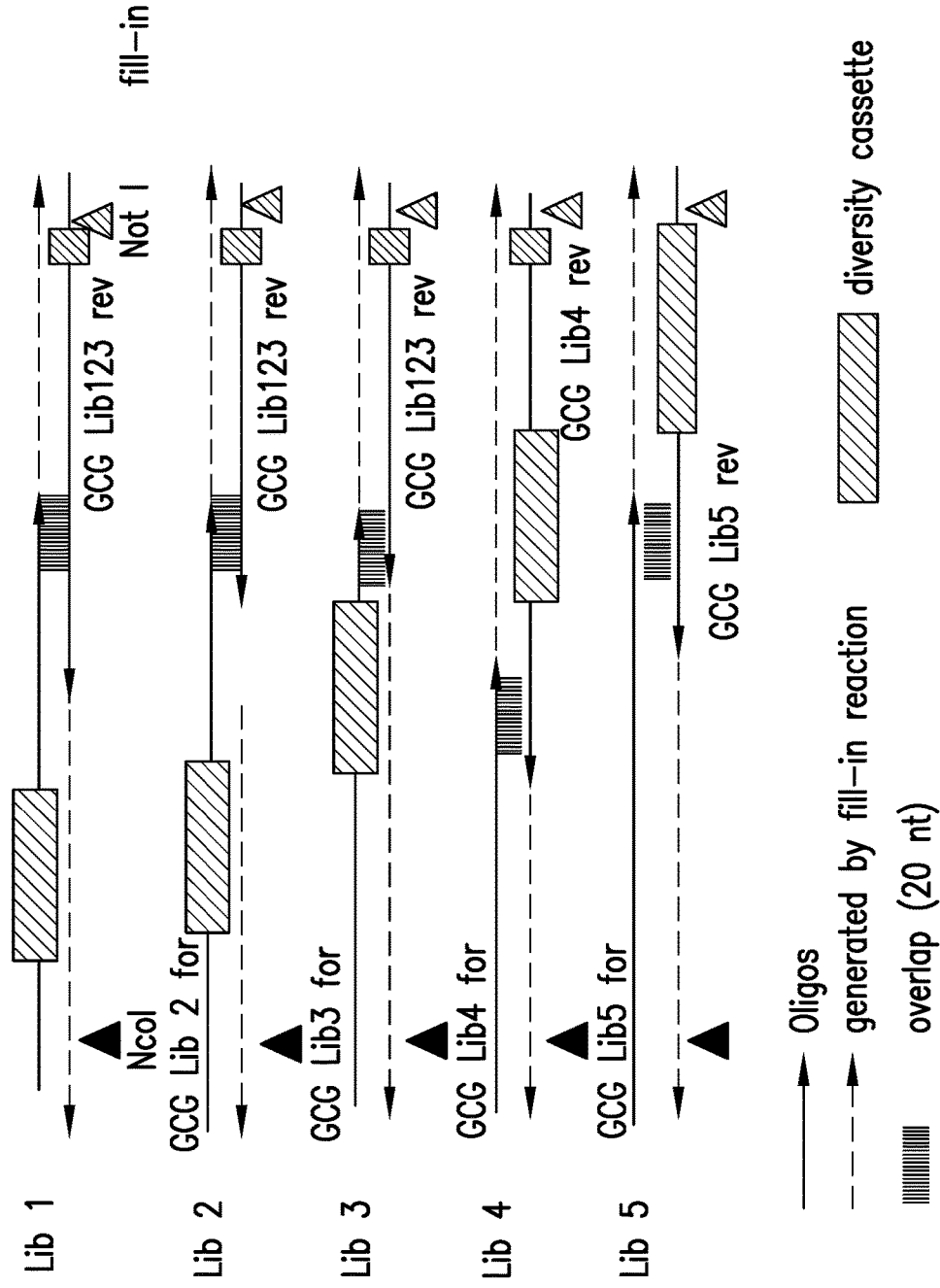
FIG. 2: The single-strand oligonucleotides were converted into double-strand nucleotide fragments by primer extension, combining the relative oligonucleotide forward and reverse for each library.

The present invention provides peptide co-agonists of the glucagon (GCG) receptor and the glucagon-like protein 1 (GLP-1) receptor. The co-agonists comprise the amino acid sequence of glucagon peptide wherein specific mutations have been introduced which result in peptides that have co-agonist activity. The co-agonist peptides further comprise modifications that control the relative activity at the GLP-1 receptor verses the glucagon receptor. Thus, yet another aspect of the invention provides co-agonist peptides that have higher activity at the glucagon receptor versus the GLP-1 receptor, co-agonist peptides that have approximately equivalent activity at both receptors, and co-agonist peptides that have higher activity at the GLP-1 receptor versus the glucagon receptor. The latter category of co-agonist peptides may be engineered to exhibit little or no activity at the glucagon receptor, and yet retain ability to activate the GLP-1 receptor with the same or better potency than native GLP-1. Any of these analogs may also include modifications that confer enhanced biophysical stability and/or aqueous solubility. The co-agonist peptides herein are useful for the treatment of metabolic disorders, such as but not limited to, diabetes (e.g., type 1 diabetes, Type 2 diabetes, or gestational diabetes), non-alcoholic fatty liver disease (NAFLD), non-alcoholic steatohepatitis (NASH), and/or obesity.

One of the most promising emerging areas for the treatment of obesity and Diabetes is combinatorial hormone therapies [1-3]. In particular, single molecule peptides have been discovered integrating the complementary actions of multiple endogenous metabolically-related hormones [4-14].

Collectively, these studies had proven that the high evolutionary relatedness of peptides like glucagon (GCG), GLP-1, and GIP and their cognate receptors enables using the sequence of one these hormones as a starting point, onto which co-agonism for one or more additional hormone receptors can be installed, with relatively few sequence changes [7-8, 10-11]. Sometimes, as little as one amino acid change is sufficient to switch between single- and dual-hormone agonism [9, 15].

These studies have been carried out by "rational design", through an iterative cycle combining hybridization of the parent peptides with single-point mutations guided by the developing SAR: while successful and a testimony to the ingenuity of peptide medicinal chemists, this has necessarily limited the exploration of the chemical space to the immediate vicinity of the parent sequences. For example, the effect of multiple mutations in different parts of the molecule has rarely been explored, precluding a thorough investigation of conformational cross-talk.

One alternative way to develop unimolecular polypharmacy agents is the use of selection methods, for example those based on phage-displayed peptide libraries [16-19]. The defining feature of the libraries is the existence of a physical linkage between the peptide displayed on the surface (which determines the phenotype) and its encoding DNA (the genotype). Very large, diverse, random libraries can be constructed and selected, and the results of the screening can be rapidly decoded by DNA sequencing.

Peptide agonists and antagonists of cell membrane receptors have been successfully identified using this process [19-22], including peptide agonists of G-protein-coupled receptors (GPCRs) [23-28].

In 1997-98 Szardenings et al. [23] and Rousch et al. [24] first showed that phages bearing a GPCR agonist, the peptide hormones α-MSH or somatostatin, fused to the pIII or the pVIII protein could bind to cells expressing the respective receptor and most importantly, could activate it, acting as an agonist with lower [23] or even comparable [24] potency to the free peptide.

For the class B GPCRs, Yin et al. screened a library of Exendin-4 mutants (2-3 average mutations/molecule) on the N-terminal region including the ectodomain (aa 21-145) of rat GLP1R [26]. Sequencing of 60 clones from the third biopanning led to the identification of a phage which bound the receptor fragment better than the WT peptide; the mutant phage featured the Glu$^{16}$Val, Pro$^{31}$Gln, and Ser$^{33}$Asn mutations.

Koth et al. selected a library of glucagon mutants on the ectodomain of the GCG receptor (GCGR), immobilized on a plate through a biotin tag [28]. In the library, residues 16-29 were "soft randomized" to be a mixture of 50% WT and 50% random amino acid. In the terminology first proposed by Schwyzer [29-31], this corresponds to the "address" segment of GCG, mostly responsible for receptor selectivity, while the N-terminal region represents the "message" segment, mostly responsible for receptor activation. Structural and modeling studies indicate that the "address" includes the key molecular determinants for binding to the receptor ectodomain, while the "message" is in contact with the 7TM membrane-embedded domain [28, 32-33].

Chen et al. selected a 12-amino acid random library on stable recombinant cells overexpressing the rat GLP1 receptor (GLP1R) [27]. Four rounds of selection enriched for GLP1R cell-binding phages. About 1% of the specifically bound phages (10 phages) were capable of activating the GLP1R, with the best peptide, KS-12, featuring high sequence homology to the N-terminal "message" region of GPL-1 [27]. KS-12 showed EC$_{50}$ of 0.8 μM, vs 0.8 nM of GLP-1 in the same assay.

Collectively, these studies established that (i) a peptide hormone—including GLP-1—on the surface of a phage particle is capable of activating its receptor expressed on the cell surface; (ii) it is possible to identify active mutants both in the "message" and the "address" segments of the peptide ligands of class B GPCRs.

The above studies were aimed at evolving a single receptor-specific peptide, however, inventors have developed a selection strategy for identifying peptides able to activate more than one receptor. As shown herein, the selection of GCG/GLP-1 receptor co-agonists from a phage display library based on randomization of the glucagon sequence, sequentially selected on GCGR- and GLP1R-overexpressing cells. Two or three rounds of selection enabled the discovery of novel unimolecular co-agonists, with comparable in vitro potency to the reported designed peptides [7, 10].

Library design. In order to independently interrogate the "message" and the "address" segments of GCG the library design was split into four sub-libraries, each focusing on one of four seven-amino acid long consecutive segments (FIG. 1).

The two C-terminal residues 27 and 28, together with the N-terminal residues, exhibit more diversity among GCG, GLP-1 and GIP and are critical for the interaction of each hormone with the respective receptor [11]. These residues were mutagenized in all four sub-libraries.

Additionally, motivated by the results of Chen et al. showing that an additional N-terminal Lys residue was well tolerated for GLP1R agonism and offered increased resistance to DPP-IV [27, 35], the inventors designed a fifth library exploring variants harboring a two amino acid extension at the GCG N-terminus.

Both GCG and GLP-1 are low picomolar ligands of the respective receptors, suggesting that their sequence is highly optimized; moreover, the work of Tschop and co-coworkers had shown that relatively few mutations suffice to install dual- or even triple-agonism in the GCG sequence [7-8, 10-11]. Therefore in all the sub-libraries, instead of a standard full-randomization scheme (equal ratios of all amino acids except Cys) which would have predominantly provided variants with ≥4 mutations, the inventors chose a randomization scheme where each mutagenized position retained a constant fraction of 45% wt residue: for a library with a targeted complexity 6×10$^7$, this scheme produced variants with a small number (1-3) of mutations (Table 1).

TABLE 1

Distribution of the variants in a library of complexity 6 × 10$^7$ with 45% wild-type amino acid at each of the nine randomized positions.

| No. of Mutations In GCG | Fraction | Cumulative Fraction | No. of physical clones | Theoretical Diversity | Poisson estimate Coverage | Number of unique clones * | Average # of duplicates |
|---|---|---|---|---|---|---|---|
| 0 (wt) | 0.08% | 0.08% | 4.54 × 10$^4$ | 1.00 | 100.00% | 1.00 | 45400.84 |
| 1 | 0.83% | 0.91% | 4.99 × 10$^5$ | 1.62 × 10$^2$ | 100.00% | 1.62 × 10$^2$ | 3082.77 |
| 2 | 4.07% | 4.98% | 2.44 × 10$^6$ | 1.17 × 10$^4$ | 100.00% | 1.17 × 10$^4$ | 209.32 |
| 3 | 11.60% | 16.58% | 6.96 × 10$^6$ | 4.90 × 10$^5$ | 100.00% | 4.90 × 10$^5$ | 14.21 |
| 4 | 21.28% | 37.86% | 1.28 × 10$^7$ | 1.32 × 10$^7$ | 61.91% | 8.19 × 10$^6$ | 1.56 |
| 5 | 26.00% | 63.86% | 1.56 × 10$^7$ | 2.38 × 10$^8$ | 6.34% | 1.51 × 10$^7$ | 1.03 |
| 6 | 21.19% | 85.05% | 1.27 × 10$^7$ | 2.86 × 10$^9$ | 0.44% | 1.27 × 10$^7$ | <<1 |
| 7 | 11.10% | 96.15% | 6.66 × 10$^6$ | 2.20 × 10$^{10}$ | 0.03% | 6.66 × 10$^6$ | <<1 |
| 8 | 3.39% | 99.54% | 2.03 × 10$^6$ | 9.92 × 10$^{10}$ | 0.00% | 2.03 × 10$^6$ | <<1 |
| 9 | 0.46% | 100.00% | 2.76 × 10$^5$ | 1.98 × 10$^{11}$ | 0.00% | 2.76 × 10$^5$ | <<1 |
| Sum: | 100% | | 6.00 × 10$^7$ | | | 4.55 × 10$^7$ | |

* Based on Poisson estimate for coverage of theoretical diversity (fractional completeness)

Exemplary co-agonist peptides identified using phage display are shown in Table 2. The peptides are shown in alignment with GCG and GLP1. The EC50 in nm of the peptides at the human GCG and GLP1 receptors are shown.

TABLE 2

| SEQ ID No. | PD-# | Sequence | EC$_{50}$ hGCGR (nm) | EC$_{50}$ hGLP1R (nm) |
|---|---|---|---|---|
| 52 | GLP-1 | HAEGTFT SDVSSY LEGQAAK EFIAWLVKGRG-CONH$_2$ | NA | 0.008 |
| 53 | GCG | HSQGTFT SDYSKY LDSRRAQ DFVQWLMNT | 0.005 | 0.06 |
| 6 | PD22 | HSQGTFT SDYSKY LDSLMAQ DFVQWLMST-CONH$_2$ | 0.02 | 0.03 |
| 7 | PD23 | HSQGTFT SDYSKY LDWRRAQ DFVQWLLNT-CONH$_2$ | 0.03 | 0.05 |
| 9 | PD25 | HSQGTFT SDYSKY LDARRAQ DFVQWLIRT-CONH$_2$ | 0.04 | 0.02 |
| 10 | PD26 | HSQGTFT SDYSKY LDVRRAQ DFVQWLMNT-CONH$_2$ | 0.02 | 0.06 |
| 11 | PD27 | HSQGTFT SDYSKY LDELRAY DFVQWLMNT-CONH$_2$ | 0.05 | 0.03 |
| 13 | PD29 | HSQGTFT SDYSKY LDSRRAH DFVQWLLNT-CONH$_2$ | 0.02 | 0.02 |
| 14 | PD30 | HSQGTFT SDYSKY LDSRRAQ DFVQWLMNP-CONH$_2$ | 0.04 | 0.12 |
| 15 | PD31 | HSQGTFT SDYSKY LDSRRAQ DFVQWLINY-CONH$_2$ | 0.06 | 0.04 |
| 20 | PD36 | HSQGTFT SDYSKY LDSIRAQ DFVQWLMDT-CONH$_2$ | 0.04 | 0.06 |
| 22 | PD38 | HSQGTFT SDYSKY LDSRRAQ DFVDWLMNE-CONH$_2$ | 0.01 | 0.14 |
| 24 | PD40 | HSQGTFT SDYSKY LDSRRAQ DFVQWLINT-CONH$_2$ | 0.03 | 0.02 |

TABLE 2-continued

| SEQ ID No. | PD-# | Sequence | EC$_{50}$ hGCGR (nm) | EC$_{50}$ hGLP1R (nm) |
|---|---|---|---|---|
| 27 | PD43 | HSQGTFF SDYSHWLDSRRAQ DFVQWLMNT-CONH$_2$ | 0.03 | 0.04 |
| 28 | PD44 | HSQGTFT SDYSKY LDWRRAQ DFVQWLQNT-CONH$_2$ | 0.02 | 0.01 |
| 29 | PD45 | HSQGTFT SDYSKY LDSKRAH DFVQWLLNT-CONH$_2$ | 0.03 | 0.02 |
| 32 | PD48 | HSQGTFT SDYSKY LDSRRAQ DFVDWLLNA-CONH$_2$ | 0.07 | 0.02 |
| 33 | PD49 | HSQGTFT SDYSKY LDSRRAQ DFVEWLMNN-CONH$_2$ | 0.01 | 0.01 |
| 34 | PD50 | HSQGTFT SDYSKY LDSRRAQ DFVDWLINS-CONH$_2$ | 0.02 | 0.01 |
| 35 | PD51 | HSHGTFT SDYSKY LDSRRAQ DFVQWLMTT-CONH$_2$ | 0.03 | 0.02 |
| 36 | PD52 | HSQGIFF SDYSKY LDSRRAQ DFVQWLMNT-CONH$_2$ | 0.03 | 0.02 |
| 37 | PD53 | HSQGTFL SDYSKY LDSRRAQ DFVQWLMNT-CONH$_2$ | 0.02 | 0.01 |
| 38 | PD54 | HSQGTFT SDYSWY LDSRRAQ DFVQWLMNT-CONH$_2$ | 0.03 | 0.02 |
| 39 | PD55 | HSQGTFT SDYSKY LDMQRAH DFVQWLMNT-CONH$_2$ | 0.01 | 0.01 |
| 40 | PD56 | HSQGTFT SDYSKY LDSRMAY DFVQWLMNT-CONH$_2$ | 0.08 | 0.05 |
| 41 | PD57 | HSQGTFT SDYSKY LDSRRAQ DFVQWLLNQ-CONH$_2$ | 0.02 | 0.01 |
| 42 | PD58 | HSQGTFF SDYSKY LDSRRAQ DFVQWLLET-CONH$_2$ | 0.03 | 0.02 |
| 43 | PD59 | HSQGTFT SDYSKY LDSRRAQ DFVQWLLDS-CONH$_2$ | 0.02 | 0.01 |

CONH$_2$ indicates that the carboxy terminus of the C-terminal peptide is amidated.

Co-agonist-based therapy has the potential to favorably impact both obesity and diabetes. Weight loss efficacy and reduction in food intake upon peripheral administration of the co-agonist oxyntomodulin (OXM) has been well validated in humans (Wynne et al., Diabetes 54: 2390-2395 (2005)). OXM has also been shown to reduce body weight in humans (See, for example, Published International Application Nos. WO03/022304, WO2004/062685, and WO2006/134340); however, the effects of the OXM peptide and similar co-agonist GLP-1 receptor/glucagon receptor (GLP-1R/GCGR) agonists on the glycemic control independent of weight loss have not been systematically studied. Furthermore, while OXM is a co-agonist of the GLP-1 and GCG receptors, its potency at the two receptors is relatively unbalanced: OXM is about 10-fold less potent at the GLP-1 receptor than the GCG receptor.

Native OXM, glucagon, and GLP-1 have a very short half-life and are rapidly inactivated by the cell surface dipeptidyl peptidase-4 (DPP-IV). Mutations can be incorporated into the these peptides to render them resistant to DPP-IV cleavage; however, many of these mutations have also been found to inactivate the native peptide or adversely affect the ability of the peptide to interact with the glucagon receptor (GCGR) or GLP-1 receptor (GLP-1R) (See Published International Application No. WO2007/100535, which is incorporated herein in its entirety). OXM, glucagon, and GLP-1 are also rapidly cleared by the kidneys. Conjugation of these peptides with bulky substituents such as polyethylene glycol may reduce renal clearance of the peptides; however, when these bulky substituents have been incorporated into the OXM peptide, many of resulting peptides have been found to have a reduced ability or no ability to effectively interact with the glucagon receptor.

Prior to the instant application, identification of peptides with appropriately balanced co-agonist activity and stability were identified empirically by trial and error. The phage display approach taken by the inventors has simplified the process of identifying co-agonist peptides. Using phage display technology, the inventors were able to identify from randomly mutated human glucagon a number of peptides that are co-agonists of the GCG and GLP-1 receptors. These peptides have previously unknown amino acid substitutions that have the effect of rendering the peptides co-agonists of the GCG and GLP-1 receptors. For example, substituting the threonine at position 7 of human glucagon with leucine results in a peptide with relatively balanced potent activity at the GCG and GLP-1 receptors (see peptide PD53) as did substituting the tyrosine at position 16 of human glucagon with tryptophan (see peptide PD44) or the methionine at position 27 of human glucagon with isoleucine (see peptide PD40) or substituting the threonine at position 29 of human glucagon with proline (see peptide PD30). As shown in Table 2, other combinations of previously unknown amino acid substitutions also resulted in peptides with relatively balanced activity and relatively potent activity at the GCG and GLP-1 receptors.

The limited in vivo stability of native GCG (and the peptides shown in Table 2 due to cleavage of the penultimate residue at the N-terminus by DPP-IV and rapid renal clearance, which necessitates frequent dosing (t.i.d. s.c. injections or continuous infusion) at high doses in humans, may be solved by mutating the site of DPP-IV cleavage and lipidating the peptide to increase its in vivo half-life ($t_{1/2}$), which is expected to render the co-agonist peptides suitable for at least once daily administration.

The tolerability profile of co-agonist peptides disclosed herein is anticipated to be similar to that of native OXM or GCG or GLP-1 in humans, which may be superior to that of conventional GLP-1 mimetics like exenatide and liraglutide. The chronic efficacy of the co-agonist peptides disclosed herein may therefore be better than conventional GLP-1 mimetics due to reduced nausea and vomiting, which have typically been dose limiting for the GLP-1 mimetics.

The co-agonist peptides herein are expected to the potential for improving glucose control. It has been shown that co-agonist peptides that have a balanced GLP-1 receptor and GCGR co-agonism give enhanced reductions in food intake and body weight with chronic administration and result in improved glucose tolerance.

To produce long-acting co-agonist peptides has not been straight forward. For example, as disclosed in Published International Application No. WO2010096142, site-specific conjugation of a bulky polyethylene glycol (PEG) substituent at various locations throughout the peptide resulted in a significant reduction in GCG receptor and/or GLP-1 receptor potency. Other methods to improve pharmacokinetic properties while maintaining GCG receptor activity such as adding a cholesterol conjugate to various positions in the peptide resulted in a significant serum shift of potency and decreased in vivo efficacy. However, as disclosed in Published International Application No. WO2010096142 and WO2009/155258, inclusion of a hydrophilic linker between the peptide and cholesterol group, or direct addition of an acyl chain to an amino acid at position 10, 20, 24, or the C-terminus provided co-agonist peptides with improved pharmacokinetic properties.

Based on published human studies with OXM, the co-agonist peptides disclosed herein are anticipated to exhibit at least comparable if not superior efficacy and a better safety profile than current anti-obesity agents such as orlistat (Xenical® (Roche), a lipase inhibitor) and sibutramine (Meridia® (Abbott Laboratories), a seratonin/norepinephrine re-uptake inhibitor), for which GI intolerance (diarrhea, flatulence) and hypertension are common side effects, respectively.

In particular aspects, the co-agonist peptides disclosed herein optionally include a protecting group covalently joined to the N-terminal amino group. A protecting group covalently joined to the N-terminal amino group of the peptide reduces the reactivity of the amino terminus under in vivo conditions. Amino protecting groups include —C1-10 alkyl, —C1-10 substituted alkyl, —C2-10 alkenyl, —C2-10 substituted alkenyl, aryl, —C1-6 alkyl aryl, —C(O)—(CH2) 1-6-COOH, —C(O)—C1-6 alkyl, —C(O)-aryl, —C(O)—O—C1-6 alkyl, or —C(O)—O-aryl. In particular embodiments, the amino terminus protecting group is selected from the group consisting of acetyl, propyl, succinyl, benzyl, benzyloxycarbonyl, and t-butyloxycarbonyl. Deamination of the N-terminal amino acid is another modification that is contemplated for reducing the reactivity of the amino terminus under in vivo conditions.

In particular aspects, the co-agonist peptides may be modified to have a protecting group covalently joined to the C-terminal carboxy group, which reduces the reactivity of the carboxy terminus under in vivo conditions. For example, carboxylic acid groups of the peptide, whether carboxyl-terminal or side chain, may be provided in the form of a salt of a pharmacologically-acceptable cation or esterified to form a C1-6 ester, or converted to an amide of formula $NRR_2$ wherein R and $R_2$ are each independently H or C1-6 alkyl, or combined to form a heterocyclic ring, such as a 5- or 6-membered ring. The carboxy terminus protecting group is preferably attached to the α-carbonyl group of the last amino acid. Carboxy terminus protecting groups include, but are not limited to, amide, methylamide, and ethylamide. Amino groups of the peptide, whether N-terminal or side chain, may be in the form of a pharmacologically-acceptable acid addition salt, such as the HCl, HBr, acetic, benzoic, toluene sulfonic, maleic, tartaric, and other organic salts, or may be modified to C1-6 alkyl or dialkyl amino or further converted to an amide.

The co-agonist peptides that are capable of acting as dual GLP-1 and glucagon agonists comprise the amino acid sequence of a peptide selected from Table 2 wherein the second amino acid from the N-terminus is substituted with an amino acid that renders the peptide resistant to cleavage and inactivation by dipeptidyl peptidase IV; a lipid moiety covalently linked to the co-agonist peptide at a lysine residue substituted for the tyrosine residue at position 10; optionally 0, 1, 2, 3, 4, 5, 6, 7, 8, 9, or 10 additional amino acid substitutions in addition to the substitution at position 2; and a protecting group that is joined to the C-terminal carboxy group. Optionally, the peptide may further comprises a protecting group joined to the N-terminal amino group.

In general, the co-agonist peptides comprises a substitution of the Ser at position 2 with Val, Ile, Asp, Glu, Met, Trp, Asn, D-Ala, D-Ser, or α-aminoisobutyric acid (aib). In particular embodiments, the Ser is substituted with D-Ser or aib.

In particular embodiments, the co-agonist peptide may further include substitutions of the amino acid at positions 16 and 18 with aib or Ala.

The lipid moiety may be a monocarboxylic acid comprising an aliphatic chain of 13 to 20 methylene groups (fatty acid) wherein one end of the molecule is the proximal end and the other end is the distal end and only one of the proximal end and the distal end has a carboxyl (COOH) group. The fatty acid may be represented by the structure $HO_2C(CH_2)_nCH_3$, wherein n is 11, 12, 13, 14, 15, 16, 17, or 18. The fatty acid may have one of the following structures

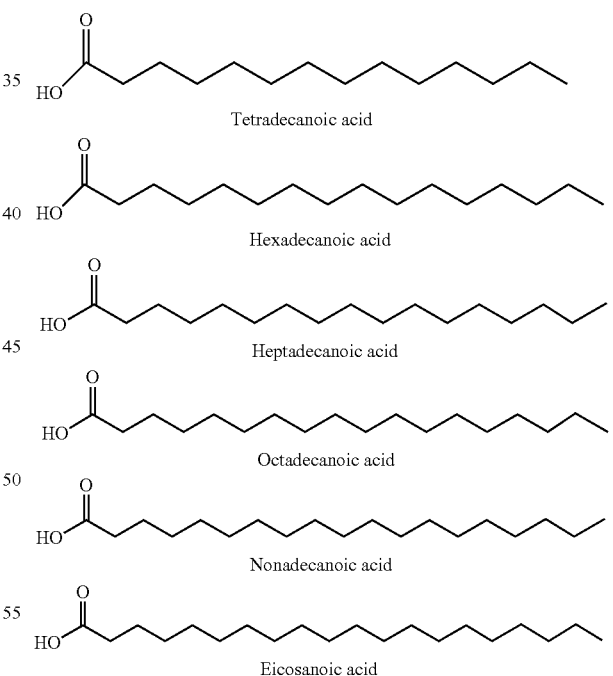

Tetradecanoic acid

Hexadecanoic acid

Heptadecanoic acid

Octadecanoic acid

Nonadecanoic acid

Eicosanoic acid

The lipid moiety may be an α,ω-dicarboxylic acid comprising an aliphatic chain of 13 to 20 methylene groups (fatty diacid) wherein one end of the molecule is the proximal end and the other end is the distal end and wherein the proximal end and the distal end both have a carboxyl (COOH) group. The fatty diacid may be represented by the structure $HO_2C(CH_2)_nCO_2H$, wherein n is 11, 12, 13, 14, 15, 16, 17, or 18. The fatty diacid may have one of the following structures

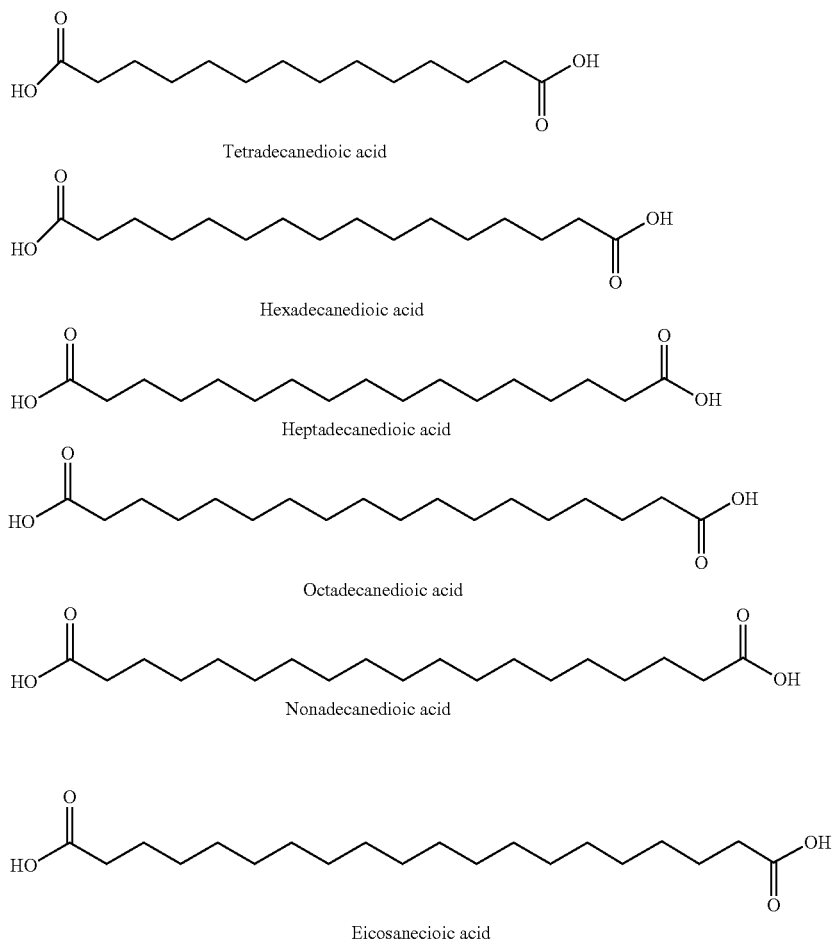

Tetradecanedioic acid

Hexadecanedioic acid

Heptadecanedioic acid

Octadecanedioic acid

Nonadecanedioic acid

Eicosanecioic acid

As a component of the co-agonist peptide, the acid functionality at the proximal end of the fatty diacid is conjugated to the amino group of a linker in a C(O)—NH linkage and the acid functionality at the distal end of the fatty diacid is a free carboxyl group (COOH). The COOH group at the distal end helps confer a longer half-life to the co-agonist peptide by its ability to non-covalently bind to serum albumin, a known carrier for fatty acids in serum. The COOH group enhances duration of action as it provides a better non-covalent interaction with serum albumin than peptides that have been acylated using a fatty acid, which bind serum albumin less efficiently and form a less stable non-covalent interaction with the serum albumin.

When the fatty acid or diacid is conjugated to a linking moiety or linker, it is subsequently referred to as a fatty acid component.

The linker may be PEG$_2$ (8-amino-3,6-dioxaoctanoic acid) linked to Gamma-Glutamic acid (gamma-Glu, γGlu, or γE), which has the structure

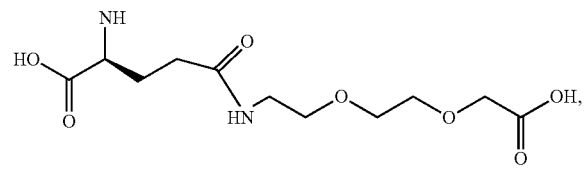 [SMILES: N[C@@H](CCC(=O)NCCOCCOCC(=O)O)C(=O)O]

or the linker may be Gamma-Glutamic acid-gamma glutamic acid (gamma-Glu-gamma-Glu, or γGlu-γGlu, or γEγE), which has the structure

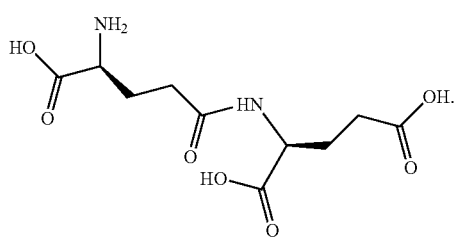 [SMILES: N[C@@H](CCC(=O)N[C@@H](CCC(=O)O)C(=O)O)C(=O)O]

The structure of K(PEG$_2$PEG$_2$γE-fatty acid) wherein the linker is PEG$_2$PEG$_2$γE and the fatty acid component comprises C14, C16, C17, C18, C19, or C20 fatty acid is represented by

21

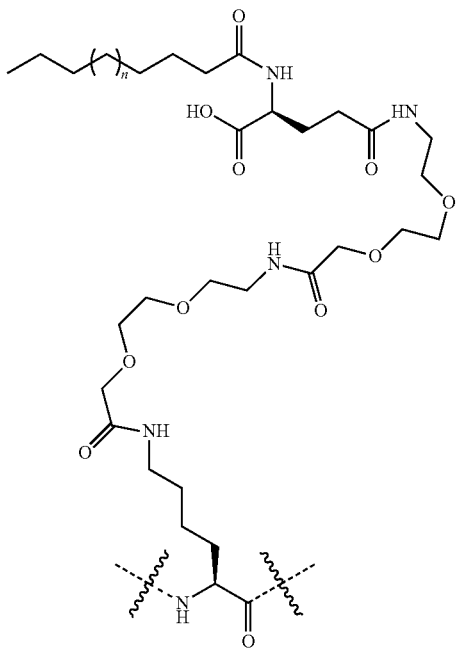

22

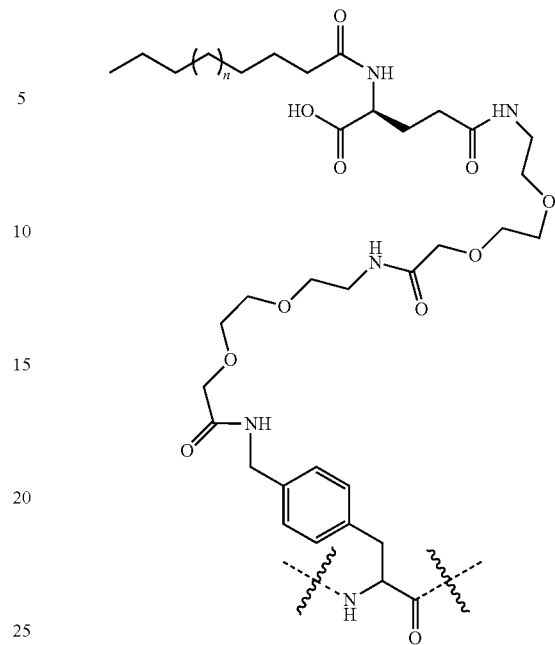

wherein n is 7, 9, 10, 11, 12, 13, or 14 respectively, and the wavy lines represent the bonds between adjacent amino acids in the co-agonist peptide sequence.

The structure of pAF(PEG$_2$PEG$_2$γE-fatty acid) wherein the linker is PEG$_2$PEG$_2$γE and the fatty acid component comprises C14, C16, C17, C18, C19, or C20 is represented by wherein n is 7, 9, 10, 11, 12, 13, or 14, respectively, and the wavy lines represent the bonds between adjacent amino acids in the co-agonist peptide sequence.

The structure of K(γEγE-fatty acid) wherein the linker is γEγE and the fatty acid component comprises C14, C16, C17, C18, C19, or C20 fatty acid is represented by

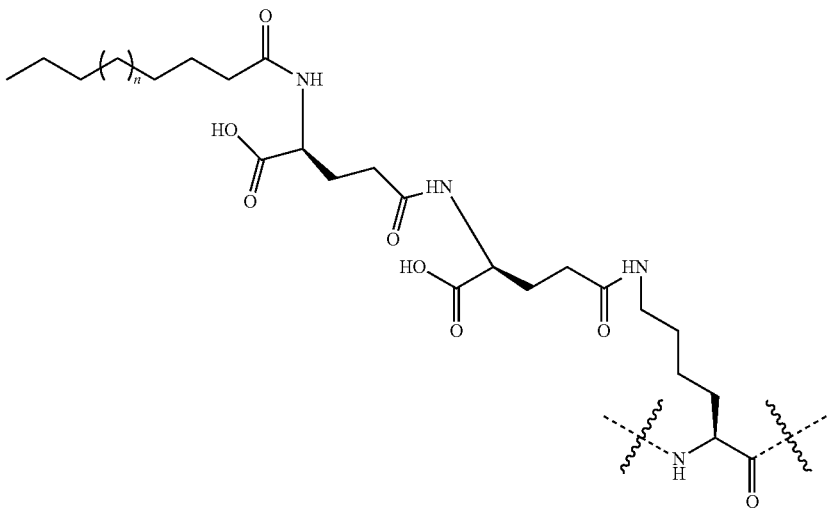

wherein n is 7, 9, 10, 11, 12, 13, or 14, respectively, and the wavy lines represent the bonds between adjacent amino acids in the co-agonist peptide sequence.

The structure of K(PEG$_2$PEG$_2$γE-fatty acid) wherein the linker is PEG$_2$PEG$_2$γE and the fatty acid component comprises C14, C16, C17, C18, C19, or C20 fatty diacid is represented by

23

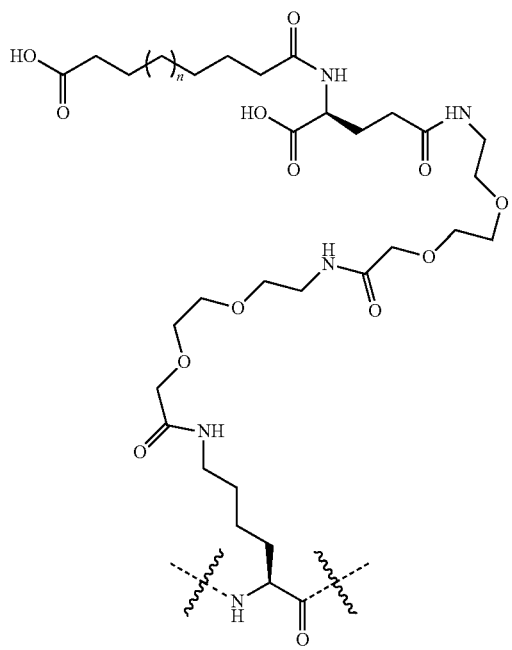

wherein n is 7, 9, 10, 11, 12, 13, or 14 respectively, and the wavy lines represent the bonds between adjacent amino acids in the co-agonist peptide sequence.

The structure of pAF(PEG$_2$PEG$_2$γE-fatty acid) wherein the linker is PEG$_2$PEG$_2$γE and the fatty acid component comprises C14, C16, C17, C18, C19, or C20 fatty diacid is represented by

24

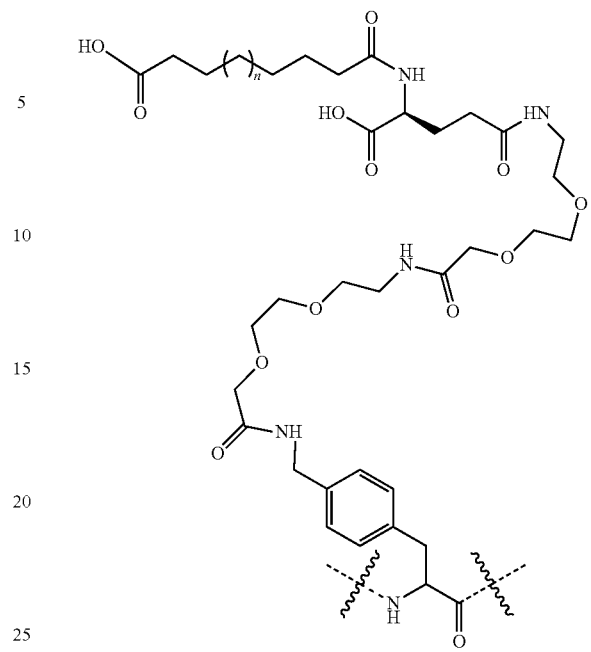

wherein n is 7, 9, 10, 11, 12, 13, or 14, respectively, and the wavy lines represent the bonds between adjacent amino acids in the co-agonist peptide sequence.

The structure of K(γEγE-fatty acid) wherein the linker is γEγE and the fatty acid component comprises C14, C16, C17, C18, C19, or C20 fatty diacid is represented by

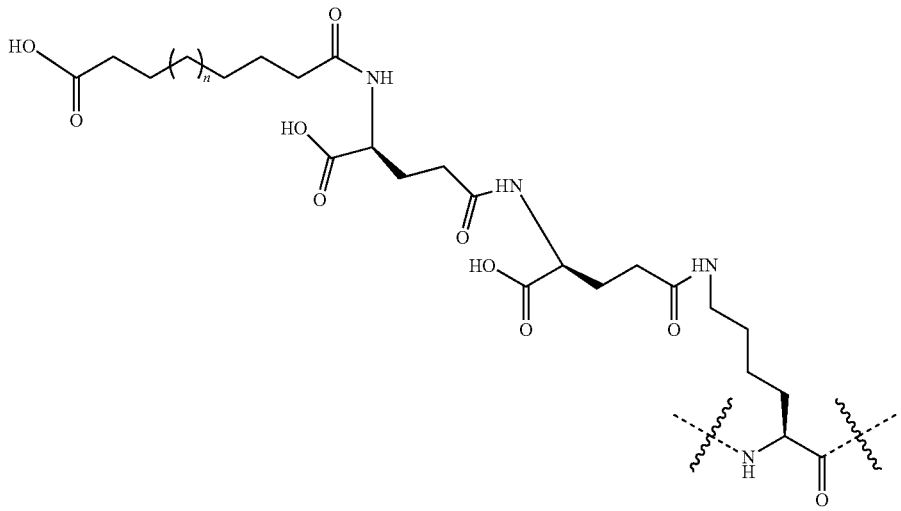

wherein n is 7, 9, 10, 11, 12, 13, or 14, respectively, and the wavy lines represent the bonds between adjacent amino acids in the co-agonist peptide sequence.

In particular aspects, the co-agonist peptide may comprise a lysine residue at the C-terminus that is conjugated to a γE residue to provide a KγE at position 30 in the co-agonist peptide, which is represented by

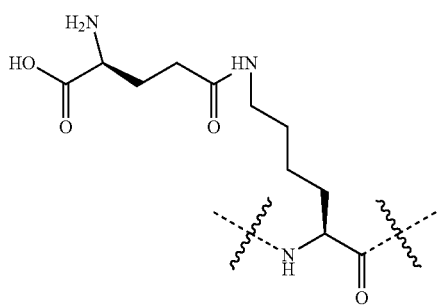

wherein the wavy lines represent the bonds between adjacent amino acids in the co-agonist peptide sequence.

The co-agonist peptides disclosed herein may have anywhere from at least about 1% (including at least about 1.5%, 2%, 5%, 7%, 10%, 20%, 30%, 40%, 50%, 60%, 75%, 100%, 125%, 150%, 175%) to about 200% or higher activity at the GLP-1 receptor relative to native GLP-1 and anywhere from at least about 1% (including about 1.5%, 2%, 5%, 7%, 10%, 20%, 30%, 40%, 50%, 60%, 75%, 100%, 125%, 150%, 175%, 200%, 250%, 300%, 350%, 400%, 450%) to about 500% or higher activity at the glucagon receptor relative to native glucagon. In some embodiments, the co-agonist peptides described herein exhibit no more than about 100%, 1000%, 10,000%, 100,000%, or 1,000,000% of the activity of native glucagon at the glucagon receptor. In some embodiments, the co-agonist peptides described herein exhibit no more than about 100%, 1000%, 10,000%, 100,000%, or 1,000,000% of the activity of native GLP-1 at the GLP-1 receptor. In exemplary embodiments, a co-agonist peptide may exhibit at least 10% of the activity of native glucagon at the glucagon receptor and at least 50% of the activity of native GLP-1 at the GLP-1 receptor, or at least 40% of the activity of native glucagon at the glucagon receptor and at least 40% of the activity of native GLP-1 at the GLP-1 receptor, or at least 60% of the activity of native glucagon at the glucagon receptor and at least 60% of the activity of native GLP-1 at the GLP-1 receptor.

Selectivity of a glucagon peptide for the glucagon receptor versus the GLP-1 receptor can be described as the relative ratio of glucagon/GLP-1 activity (the peptide analog's activity at the glucagon receptor relative to native glucagon, divided by the peptide's activity at the GLP-1 receptor relative to native GLP-1). For example, a co-agonist peptide that exhibits 60% of the activity of native glucagon at the glucagon receptor and 60% of the activity of native GLP-1 at the GLP-1 receptor has a 1:1 ratio of glucagon/GLP-1 activity. Exemplary ratios of glucagon/GLP-1 activity include about 1:1, 1.5:1, 2:1, 3:1, 4:1, 5:1, 6:1, 7:1, 8:1, 9:1 or 10:1, or about 1:10, 1:9, 1:8, 1:7, 1:6, 1:5, 1:4, 1:3, 1:2, or 1:1.5. As an example, a glucagon/GLP-1 activity ratio of 10:1 indicates a 10-fold selectivity for the glucagon receptor versus the GLP-1 receptor. Similarly, a GLP-1/glucagon activity ratio of 10:1 indicates a 10-fold selectivity for the GLP-1 receptor versus the glucagon receptor.

Pharmaceutical Compositions

Further provided are pharmaceutical compositions comprising a therapeutically effective amount of one or more of the co-agonist peptides disclosed herein for the treatment of a metabolic disorder in an individual. Such disorders include, but are not limited to, obesity, metabolic syndrome or syndrome X, type II diabetes, complications of diabetes such as retinopathy, hypertension, dyslipidemias, cardiovascular disease, gallstones, osteoarthritis, and certain forms of cancers. The obesity-related disorders herein are associated with, caused by, or result from obesity.

"Obesity" is a condition in which there is an excess of body fat. The operational definition of obesity is based on the Body Mass Index (BMI), calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk for obesity" is an otherwise healthy subject with a BMI of 25 kg/m2 to less than 30 kg/m2 or a subject with at least one co-morbidity with a BMI of 25 kg/m2 to less than 27 kg/m2.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m2. In Asian countries, including Japan, an "obese subject" refers to a subject with at least one obesity-induced or obesity-related co-morbidity that requires weight reduction or that would be improved by weight reduction, with a BMI greater than or equal to 25 kg/m2. In Asian countries, a "subject at risk of obesity" is a subject with a BMI of greater than 23 kg/m2 to less than 25 kg/m2.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, non-alcoholic fatty liver disease (NAFLD), non-alcoholic steatohepatitis (NASH), fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

U.S. Pat. No. 6,852,690, which is incorporated herein in its entirety, discloses methods for enhancing metabolism of nutrients comprising administering to a non-diabetic patient a formulation comprising a nutritively effective amount of one or more nutrients or any combination thereof and one or more insulinotropic peptides. The co-agonist peptides disclosed herein are insulinotropic and can be administered to patients with a disturbed glucose metabolism such as insulin resistance but no overt diabetes, as well as patients who for any reason cannot receive nutrition through the alimentary canal. Such patients include surgery patients, comatose patients, patients in shock, patients with gastrointestinal disease, patients with digestive hormone disease, and the like. In particular, obese patients, atherosclerotic patients, vascular disease patients, patients with gestational diabetes, patients with liver disease such as liver cirrhosis, patients with acromegaly, patients with glucorticoid excess such as cortisol treatment or Cushings disease, patients with activated counter regulatory hormones such as would occur after trauma, accidents and surgery and the like, patients with hypertriglyceridemia and patients with chronic pancreatitis can be readily and suitably nourished according to the invention without subjecting the patient to hypo- or hyperglycemia. In particular, the administration to such a patient aims to provide a therapy to as rapidly as possible deliver the nutritional and caloric requirements to the patient while maintaining his plasma glucose below the so-called renal threshold of about 160 to 180 milligrams per deciliter of glucose in the blood. Although normal patients not having glucose levels just below the renal threshold can also be treated according to the invention as described above, patients with disturbed glucose metabolism such as hyperglycemic patients whose plasma glucose level is just above the renal threshold also find the therapy suitable for their condition. In particular, such patients who have a degree of hyperglycemia below the renal threshold at intermittent intervals can receive a combination treatment of nutrients plus insulinotropic peptides according to any of the following regimens. Normal patients not suffering from such hyperglycemia can also be treated using the co-agonist peptides disclosed herein.

The co-agonist peptides disclosed herein may be used in a pharmaceutical composition when combined with a pharmaceutically acceptable carrier. Such compositions comprise a therapeutically-effective amount of one or more of the co-agonist peptides disclosed herein and a pharmaceutically acceptable carrier. Such a composition may also be comprised of (in addition to the co-agonist peptides disclosed herein and a carrier) diluents, fillers, salts, buffers, stabilizers, solubilizers, and other materials well known in the art. Compositions comprising the co-agonist peptides disclosed herein can be administered, if desired, in the form of salts provided the salts are pharmaceutically acceptable. Salts may be prepared using standard procedures known to those skilled in the art of synthetic organic chemistry.

The term "individual" is meant to include humans and companion or domesticated animals such as dogs, cats, horses, and the like. Therefore, the compositions comprising a compound as disclosed herein are also useful for treating or preventing obesity and obesity-related disorders in cats and dogs. As such, the term "mammal" includes companion animals such as cats and dogs.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. It will be understood that, as used herein, references to the OXM analogs disclosed herein are meant to also include the pharmaceutically acceptable salts.

As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration. The co-agonist peptides disclosed herein may be in multimers (for example, heterodimers or homodimers) or complexes with itself or other peptides. As a result, pharmaceutical compositions of the invention may comprise one or more co-agonist peptides disclosed herein in such multimeric or complexed form.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially, or simultaneously.

The pharmacological composition can comprise one or more co-agonist peptides disclosed herein; one or more co-agonist peptides disclosed herein and one or more other agents for treating a metabolic disorder; or the pharmacological composition comprising the one or more co-agonist peptides disclosed herein can be used concurrently with a pharmacological composition comprising an agent for treating a metabolic disorder. Such disorders include, but are not limited to, obesity, metabolic syndrome or syndrome X, type II diabetes, complications of diabetes, hypertension, dyslipidemias, cardiovascular disease, gallstones, osteoarthritis, and certain forms of cancers.

When the pharmacological composition comprises another agent for treating a metabolic disorder or the treatment includes a second pharmacological composition comprising an agent for treating a metabolic disorder, the agent includes, but are not limited to, cannabinoid (CB1) receptor antagonists, glucagon like peptide 1 (GLP-1) receptor agonists, glucagon receptor antagonists, lipase inhibitors, leptin, tetrahydrolipstatin, 2-4-dinitrophenol, acarbose, sibutramine, phentamine, fat absorption blockers, simvastatin, mevastatin, ezetimibe, atorvastatin, sitagliptin, metformin, orlistat, Qnexa, topiramate, naltrexone, bupriopion, phentermine, losartan, losartan with hydrochlorothiazide, and the like.

Examples of other active ingredients that may be administered separately or in the same pharmaceutical composition in combination with a co-agonist peptide as described herein include, but are not limited to:

(1) other dipeptidyl peptidase-IV (DPP-4) inhibitors (e.g., sitagliptin, alogliptin, linagliptin, vildagliptin, saxagliptin and omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); (3) insulin or insulin analogs (e.g., insulin detemir, insulin glulisine, insulin degludec, insulin glargine (U100 or U300), insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., such as those disclosed in WO 98/04528, WO 99/01423, WO 00/39088, and WO 00/69810);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators;

(21) other agonists of the G-protein-coupled receptors: (i) GPR-109, (ii) GPR-119 (e.g., MBX2982 and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5[4-[[3-[4-(3-aminopropoxy)-2,6-dimethylphenyl]phenyl]methoxy]phenyl]isothiazole-3-ol 1-oxide);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof:

(37) FGF-21 and analogs and derivatives thereof; and

(38) FGF21 mimetics such as agonist antibodies that binds the ß-Klotho and FCFR1c complex.

Of particular interest are metformin hydrochloride, pioglitazone, rosiglitazone, simvastatin, atorvastatin, or a sulfonylurea.

Antiobesity compounds that can be combined with compounds as disclosed herein include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557; CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see Chaki et al., "Recent advances in feeding suppressing agents: potential therapeutic strategy for the treatment of obesity," Expert Opin. Ther. Patents, 11: 1677-1692 (2001); Spanswick and Lee, "Emerging antiobesity drugs," Expert Opin. Emerging Drugs, 8: 217-237 (2003); Fernandez-Lopez, et al., "Pharmacological Approaches for the Treatment of Obesity," Drugs, 62: 915-944 (2002); and Gadde, et al., "Combination pharmaceutical therapies for obesity," Exp. Opin. Pharmacother., 10: 921-925 (2009).

In another aspect of the invention, a pharmaceutical composition is disclosed which comprises one or more of the following agents:

(a) a compound as disclosed herein;

(b) one or more compounds selected from the group consisting of:

(1) other dipeptidyl peptidase-IV (DPP-4) inhibitors;

(2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814;

(3) sulfonylurea and non-sulfonylurea insulin secretagogues, (e.g., tolbutamide, glyburide, glipizide, glimepiride, mitiglinide, and meglitinides, such as nateglinide and repaglinide);

(4) α-glucosidase inhibitors (e.g., acarbose, voglibose and miglitol);

(5) glucagon receptor antagonists;

(6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA: cholesterol acyltransferase inhibitors (e.g., avasimibe);

(7) HDL-raising drugs, such as niacin or a salt thereof and extended-release versions thereof; MK-524A, which is a combination of niacin extended-release and the DP-1 antagonist MK-524; and nicotinic acid receptor agonists;

(8) antiobesity compounds;

(9) agents intended for use in inflammatory conditions, such as aspirin, non-steroidal anti-inflammatory drugs (NSAIDs), glucocorticoids, and selective cyclooxygenase-2 (COX-2) inhibitors;

(10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers);

(11) glucokinase activators (GKAs) (e.g., AZD6370);

(12) inhibitors of 11β-hydroxysteroid dehydrogenase type 1 (e.g., such as those disclosed in U.S. Pat. No. 6,730, 690; WO 03/104207; and WO 04/058741);

(13) inhibitors of cholesteryl ester transfer protein (CETP), (e.g., torcetrapib and MK-0859);

(14) inhibitors of fructose 1,6-bisphosphatase (e.g., such as those disclosed in U.S. Pat. Nos. 6,054,587; 6,110, 903; 6,284,748; 6,399,782; and 6,489,476);

(15) inhibitors of acetyl CoA carboxylase-1 or 2 (ACC1 or ACC2);

(16) AMP-activated Protein Kinase (AMPK) activators;

(17) agonists of the G-protein-coupled receptors: (i) GPR-109, (ii) GPR-119 (e.g., MBX2982, and PSN821), and (iii) GPR-40 (e.g., TAK875, 5-[4-[[(1R)-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide);

(18) SSTR3 antagonists (e.g., such as those disclosed in WO 2009/011836);

(19) neuromedin U receptor agonists (e.g., such as those disclosed in WO2009/042053, including, but not limited to, neuromedin S (NMS));

(20) inhibitors of stearoyl-coenzyme A delta-9 desaturase (SCD); (21) GPR-105 antagonists (e.g., such as those disclosed in WO 2009/000087);

(22) inhibitors of glucose uptake, such as sodium-glucose transporter (SGLT) inhibitors and its various isoforms, such as SGLT-1; SGLT-2 (e.g., ASP1941, TS071, BI10773, tofogliflozin, LX4211, canagliflozin, dapagliflozin and remogliflozin; and SGLT-3);

(23) inhibitors of acyl coenzyme A:diacylglycerol acyltransferase 1 and 2 (DGAT-1 and DGAT-2);

(24) inhibitors of fatty acid synthase;

(25) inhibitors of acyl coenzyme A:monoacylglycerol acyltransferase 1 and 2 (MGAT-1 and MGAT-2);

(26) agonists of the TGR5 receptor (also known as GPBAR1, BG37, GPCR19, GPR131, and M-BAR);

(28) bromocriptine mesylate and rapid-release formulations thereof, and

(29) IL-1b antibodies (e.g., XOMA052, and canakinumab);

(30) FGF-21 or analog or derivative;

(31) FGF21 mimetics such as agonist antibodies that binds the ß-Klotho and FCFR1c complex; and (c) a pharmaceutically acceptable carrier.

When a co-agonist peptide of the present invention is used contemporaneously with one or more other drugs, peptides, or proteins, a pharmaceutical composition containing such other drugs, peptides, or proteins in addition to the co-agonist peptide of the present invention may be provided. Accordingly, the pharmaceutical compositions of the present invention include those that also contain one or more other active ingredients, in addition to a co-agonist peptide of the present invention.

Methods of administrating the pharmacological compositions comprising the one or more co-agonist peptides disclosed herein to an individual include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Intraventricular injection may be facilitated by an intraventricular catheter attached to a reservoir (for example, an Ommaya reservoir). Pulmonary administration may also be employed by use of an inhaler or nebulizer, and formulation with an aerosolizing agent. It may also be desirable to administer the one or more co-agonist peptides disclosed herein locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the co-agonist peptides disclosed herein including, but not limited to, encapsulation in liposomes, microparticles, microcapsules; minicells; polymers; capsules; tablets; and the like. In one embodiment, the co-agonist peptides disclosed herein may be delivered in a vesicle, in particular a liposome. In a liposome, the co-agonist peptides disclosed herein are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the co-agonist peptides disclosed herein can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (for example, the brain), thus requiring only a fraction of the systemic dose. See, for example, Goodson, In: *Medical Applications of Controlled Release*, 1984. (CRC Press, Bocca Raton, Fla.).

The amount of the compositions comprising one or more of the co-agonist peptides disclosed herein which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the composition with which to treat each individual patient. Initially, the attending physician will administer low doses of the composition and observe the patient's response. Larger doses of the composition may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. However, suitable dosage ranges for intravenous administration of the compositions comprising the one or more co-agonist peptides disclosed herein are generally about 5-500 micrograms (μg) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions comprising the one or more co-agonist peptides disclosed herein of the present invention. Dosage will also vary according to the age, weight and response of the individual patient.

Further provided is a pharmaceutical pack or kit, comprising one or more containers filled with one or more of the ingredients of the pharmaceutical compositions and co-agonist peptides disclosed herein. Optionally associated with such container(s) may be a notice in the form prescribed by a governmental agency regulating the manufacture, use or sale of pharmaceuticals or biological products, which notice reflects approval by the agency of manufacture, use or sale for human administration.

The present invention further provides a method for treating a patient for a metabolic disease or disorder comprising administering the patient an effective amount of a composition comprising any one or more of the aforementioned co-agonist peptides to treat the metabolic disease or disorder in the patient.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned co-agonist peptides for manufacture of a medicament for the treatment of a metabolic disease or disorder.

The present invention further provides for the use of any one of the aforementioned co-agonist peptides for manufacture of a medicament for the treatment of a metabolic disease or disorder.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the medicament is for treatment of more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

Further provided is method for treating a metabolic disease or disorder in a patient or individual comprising: administering to the patient or individual an effective amount of any one of the aforementioned compositions comprising a co-agonist peptide and administering to the patient or individual an effective amount of a composition comprising an insulin or insulin analog to treat the metabolic disease or disorder in the patient or individual.

In particular aspects, the composition comprising the co-agonist peptide is administered at a time prior to the time the composition comprising the insulin or insulin analog is administered. In another aspect, the composition comprising the insulin or insulin analog is administered at a time prior to the time the composition comprising the co-agonist peptide is administered. In a further still aspect, the composition comprising the co-agonist peptide is administered at the same time as the composition comprising the insulin or insulin analog is administered.

In particular aspects, the insulin analog is insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides a composition comprising any one of the aforementioned co-agonist peptides; an insulin or insulin analog; and, a pharmaceutically acceptable carrier.

The present invention further provides for the use of a composition comprising any one of the aforementioned co-agonist peptides; an insulin or insulin analog; and, a pharmaceutically acceptable carrier for the treatment of a metabolic disease or disorder.

In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The present invention further provides for the use of a composition comprising any one of the aforementioned co-agonist peptides; an insulin or insulin analog; and, a pharmaceutically acceptable carrier for the manufacture of a medicament for the treatment of a metabolic disease or disorder.

In particular aspects, the insulin analog comprises insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The following examples are intended to promote a further understanding of the present invention.

EXAMPLE 1

Co-agonists were identified using a phage display protocol as set forth below.
Cell Lines Hek 293 Tet GCGr and Hek 293 Tet GLP1r stable inducible cell lines were generated to obtain high level of expressed receptors. DNA encoding the human GCG receptor and human GLP1 receptor, both including DNA encoding Myc-DDK tag for FLAG detection were each subcloned as a NheI/ClaI (NheI #R01315 and ClaI #R01975, BioLabs) fragments into the pTRE2hyg vector (Clontech), using Rapid Ligation kit (N. 04898125001, Roche), and transformed into DH5α CaCl$_2$ competent cells. The following oligos were used to introduce NheI and ClaI restriction site in the amplified fragment for the cloning step:
GCGR NheI For: 5'-GAC TGC TAG CAC CAT GCC CCC CTG CCA GCC AC-3' (SEQ ID NO:58);
GLP1R NheI For: 5'-GAC TGC TAG CAC CAT GGC CGG CGC CCC CGG C-3' (SEQ ID NO:59); and
GCGR/GLP1R ClaI Rev: 5'-ATC GAT CGA TTT AAA CCT TAT CGT CGT CAT CCT TGT AAT C-3' (SEQ ID NO:60).
Once obtained, recombinant plasmids were purified using Wizard SV Clean-Up System (Promega) and checked by sequencing.

Cells were cultured at 37° C. with 5% CO$_2$ in DMEM medium (Gibco, Life technologies) supplemented with 10% Fetal Bovine Serum (Gibco, Life technologies), 100 μg/mL Penicillin/Streptomycin (Gibco Life technologies REF 1514-122), 1% L-Glutamine (Gibco Life Technologies REF 25030-024), 250 μg/mL Geneticin (G418 Sulfate 11811-031, Life Technologies), 0.5 μg/mL Puromycin (Sigma Aldrich P8833-100MG) and 100 μg/mL HygromycinB (Sigma Aldrich H3274-1G).

Transfections of Hek293 Tet cells either with pTRE2hyg GCGr or with pTRE2hyg GLP1r plasmid were made using Lipofectamine reagent (Invitrogen 18324-020), according to manufacturer's instructions. Stable clones were selected in culture medium containing 100 μg/mL of HygromycinB in about ⅔ weeks. Individual clones were then characterized by Western Blot Cell based Elisa assay for their level of expression upon induction with 1 μg/mL Doxycycline (Sigma Aldrich N.D9891) for 20 hours. The highest responding clones were selected, frozen and stored in liquid nitrogen for further experiments.
Proteic Extracts and Western Blot Analysis GCG receptor and GLP1 receptor gene expression in Hek293 Tet GCGr and Hek293 Tet GLP1r cells were induced with 1 μg/mL Doxycycline (Sigma Aldrich N.D9891) for 20 hours. Cells were washed with cold PBS1X, harvested in falcon and centrifuged at 4° C. 1200 rpm for 5 minutes. To each pellet was added 1 mL of Complete Lysis-M (Roche Cat. No. 04719956001) for efficient protein extraction. Protein extracts were analyzed by electrophoresis on polyacrylamide gel (SDS-PAGE), and samples were loaded on a 4-12% Bis-Tris gel (NuPage Invitrogen). After blotting on a nitrocellulose filter (Nitrocellulose Blotting Membrane 0.2 μm #10600001, GE Healthcare Life Science), the membrane was incubated with α-Flag 1:1000 (Monoclonal ANTI-FLAG M2-Peroxidase, Sigma Aldrich Cat. A8592) followed by incubation with α-mouse secondary antibody (Goat α-mouse IRDYe680 92632210 Lot#B70907-01 ODYSSEY Infrared Imaging System LI-COR)
Cell Based ELISA Assay Hek293 Tet GCGr or Hek293 Tet GLP1r cells were seeded at 8×10$^6$ cells/10 cm plate and induced, if the case, with 1 μg/mL Doxycycline. After 20 hours cells were detached and plated on 96-well poly-lysine coated plate (Poly-L-lysine, Sigma Aldrich Cat. P4707) at about 50,000 cells/well over night at 37° C. The day after, cells were fixed with 4% of paraformaldehyde (Electron microscopy sciences Cat N.157-8) for 20 minutes at room temperature, and α-FlagHRP conjugated mAb (Monoclonal ANTI-FLAG M2-Peroxidase, Sigma Aldrich Cat. A8592) diluted 1:1000 in 3% Milk-PBS1X-Tween 0.05% was added. Development was made with Tetramethylbenzidine (TMB N.8665 SIGMA Aldrich) liquid substrate for 30 minutes reading Absorbance at 450 and 620 nm with Elisa Reader Thermoscientific Multiskan Ascent.
Library Construction
pIII-GCG pIII-GLP1 Positive Control Phages and Peptide Phage Libraries In order to obtain positive control phages for libraries screening, DNA sequences coding for Glucagon (GCG) and for GLP-1 peptides were sub-cloned as a NcoI-NotI (NcoI #R0193S and NotI #R0189L BioLabs) fragment into pCAN-TAB6 phagemid, fused with the N-terminus sequence of M13 bacteriophage coat protein pIII. Once obtained, the GCG and GLP-1 phagemids were converted to phage particles by superinfecting TG1 transformed cells with helper phage K07, purified on a CsCl gradient and titrated as CFU (colony forming units).

To introduce diversity and design the peptide phage library, the GCG sequence was divided in five domains to generate five sub-libraries. In each sub-library, a cassette of seven amino acids was mutagenized and combined with the two amino acids in the position 27 and 28 of the sequence. In one sub-library two extra amino acids at N-terminus were also added. In each position 45% of amino acids were maintained as wild type, while 55% were the other possible amino acids (except cysteine to avoid disulfide bridges formation) in equal percentages. (See FIG. 1).

The sequences shown in FIG. 1 are also shown in Table 3.

TABLE 3

Library Sequences

| SEQ ID NO: | Name | Sequence |
|---|---|---|
| 53 | Lib1<br>(1)-(7) X is any amino acid with the proviso that for each position in 45% of the peptides the amino acid is maintained as the wild type amino acid while in 55% of the peptides the amino acid is any other amino acid except cysteine<br>(29)-(30) X is any amino acid with the proviso that for each position in 45% of the peptides the amino acid is maintained as the wild type amino acid while in 55% of the peptides the amino acid is any other amino acid except cysteine | XXXXXXXFTSDYSKYL DSRRAQDFVQWLXXT |
| 54 | Lib2<br>(1)-(7) X is any amino acid with the proviso that for each position in 45% of the peptides the amino acid is maintained as the wild type amino acid while in 55% of the peptides the amino acid is any other amino acid except cysteine<br>(27)-(28) X is any amino acid with the proviso that for each position in 45% of the peptides the amino acid is maintained as the wild type amino acid while in 55% of the peptides the amino acid is any other amino acid except cysteine | XXXXXXXSDYSKYLDS RRAQDFVQWLXXT |
| 55 | Lib3<br>(7)-(13) X is any amino acid with the proviso that for each position in 45% of the peptides the amino acid is maintained as the wild type amino acid while in 55% of the peptides the amino acid is any other amino acid except cysteine<br>(27)-(28) X is any amino acid with the proviso that for each position in 45% of the peptides the amino acid is maintained as the wild type amino acid while in 55% of the peptides the amino acid is any other amino acid except cysteine | HSQGTFXXXXXXXLDS RRAQDFVQWLXXT |
| 56 | Lib4<br>(14)-(20) X is any amino acid with the proviso that for each position in 45% of the peptides the amino acid is maintained as the wild type amino acid while in 55% of the peptides the amino acid is any other amino acid except cysteine | HSQGTFTSDYSKYXXX XXXXDFVQWLXXT |

TABLE 3-continued

Library Sequences

| SEQ ID NO: | Name | Sequence |
|---|---|---|
|  | (27)-(28) X is any amino acid with the proviso that for each position in 45% of the peptides the amino acid is maintained as the wild type amino acid while in 55% of the peptides the amino acid is any other amino acid except cysteine |  |
| 57 | Lib5<br>(21)-(29) X is any amino acid with the proviso that for each position in 45% of the peptides the amino acid is maintained as the wild type amino acid while in 55% of the peptides the amino acid is any other amino acid except cysteine | HSQGTFTSDYSKYLDS RRAQXXXXXXXXX |

The randomized single strand oligonucleotides for the library constructions were generated by trimer-based synthesis (ELLA Biotech). The oligo sequences are shown in the Table of Primers wherein the presence of diversity is represented by $X_n$ wherein X represents a mixture of 19 codons, each codon encoding one of 19 amino acids except for Cys and wherein n is one of 21 different codon mixtures as shown in FIG. 3 wherein each mixture has a particular frequency of the 18 codons.

Each $X_n$ represents a codon of three nucleotides $X_1X_2X_3$ wherein each X is independently A, G, C, or T with the proviso that $X_1$ is not T if $X_2$ is G or C and $X_3$ is T or if $X_1$ is T, then $X_3$ is not T and wherein the combinations of $X_1X_2X_3$ have the triplet nucleotide sequences as shown in FIG. 3 for each particular Xn. For example, FIG. 3 shows that for $X_{10}$ the codons encode 19 different amino acids (excluding Cys) and the codon for each amino acid is 5.26% of the mixture; for $X_1$ the codons encode 19 different amino acids (excluding Cys) and the codon encoding Asp comprises 45% of the mixture of codons and the codons for each of the remainder of the amino acids comprises 3% of the mixture.

Table of Primers

| Name | Sequence | SEQ ID NO: |
|---|---|---|
| GCG_lib1_for | 5'-GCCGGATGGCA$X_{10}X_{10}X_{04}X_{07}X_{02}X_{03}X_{08}$TTTAC CTCTGATTACAGCAAATACCT GGATTCTAGACGTGCTCAAGAC-3' | 61 |
| GCG_lib2_for | 5'-GCCGGCCATGGCA$X_{04}X_{07}X_{02}X_{03}X_{08}X_{06}X_{08}$TCT GATTACAGCAAATACCTGGA TTCTAGACGTGCTCAAGAC-3' | 62 |
| GCG_lib3_for | 5'-GCCGGCCATGGCACATTCTCAGGGTACCTTT$X_{08}X_{07}$ $X_{01}X_{09}X_{07}X_{05}X_{09}$CTGGA TTCTAGACGTGCTCAAGAC-3' | 63 |

Table of Primers

| Name | Sequence | SEQ ID NO: |
|---|---|---|
| GCG_lib4_for | 5'-GCCGGCCATGGCACATTCTCAGGGTACCTTCAC CAGCGACTACAGCAAGTAC-3' | 64 |
| GCG_lib5_for | 5'-CCGGCCATGGCACATTCTCAGGGTACCTTTAC CTCTGATTATAGCAAGTATCTGGA TTCTCGTCGTG-3' | 65 |
| GCG_lib123_rev | 5'-CTGTGCGGCCGCACCAGTX$_{13}$X$_{17}$CAGCCACTGAACA AAGTCTTGAGCACGTCT AGAATCC 3' | 66 |
| GCG_lib4_rev | 5'-CTGTGCGGCCGCACCAGTX$_{13}$X$_{17}$CAGCCACTGA ACGAAGTC X$_{15}$ X$_{11}$ X$_{12}$ X$_{12}$ X$_{19}$ X$_{14}$ X$_{16}$GTACTTGCTGTAGTCGCTGGTG-3' | 67 |
| GCG_lib5_rev | 5'-CTGTGCGGCCGCACTX$_{20}$X$_{13}$X$_{17}$X$_{16}$X$_{21}$X$_{15}$X$_{22}$ X$_{18}$X$_{14}$CTGAGCACGACGAGA GTCCAGATACTTG-3' | 68 |

SEQ ID NOs:61, 62, 63, 66, 67, and g8 may also be represented as shown in Table 4.

TABLE 4

Library Sequences

| SEQ ID NO: | Name | | Sequence |
|---|---|---|---|
| 61 | GCG_lib1_for | n12-14 wherein n$_{12}$n$_{13}$n$_{14}$ have the triplet sequences AAA, AAT, ACT, ATA, ATG, CAG, CAT, CCG, CGT, CTG, GAA, GAT, GCT, GGT, GTT, TAC, TCT, TGG, or TTT in which each triplet is each present 5.26% of the time n15-17 wherein n$_{15}$n$_{16}$n$_{17}$ have the triplet sequences AAA, AAT, ACT, ATA, ATG, CAG, CAT, CCG, CGT, CTG, GAA, GAT, GCT, GGT, GTT, TAC, TCT, TGG, or TTT in which each triplet is each present 5.26% of the time n18-20 wherein n$_{18}$n$_{19}$n$_{20}$ have the triplet sequence CAT present 45% percent of the time and the triplet sequences AAA, AAT, ACT, ATA, ATG, CAG, CCG, CGT, CTG, GAA, GAT, GCT, GGT, GTT, TAC, TCT, TGG, or TTT are each present 5.26% of the time n21-23 wherein n$_{21}$n$_{22}$n$_{23}$ have the triplet sequence TCT which present 45% percent of the time and the triplet sequences AAA, AAT, ACT, ATA, ATG, CAG, CAT, CCG, CGT, CTG, GAA, GAT, GCT, GGT, GTT, TAC, TGG, or TTT are each present 5.26% of the time n24-26 wherein n$_{24}$n$_{25}$n$_{26}$ have the triplet sequence CAG present 45% percent of the time and the triplet sequences AAA, AAT, ACT, ATA, ATG, CAT, CCG, CGT, CTG, GAA, GAT, GCT, GGT, GTT, TAC, TCT, TGG, or TTT are each present 5.26% of the time n27-29 wherein n$_{27}$n$_{28}$n$_{29}$ have the triplet sequence GGT present 45% percent of the time and the triplet sequences AAA, AAT, ACT, ATA, ATG, CAG, CAT, CCG, CGT, CTG, GAA, GAT, GCT, GTT, TAC, TCT, TGG, or TTT are each present 5.26% of the time n30-32 wherein n$_{30}$n$_{31}$n$_{32}$ have the triplet sequence ACT present 45% percent of the time and the triplet sequences AAA, AAT, ATA, ATG, CAG, CAT, CCG, CGT, CTG, GAA, GAT, GCT, GGT, GTT, TAC, TCT, TGG, or TTT are each present 5.26% of the time | GCCGGATGGCAnnnnnnnnnnnn nnnnnnnnTTTACCTCTGATTACA GCAAATACCTGGATTCTAGACGTG CTCAAGAC |
| 62 | GCG_lib2_for | n14-16 wherein n$_{14}$n$_{15}$n$_{16}$ have the triplet sequence CAT present 45% percent of the time and the triplet sequences AAA, AAT, ACT, ATA, ATG, CAG, CCG, CGT, CTG, GAA, GAT, GCT, GGT, GTT, TAC, TCT, TGG, or TTT are each present 5.26% of the time n17-19 wherein n$_{17}$n$_{18}$n$_{19}$ have the triplet sequence TCT present 45%percent of the time and the triplet sequences AAA, AAT, ACT, ATA, ATG, CAG, CCG, CGT, CTG, CAT, GAA, GAT, GCT, GGT, GTT, TAC, TGG, or TTT are each present 5.26% of the time n20-22 wherein n$_{20}$n$_{21}$n$_{22}$ have the triplet sequence CAG present 45% percent of the time and the triplet sequences AAA, AAT, ACT, ATA, ATG, CCG, CGT, CTG, CAT, GAA, GAT, GCT, GGT, GTT, TAC, TCT, TGG, or TTT | GCCGGCCATGGCAnnnnnnnnnn nnnnnnnnnTCTGATTACAGCAA ATACCTGGATTCTAGACGTGCTCA AGAC |

TABLE 4-continued

Library Sequences

| SEQ ID NO: | Name | Sequence |
|---|---|---|
| | are each present 5.26% of the time<br>n23-25 wherein $n_{23}n_{24}n_{25}$ have the triplet sequence GGT present 45% percent of the time and the triplet sequences AAA, AAT, ACT, ATA, ATG, CAG, CCG, CGT, CTG, CAT, GAA, GAT, GCT, GTT, TAC, TCT, TGG, or TTT are each present 5.26% of the time<br>n26-28 wherein $n_{26}n_{27}n_{28}$ have the triplet sequence ACT present 45% percent of the time and the triplet sequences AAA, AAT, ATA, ATG, CAG, CCG, CGT, CTG, CAT, GAA, GAT, GCT, GGT, GTT, TAC, TCT, TGG, or TTT are each present 5.26% of the time<br>n29-31 wherein $n_{29}n_{30}n_{31}$ have the triplet sequence TTT present 45% percent of the time and the triplet sequences AAA, AAT, ACT, ATA, ATG, CAG, CCG, CGT, CTG, CAT, GAA, GAT, GCT, GGT, GTT, TAC, TCT, OR TGG are each present 5.26% of the time<br>n32-34 wherein $n_{32}n_{33}n_{34}$ have the triplet sequence ACT present 45% percent of the time and the triplet sequences AAA, AAT, ATA, ATG, CAG, CCG, CGT, CTG, CAT, GAA, GAT, GCT, GGT, GTT, TAC, TCT, TGG, or TTT are each present 5.26% of the time | |
| 63 | GCG_lib3_for<br>n32-34 wherein $n_{32}n_{33}n_{34}$ have the triplet sequence ACT present 45% percent of the time and the triplet sequences AAA, AAT, ATA, ATG, CAG, CCG, CGT, CTG, CAT, GAA, GAT, GCT, GGT, GTT, TAC, TCT, TGG, or TTT are each present 5.26% of the time<br>n35-37 wherein $n_{35}n_{36}n_{37}$ have the triplet sequence percent of the time and the triplet sequences AAA, AAT, ACT, ATA, ATG, CAG, CCG, CGT, CTG, CAT, GAA, GAT, GCT, GGT, GTT, TAC, TGG, or TTT are each present 5.26% of the time<br>n38-40 wherein $n_{38}n_{39}n_{40}$ have the triplet sequence GAT present 45% percent of the time and the triplet sequences AAA, AAT, ACT, ATA, ATG, CAG, CCG, CGT, CTG, CAT, GAA, GCT, GGT, GTT, TAC, TCT, TGG, or TTT are each present 5.26% of the time<br>n41-43 wherein $n_{41}n_{42}n_{43}$ have the triplet sequence TAC present 45% percent of the time and the triplet sequences AAA, AAT, ACT, ATA, ATG, CAG, CCG, CGT, CTG, CAT, GAA, GAT, GCT, GGT, GTT, TCT, TGG, or TTT are each present 5.26% of the time<br>n44-46 wherein $n_{44}n_{45}n_{46}$ have the triplet sequence TCT present 45% percent of the time and the triplet sequences AAA, AAT, ACT, ATA, ATG, CAG, CCG, CGT, CTG, CAT, GAA, GAT, GCT, GGT, GTT, TAC, TGG, or TTT are each present 5.26% of the time<br>n47-49 wherein $n_{47}n_{48}n_{49}$ have the triplet sequence AAA present 45% percent of the time and the triplet sequences AAT, ACT, ATA, ATG, CAG, CCG, CGT, CTG, CAT, GAA, GAT, GCT, GGT, GTT, TAC, TCT, TGG, or TTT are each present 5.26% of the time<br>n50-52 wherein $n_{50}n_{51}n_{52}$ have the triplet sequence TAC present 45% percent of the time and the triplet sequences AAA, AAT, ACT, ATA, ATG, CAG, CCG, CGT, CTG, CAT, GAA, GAT, GCT, GGT, GTT, TCT, TGG, or TTT are each present 5.26% of the time | GCCGGCCATGGCACATTCTCAGGG TACCTTTnnnnnnnnnnnnnnnnnn nnnnCTGGATTCTAGACGTGCTCA AGAC |
| 66 | GCG_lib123_rev<br>n19-21 wherein $n_{19}n_{20}n_{21}$ have the triplet sequence GTT present 45% percent of the time and the triplet sequences TTT, CGT, AAT, CAT, CTG, ATG, CGG, TCT, CAG, TTC, ATC, TGC, ACC, AAC, ATA, ACT, CCA, or AAA are each present 5.26% of the time<br>n22-24 wherein $n_{22}n_{23}n_{24}$ have the triplet sequence CAT present 45% percent of the time and the triplet sequences TTT, GTT, CGT, AAT, CAT, CTG, ATG, CGG, TCT, CAG, TTC, ATC, TGC, ACC, AAC, ATA, ACT, CCA, or AAA are each present 5.26% of the time | CTGTGCGGCCGCACCAGTnnnnnn CAGCCACTGAACAAAGTCTTGAGC ACGTCT AGAATCC |
| 67 | GCG_lib4_rev<br>n19-21 wherein $n_{19}n_{20}n_{21}$ have the triplet sequence | CTGTGCGGCCGCACCAGTnnnnnn CAGCCACTGAACGAAGTCnnnnnn |

TABLE 4-continued

Library Sequences

| SEQ ID NO: | Name | | Sequence |
|---|---|---|---|
| | | GTT present 45% percent of the time and the triplet sequences TTT, CGT, AAT, CAT, CTG, ATG, CGG, TCT, CAG, TTC, ATC, TGC, ACC, AAC, ATA, ACT, CCA, or AAA are each present 5.26% of the time | nnnnnnnnnnnnnnnGTACTTGCT GTAGTCGCTGGTG |
| | | n22-24 wherein $n_{22}n_{23}n_{24}$ have the triplet sequence CAT present 45% percent of the time and the triplet sequences TTT, GTT, CGT, AAT, CTG, ATG, CGG, TCT, CAG, TTC, ATC, TGC, ACC, AAC, ATA, ACT, CCA, or AAA are each present 5.26% of the time | |
| | | n43-45 wherein $n_{43}n_{44}n_{45}$ have the triplet sequence CTG present 45% percent of the time and the triplet sequences TTT, GTT, CGT, AAT, CAT, ATG, CGG, TCT, CAG, TTC, ATC, TGC, ACC, AAC, ATA, ACT, CCA, or AAA are each present 5.26% of the time | |
| | | n46-48 wherein $n_{46}n_{47}n_{48}$ have the triplet sequence TGC present 45% percent of the time and the triplet sequences TTT, GTT, CGT, AAT, CAT, CTG, ATG, CGG, TCT, CAG, TTC, ATC, ACC, AAC, ATA, ACT, CCA, or AAA are each present 5.26% of the time | |
| | | n49-51 wherein $n_{49}n_{50}n_{51}$ have the triplet sequence TCT present 45% percent of the time and the triplet sequences TTT, GTT, CGT, AAT, CAT, CTG, ATG, CGG, CAG, TTC, ATC, TGC, ACC, AAC, ATA, ACT, CCA, or AAA are each present 5.26% of the time | |
| | | n52-54 wherein $n_{52}n_{53}n_{54}$ have the triplet sequence ACT present 45% percent of the time and the triplet sequences TTT, GTT, CGT, AAT, CAT, CTG, ATG, CGG, TCT, CAG, TTC, ATC, TGC, ACC, AAC, ATA, CCA, or AAA are each present 5.26% of the time | |
| | | n55-57 wherein $n_{55}n_{156}n_{57}$ have the triplet sequence ATC present 45% percent of the time and the triplet sequences TTT, GTT, CGT, AAT, CAT, CTG, ATG, CGG, TCT, CAG, TTC, ATC, TGC, ACC, AAC, ATA, ACT, CCA, or AAA are each present 5.26% of the time | |
| | | n58-60 wherein $n_{58}n_{59}n_{60}$ have the triplet sequence CAG present 45% percent of the time and the triplet sequences TTT, GTT, CGT, AAT, CAT, CTG, ATG, CGG, TCT, TTC, ATC, TGC, ACC, AAC, ATA, ACT, CCA, or AAA are each present 5.26% of the time | |
| 68 | GCG_lib5_rev | | CTGTGCGGCCGCACTnnnnnnnnn nnnnnnnnnnnnnnnnnnCTGAGC ACGACGAGAGTCCAGATACTTG |
| | | n16-18 wherein $n_{16}n_{17}n_{18}$ have the triplet sequence CGT present 45% percent of the time and the triplet sequences TTT, GTT, AAT, CAT, CTG, ATG, CGG, TCT, CAG, TTC, ATC, TGC, ACC, AAC, ATA, ACT, CCA, or AAA are each present 5.26% of the time | |
| | | n19-21 wherein $n_{19}n_{20}n_{21}$ have the triplet sequence GTT present 45% percent of the time and the triplet sequences TTT, CGT, AAT, CAT, CTG, ATG, CGG, TCT, CAG, TTC, ATC, TGC, ACC, AAC, ATA, ACT, CCA, or AAA are each present 5.26% of the time | |
| | | n22-24 wherein $n_{22}n_{23}n_{24}$ have the triplet sequence CAT present 45% percent of the time and the triplet sequences TTT, GTT, CGT, AAT, CTG, ATG, CGG, TCT, CAG, TTC, ATC, TGC, ACC, AAC, ATA, ACT, CCA, or AAA are each present 5.26% of the time | |
| | | n25-27 wherein $n_{25}n_{26}n_{27}$ have the triplet sequence CAG present 45% percent of the time and the triplet sequences TTT, GTT, CGT, AAT, CAT, CTG, ATG, CGG, TCT, TTC, ATC, TGC, ACC, AAC, ATA, ACT, CCA, or AAA are each present 5.26% of the time | |
| | | n28-30 wherein $n_{28}n_{29}n_{30}$ have the triplet sequence CCA present 45% percent of the time and the triplet sequences TTT, GTT, CGT, AAT, CAT, CTG, ATG, CGG, TCT, CAG, TTC, ATC, TGC, ACC, AAC, ATA, ACT, or AAA are each present 5.26% of the time | |
| | | n31-33 wherein $n_{31}n_{32}n_{33}$ have the triplet sequence CTG present 45% percent of the time and the triplet sequences TTT, GTT, CGT, AAT, CAT, ATG, CGG, TCT, CAG, TTC, ATC, TGC, ACC, AAC, ATA, ACT, CCA, or AAA are each present 5.26% of the time | |
| | | n34-36 wherein $n_{34}n_{35}n_{36}$ have the triplet sequence AAC present 45% percent of the time and the triplet sequences TTT, GTT, CGT, AAT, CAT, CTG, ATG, CGG, | |

TABLE 4-continued

Library Sequences

| SEQ ID NO: Name | Sequence |
|---|---|
| | TCT, CAG, TTC, ATC, TGC, ACC, ATA, ACT, CCA, or AAA are each present 5.26% of the time<br>n37-39 wherein $n_{37}n_{38}n_{39}$ have the triplet sequence AAA present 45% percent of the time and the triplet sequences TTT, GTT, CGT, AAT, CAT, CTG, ATG, CGG, TCT, CAG, TTC, ATC, TGC, ACC, AAC, ATA, ACT, or CCA are each present 5.26% of the time<br>n40-42 wherein $n_{40}n_{41}n_{42}$ have the triplet sequence ATC present 45% percent of the time and the triplet sequences TTT, GTT, CGT, AAT, CAT, CTG, ATG, CGG, TCT, CAG, TTC, TGC, ACC, AAC, ATA, ACT, CCA, or AAA are each present 5.26% of the time |

The single strand oligonucleotides were converted into double strand fragments by primer extension, combining the relative oligo forward (for) and reverse (rev) for each library. 600 pmol of oligo for and rev were denatured at 95° C. for 30 seconds, annealed at 65° C. for 30 seconds and extended in the presence of 0.2 mM dNTS and 1 unit of Phusion High-Fidelity DNA Polymerase (#F-530 Thermo Scientific) for 30 seconds at 72° C. as shown in FIG. 2.

Once checked on agarose gel, the fragments were digested with NcoI-NotI (NcoI #R0193S and NotI #R0189L Bio Labs), purified through Qiaquick nucleotide Removal Kit (Qiagen), quantified by $OD_{260}$ and ligated into NcoI-NotI pCANTAB6 phagemid. Preparative ligations were assembled by mixing vector and inserts at 1:5 molar ratio and incubated overnight at 16° C. with T4 DNA ligase (M02024 Bio Labs). The ligation product was desalted and transformed to the electrocompetent E. Coli XL1Blue cells (Agilent Technologies) using an electroporator (Bio-Rad, Hercules, Calif.) at 1.8 kV, 25 µF and 200Ω. Transformed bacteria were plated on 23×23 2XTY/Amp (100 µg/ml)/2% Glucose square plates and incubated o/n at 37° C.

The day after the plates were scraped to harvest bacteria in 10 ml 2XTY Amp (100 µg/ml)/2% Glucose containing 17% glycerol and stored at −80° C. For each library $6 \times 10^7$ individual clones were collected for a total complexity of $3 \times 10^8$ for the five sub-libraries. Phage libraries were prepared by super-infection of transformed bacteria with 10 multiplicity of Infection (MOI) of M13K07 helper phage, purified through CsCl gradient, according to standard protocols, and titrated. The library mix was prepared mixing equivalent amount of phages from each sub-library.

Selection of GCG/GLP1 Co Agonists from Phage Libraries

About $10^{11}$ phages of the library were used for the first round of selection on HEK293 glucagon receptor (GCGr) and GLP1 receptor (GLP1r) cells, after depletion on HEK293 naïve cells. Four rounds of selection were carried out on cells, where two different selection scheme (M10 and M20) were followed, alternating rounds of selection on the two different cell lines: in the selection scheme M10 the first round was made on HEK293 GCGr cells, while in the selection scheme M20 the first round was made on HEK293 GLP1r.

Briefly phage particles were blocked in 0.5 ml PBS containing 3% non-fat dry milk (MPBS) for 30 min at room temperature (RT), then incubated with $10^7$ HEK293 wild type cells previously resuspended in MPBS for 1 additional hour in a rotary mixer. HEK293 cells were pelleted, the depleted phage supernatant was recovered, then incubated with either HEK293 GLP1r or HEK293 GCGr resuspended into 0.5 ml of MPBS for 1 hr in a rotary mixer.

After incubation, the mixture of cells and phages was centrifuged 1 minute at 2000 rpm, the supernatant was discarded, and pellet was washed 6 times with 1×PBS. For the elution the pellet was resuspended in 100 mM HCl (500 µl) for 15 minutes at RT in agitation then neutralized with 100 mM TrisHCl pH 7.5. Eluted phages were transferred in 50 mL Falcon tube, 10 mL of TG1 cells were added and the mixture was incubated for 1 hr 37° C. 150 rpm. TG1 infected cells were plated out onto 2XTY Amp/Glu bioassay plate and incubated overnight at 30° C. The day after the selected pool of phages was rescued by scraping bacteria from bioassay plate in 10 mL of 2× TY Amp/Glu. 50 µL of the scraping was inoculated in 50 mL 2× TY Amp/Glu and grown at 37° C. to OD600 nm=0.5 in a shaker at 250 rpm. M13K07 helper phage was added to bacteria at 10 MOI, incubated 30 min 37° C. in static and 30 min 37° C. in agitation (120 rpm). The culture was centrifuged 10 minutes 3200 rpm, supernatant was removed, pellet was resuspended in 50 ml 2XTY Amp (100 µg/mL)/Kan (25 µg/mL) and grown overnight at 25° C. 250 rpm. The day after culture was centrifuged 45 minutes 4° C. 4200 rpm, the supernatant was recovered and used to perform the following selection round.

Screening by cAMP Activity Assay

Each round of selection was screened by activity assay both as pool and as single clone phage supernatant. From each round of selection about 200 single clones were isolated and prepared as 96 well supernatants. Phages were then precipitated from the supernatants by adding ⅓ volume of 20% PEG8000/2.5M NaCl overnight, centrifuged at 4200 rpm 4° C. for 45 minutes, and resuspended in 1/10 volume of PBS1X. Phage pool and single phages were tested by using cAMP activity assay (HitHunter cAMP XS+ Assay DiscoverX 90-0075), following manufacture instruction. HEK293 GCGr and HEK293 GLP1r stable cell lines Doxy-induced and not induced were harvested and counted and re-suspended in Assay Buffer (7.5% BSA, 10% FBS, PBS1X+ R01724 phosphatase inhibitor). Eight µL of each phage supernatant was diluted 1:5 into Assay Buffer (7.5% BSA, 10% FBS, PBS1X+R01724 phosphatase inhibitor) and incubated 3 hours at room temperature with 30.000 cells/well resuspended in Assay Buffer. The specific activity was detected in luminescence with Safire2 TECAN instrument. Phages able to co-activate GCGr and GLP1r were isolated, phagemids were extracted and subjected to DNA sequencing. Peptides corresponding to the identified sequences were synthesized and further tested.

EXAMPLE 2

Peptides corresponding to the identified sequences were synthesized and are shown in Table 5.

TABLE 5

| SEQ ID NO: | Name | Sequence |
|---|---|---|
| 1 | PD17 | HSVGNFWSDYSKYLDSRRAQDFVQWLMLT-CONH$_2$ |
| 2 | PD18 | HSQGTFTSDYSKYVEDRRAHDFVQWLMNT-CONH$_2$ |
| 3 | PD19 | HSQGTFTSDYRKYLDERAAWDFVQWLMNT-CONH$_2$ |
| 4 | PD20 | HSQGTFTSDYSKYLNSWMTQDFVQWLMNT-CONH$_2$ |
| 5 | PD21 | HSQGTFTSDYSKYLDIGRAQDFVQWLLNT-CONH$_2$ |
| 6 | PD22 | HSQGTFTSDYSKYLDSLMAQDFVQWLMST-CONH$_2$ |
| 7 | PD23 | HSQGTFTSDYSKYLDWRRAQDFVQWLLNT-CONH$_2$ |
| 8 | PD24 | HSQGTFTSDYIKLLDSRRAQDFVQWLMNT-CONH$_2$ |
| 9 | PD25 | HSQGTFTSDYSKYLDARRAQDFVQWLIRT-CONH$_2$ |
| 10 | PD26 | HSQGTFTSDYSKYLDVRRAQDFVQWLMNT-CONH$_2$ |
| 11 | PD27 | HSQGTFTSDYSKYLDELRAYDFVQWLMNT-CONH$_2$ |
| 12 | PD28 | HSQGTFTSDYSKYLDYMRAYDFVQWLMNT-CONH$_2$ |
| 13 | PD29 | HSQGTFTSDYSKYLDSRRAHDFVQWLLNT-CONH$_2$ |
| 14 | PD30 | HSQGTFTSDYSKYLDSRRAQDFVQWLMNP-CONH$_2$ |
| 15 | PD31 | HSQGTFTSDYSKYLDSRRAQDFVQWLINY-CONH$_2$ |
| 16 | PD32 | INHEQWAFTSDYSKYLDSRRAQDFVQWLMNT-CONH$_2$ |
| 17 | PD33 | ASMFTFFSDYSKYLDSRRAQDFVQWLMLT-CONH$_2$ |
| 18 | PD34 | HSQGTFLSDYSKLLDSRRAQDFVQWLMQT-CONH$_2$ |
| 19 | PD35 | HSQGTFLHDYYYYLDSRRAQDFVQWLMDT-CONH$_2$ |
| 20 | PD36 | HSQGTFTSDYSKYLDSIRAQDFVQWLMDT-CONH$_2$ |
| 21 | PD37 | HSQGTFTSDYSKYLDNKRAQDFVQWLMQT-CONH$_2$ |
| 22 | PD38 | HSQGTFTSDYSKYLDSRRAQDFVDWLMNE-CONH$_2$ |
| 23 | PD39 | HSQGTFTSDYSKYLDSRRAQEFVEWLMDE-CONH$_2$ |
| 24 | PD40 | HSQGTFTSDYSKYLDSRRAQDFVQWLINT-CONH$_2$ |
| 25 | PD41 | KALGQFTFTSDYSKYLDSRRAQDFVQWLMNT-CONH$_2$ |
| 26 | PD42 | HSQGTFFHDYSKYLDSRRAQDFVQWLLNT-CONH$_2$ |
| 27 | PD43 | HSQGTFFSDYSHWLDSRRAQDFVQWLMNT-CONH$_2$ |
| 28 | PD44 | HSQGTFTSDYSKYLDWRRAQDFVQWLQNT-CONH$_2$ |
| 29 | PD45 | HSQGTFTSDYSKYLDSKRAHDFVQWLLNT-CONH$_2$ |
| 30 | PD46 | HSQGTFTSDYSKYLDSRRAQDFWIDLMNT-CONH$_2$ |
| 31 | PD47 | HSQGTFTSDYSKYLDSRRAQDFVMTSMNT-CONH$_2$ |
| 32 | PD48 | HSQGTFTSDYSKYLDSRRAQDFVDWLLNA-CONH$_2$ |
| 33 | PD49 | HSQGTFTSDYSKYLDSRRAQDFVEWLMNN-CONH$_2$ |
| 34 | PD50 | HSQGTFTSDYSKYLDSRRAQDFVDWLINS-CONH$_2$ |
| 35 | PD51 | HSHGTFTSDYSKYLDSRRAQDFVQWLMTT-CONH$_2$ |
| 36 | PD52 | HSQGIFFSDYSKYLDSRRAQDFVQWLMNT-CONH$_2$ |
| 37 | PD53 | HSQGTFLSDYSKYLDSRRAQDFVQWLMNT-CONH$_2$ |
| 38 | PD54 | HSQGTFTSDYSWYLDSRRAQDFVQWLMNT-CONH$_2$ |
| 39 | PD55 | HSQGTFTSDYSKYLDMQRAHDFVQWLMNT-CONH$_2$ |
| 40 | PD56 | HSQGTFTSDYSKYLDSRMAYDFVQWLMNT-CONH$_2$ |
| 41 | PD57 | HSQGTFTSDYSKYLDSRRAQDFVQWLLNQ-CONH$_2$ |
| 42 | PD58 | HSQGTFFSDYSKYLDSRRAQDFVQWLLET-CONH$_2$ |
| 43 | PD59 | HSQGTFTSDYSKYLDSRRAQDFVQWLLDS-CONH$_2$ |

CONH$_2$ indicates that the carboxy terminus of the C-terminal peptide is amidated.

Selected peptides from Table 5 were synthesized as modified peptides that included lipidation and insertion of non-natural amino acids. These peptides are shown in Table 6.

TABLE 6

| SEQ ID NO: | Name | Sequence |
|---|---|---|
| 44 | TP534 | HsQGTFTSDK(γEγEC16)SKYLDNKRAQDFVQWLMQT-CONH$_2$ |
| 45 | TP535 | HsQGTFTSDK(γEγEC16)SKYLDSRRAHDFVQWLLNT-CONH$_2$ |
| 46 | TP536 | HsQGTFLSDK(γEγEC16)SKLLDSRRAQDFVQWLMQT-CONH$_2$ |
| 47 | TP552 | HsQGTFLSDYSKLLDSRAAQDFVQWLLQT-CONH$_2$ |
| 48 | TP559 | HsQGTFTSDK(γEγEC16)SKYLDARAAHDFVQWLLNT-CONH$_2$ |
| 49 | TP572 | HUQGTFTSDK(γEγEC16)SKYLDSRRAHDFVQWLLNTKγE-CONH$_2$ |
| 50 | TP573 | HUQGTFTSDK(γEγEC16)SKYLDARAAHDFVQWLLNTKγE-CONH$_2$ |
| 51 | TP574 | HUQGTFTSDK(γEγEC16)SKYLDNKRAQDFVQWLMQTKγE-CONH$_2$ |

U = aminoisobutyric acid; s = D-Ser; γE = γ-glutamic acid; C16 = —CO—(CH$_2$)$_{14}$—CH$_3$
CONH$_2$ indicates that the carboxy terminus of the C-terminal peptide is amidated.

General Synthetic Procedure for Synthesizing the Peptides Shown in Table 5 and Table 6.

Peptides SEQ ID NOs:1-48 were synthesized on a Rink-amide PEG-PS resin, Champion (Biosearch Technologies (150 μmol scale, loading 0.28 mmol/g) on a Symphony Protein Technologies Inc. synthesizer. The amino acids were dissolved at a 0.3 M concentration in DMF and activated with equimolar amounts of HATU (O-(7-azabenzotriazol-1-yl)-N,N,N',N'-tetramethyluronium hexafluorophosphate) and a 2-fold molar excess of DIEA (diisopropylethylamine) solution 2 M in NMP. The acylation reactions were performed for 1 hour with 5-fold excess of activated amino acid over the resin free amino groups; double acylation reactions of 45 minutes were performed from amino acid position 1 to amino acid position 7 and from Phe$_{22}$ to Val$_{23}$.

Peptides SEQ ID NOs:49-51 were synthesized on a Liberty Blue microwave synthesizer (CEM). The amino acids were dissolved at a 0.2 M concentration in DMF and activated with equimolar amounts of diisopropylcarbodiimide (0.5 M solution) and Oxyma (1 M solution). Both acylation and deprotection cycles were done using microwave heating using standard protocols provided by CEM. Namely the acylation reactions were performed for 2.5 minutes by microwave heating at 90° C. with 5-fold excess of activated amino acid over the resin free amino groups; for Arg and His acylations double acylation reactions were performed for 10 minutes by microwave heating at 50° C. From amino acid at position 1 to amino acid at position 7 and for the Phe-Val residues double acylation reactions were performed for 5 minutes by microwave heating at 90° C. The deprotection step was performed by microwave heating at 90° C. for 1.5 minutes using 20% piperidine solution in DMF.

For all the synthesis, the amino acids side chain protecting groups were: tert-butyl for Asp, Glu, Ser, D-Ser, Thr and Tyr; trityl for Asn, Gln and His; tert-butoxy-carbonyl for Lys, Trp; 2,2,4,6,7-pentamethyldihydrobenzofuran-5-sulfonyl for Arg. For seq ID 49, 50, 51, the C-terminal amino acid γ-glutamic acid was incorporated as Fmoc-Glu-OtBu. For peptide SEQ ID NOs:44, 45, 46, 47, 48, 49, 50, and 51 the N-terminal residue was incorporated as Boc-His(Trt)-OH.

For peptide SEQ ID NOs: 44, 45, 46, 49, 50, and 51, the lysine at position 10 was incorporated with a Dde [1-(4,4-dimethyl-2,6-dioxocyclohex-1-ylidene)ethyl] protecting group on the side chain amino group. At the end of the assembly, the Dde protecting group of Lys(Dde) was removed by treatment of 2% hydrazine in DMF. The side chain of Lys was derivatized by incorporation of two Fmoc-Glu-OtBu (γ-glutamic acid) residues and palmitic acid using HOAt and DIC as activators.

The dry peptide-resins were treated for two hours at room temperature with 88% TFA, 5% phenol, 2% triisopropylsilane and 5% water to afford protecting groups deprotection and cleavage from resin. The solution was filtered to remove the resin and the crude peptide solution was precipitated in cold methyl tert-butyl ether. The peptide pellet was resuspended, washed and centrifuged in cold methyl tert-butyl ether for two times. The peptide pellet was dried under vacuum and then resuspended in H$_2$O, 20% acetonitrile, and lyophilized.

The crude peptides (140 mg in 3 mL of DMSO) were purified by reverse-phase HPLC using preparative Waters) (Bridge C18 (50×150 mm, 5 µm, 100 Å) and using as eluents (A) 0.1% TFA in water and (B) 0.1% TFA in acetonitrile.

Analytical HPLC was performed on a Acquity UPLC Waters Chromatograph with a BEH130 C18 or BEH300 C4 Acquity Waters 2.1×100 mm, 1.7 µm, at 45° C., using H$_2$O, 0.1% TFA (A) and CH3CN, 0.1% TFA (B) as solvents. The peptides were characterized by electrospray mass spectrometry on an Acquity SQ Detector.

EXAMPLE 3

Activity of the peptides at the Glucagon receptor (GCGR) and GLP-1 receptor (GLP1R) was measured in a cAMP activity assay.

Peptides were dissolved in 100% DMSO and serially diluted to generate 10 point titrations. The peptide solutions were then transferred into 384-well assay plates (150 nL/well). Assay ready frozen cells expressing human GLP1R or human GCGR were suspended in growth media consisting of DMEM medium (GIBCO), 10% FBS (GIBCO), 1×NEAA(GIBCO), 1× P/S (GIBCO), 10 ug/ml Blasticidin (GIBCO) and 200 µg/mL Hygromycin (GIBCO). Cells were then diluted in assay buffer consisting of PBS (GIBCO), 7.5% BSA (Perkin Elmer), 100 µM RO 20-1724 (Sigma), with or without 20% human serum (MP Biomedical). The cell suspensions (15 µL) were then added to the assay plates containing the peptide solutions (30,000 cells/well for human GCGR; 10,000 cells/well for human GLP1R). The cells were incubated for 1 hour at room temperature in the dark. Production of cAMP was determined using HitHunter™ cAMPXS kits (DiscoverX) following manufacturer protocol. The plates were incubated for overnight at room temperature in the dark. Luminescence was measured using an EnVision Multilabel plate reader (Perkin Elmer). Native GLP-1 and Glucagon (Bachem) are used as control peptides. EC$_{50}$ values were calculated using uses a 4 parameter logistic fit based on the Levenberg-Marquardt algorithm. The EC$_{50}$ results are shown in Table 2 and Table 7.

EXAMPLE 4

In this example, the EC$_{50}$ activity and balance of the five peptides from Table 6 that included d-Ser at position 2 and Lys(γEγEC16 at position 10) were compared to their respective non-derivatized parental peptides. As shown, the lipidated analogs retained their parental peptide potency at the GCG and/or GLP-1 receptor and retained the relative balance displayed by the parent peptide.

TABLE 7

| SEQ ID NO: | Name | Sequence | EC$_{50}$ hGCGR | EC$_{50}$ hGLP1 | Ratio |
|---|---|---|---|---|---|
| 13 | PD29 | HSQGTFTSDYSKYLDSRRAH DFVQWLLNT-CONH$_2$ | 0.02 | 0.02 | 1 |
| 45 | TP535 | HsQGTFTSDK(γEγEC16) SKYLDSRRAHDFVQWLLNT-CONH$_2$ | 0.02 | 0.05 | 0.4 |
| 48 | TP559 | HsQGTFTSDK(γEγEC16) SKYLDARAAHDFVQWLLNT-CONH$_2$ | 0.02 | 0.05 | 0.4 |
| 18 | PD34 | HSQGTFLSDYSKLLDSRAAQ DFVQWLLQT-CONH$_2$ | 0.09 | >5 | <0.018 |
| 47 | TP552 | HsQGTFLSDYSKLLDSRAAQ DFVQWLLQT-CONH$_2$ | 0.02 | 5.000 | 0.004 |
| 46 | TP536 | HsQGTFLSDK(γEγEC16) SKLLDSRAAQDFVQWLLQT-CONH$_2$ | 0.04 | 5.00 | 0.008 |
| 21 | PD37 | HSQGTFTSDYSKYLDNKRAQ DFVQWLMQT-CONH$_2$ | 0.16 | 0.05 | 3.2 |
| 44 | TP534 | HsQGTFTSDK(γEγEC16) SKYLDNKRAQDFVQWLMQT-CONH$_2$ | 0.01 | 0.02 | 0.5 |

U = aminoisobutyric acid; s = D-Ser; γE = γ-glutamic acid; C16 = —CO—(CH$_2$)$_{15}$
CONH$_2$ indicates that the carboxy terminus of the C-terminal peptide is amidated.

REFERENCES

1. Sadry S A, Drucker D J. Emerging combinatorial hormone therapies for the treatment of obesity and T2DM. *Nat. Rev. Endocrinol.* 2013; 9: 425-33.

2. Hoist J J, Vilsboll T. Combining GLP-1 receptor agonists with insulin: therapeutic rationales and clinical findings. *Diabetes Obes Metab* 2013; 15: 3-14.
3. Roth J D, Roland B L, Cole R L, Trevaskis J L, Weyer C, Koda J E, Anderson C M, Parkes D G, Baron A D. Leptin responsiveness restored by amylin agonism in diet-induced obesity: evidence from nonclinical and clinical studies. *Proc Natl Acad Sci USA* 2008; 105: 7257-62.
4. Pan C Q, Buxton J M, Yung S L, Tom I, Yang L, Chen H, MacDougall M, Bell A, Claus T H, Clairmont K B, Whelan J P. Design of a long acting peptide functioning as both a glucagon-like peptide-1 receptor agonist and a glucagon receptor antagonist *J. Biol. Chem.* 2006; 281: 12506-15.
5. Dalbøge L S, Almholt D L C, Neerup T S R, Vrang N, Jelsing J, Fosgerau K. The Novel GLP-1-Gastrin Dual Agonist ZP3022 Improves Glucose Homeostasis and Increases β-Cell Mass without Affecting Islet Number in db/db Mice. *J. Pharmacol. Exp. Ther.* 2014; 350: 353-360.
6. Fosgerau K, Jessen L, Lind Tolborg J, Osterlund T, Schaeffer Larsen K, Rolsted K, Brorson M, Jelsing J, Skovlund Ryge Neerup T. The novel GLP-1-gastrin dual agonist, ZP3022, increases beta-cell mass and prevents diabetes in db/db mice. *Diabetes Obes. Metab.* 2013; 15: 62-71.
7. Day J W, Ottaway N, Patterson J T, Gelfanov V, Smiley D, Gidda J, Findeisen H, Bruemmer D, Drucker D J, Chaudhary N, Holland J, Hembree J, Abplanalp W, Grant E, Ruehl J, Wilson H, Kirchner H, Lockie S H, Hofmann S, Woods S C, Nogueiras R, Pfluger P T, Perez-Tilve D, DiMarchi R, Tschop M H. A new glucagon and GLP-1 co-agonist eliminates obesity in rodents. *Nat. Chem. Biol.* 2009; 5: 749-57.
8. Finan B, Ma T, Ottaway N, Müller T D, Habegger K M, Heppner K M, Kirchner H, Holland J, Hembree J, Raver C, Lockie S H, Smiley D L, Gelfanov V, Yang B, Hofmann S, Bruemmer D, Drucker D J, Pfluger P T, Perez-Tilve D, Gidda J, Vignati L, Zhang L, Hauptman J B, Lau M, Brecheisen M, Uhles S, Riboulet W, Hainaut E, Sebokova E, Conde-Knape K, Konkar A, DiMarchi R D, Tschop M H. Unimolecular Dual Incretins Maximize Metabolic Benefits in Rodents, Monkeys, and Humans. *Sci. Transl. Med.* 2013; 5: 209ra151.
9. Pocai A, Carrington P E, Adams J R, Wright M, Eiermann G, Zhu L, Du X, Petrov A, Lassman M E, Jiang G, Liu F, Miller C, Tota L M, Zhou G, Zhang X, Sountis M M, Santoprete A, Capito E, Chicchi G G, Thornberry N, Bianchi E, Pessi A, Marsh D J, SinhaRoy R. Glucagon-like peptide 1/glucagon receptor dual agonism reverses obesity in mice. *Diabetes* 2009; 58: 2258-66.
10. Day J W, Gelfanov V, Smiley D, Carrington P E, Eiermann G, Chicchi G, Erion M D, Gidda J, Thornberry N A, Tschop M H, Marsh D J, SinhaRoy R, DiMarchi R, Pocai A. Optimization of co-agonism at GLP-1 and glucagon receptors to safely maximize weight reduction in DIO-rodents. *J. Pept. Sci.* 2012; 98: 443-450.
11. Finan B, Yang B, Ottaway N, Smiley D L, Ma T, Clemmensen C, Chabenne J, Zhang L, Habegger K M, Fischer K, Campbell J E, Sandoval D, Seeley R J, Bleicher K, Uhles S, Riboulet W, Funk J, Hertel C, Belli S, Sebokova E, Conde-Knape K, Konkar A, Drucker D J, Gelfanov V, Pfluger P T, Muller T D, Perez-Tilve D, DiMarchi R D, Tschop M R. A rationally designed monomeric peptide triagonist corrects obesity and diabetes in rodents. *Nat. Med.* 2015; 21: 27-36.
12. Clemmensen C, Chabenne J, Finan B, Sullivan L, Fischer K, Küchler D, Sehrer L, Ograjsek T, Hofmann S, Schriever S S, Pfluger P T, Pinkstaff J, Tschop M H, DiMarchi R, Müller T D. GLP-1/glucagon co-agonism restores leptin responsiveness in obese mice chronically maintained on an obesogenic diet *Diabetes* 2013.
13. Bhat V K, Kerr B D, Flatt P R, Gault V A. A novel GIP-oxyntomodulin hybrid peptide acting through GIP, glucagon and GLP-1 receptors exhibits weight reducing and anti-diabetic properties. *Biochem. Pharmacol.* 2013; 85: 1655-1662.
14. Gault V A, Bhat V K, Irwin N, Flatt P R. A Novel Glucagon-like Peptide-1 (GLP-1)/Glucagon Hybrid Peptide with Triple-acting Agonist Activity at Glucose-dependent Insulinotropic Polypeptide, GLP-1, and Glucagon Receptors and Therapeutic Potential in High Fat-fed Mice. *J. Biol. Chem.* 2013; 288: 35581-35591.
15. Santoprete A, Capito E, Carrington P E, Pocai A, Finotto M, Langella A, Ingallinella P, Zytko K, Bufali S, Cianetti S, Veneziano M, Bonelli F, Zhu L, Monteagudo E, Marsh D J, Sinharoy R, Bianchi E, Pessi A. DPP-IV-resistant, long-acting oxyntomodulin derivatives. *J. Pept. Sci.* 2011; 17: 270-80.
16. Hamzeh-Mivehroud M, Alizadeh A A, Morris M B, Bret Church W, Dastmalchi S. Phage display as a technology delivering on the promise of peptide drug discovery. *Drug Discov. Today* 2013; 18: 1144-1157.
17. Smith G P, Petrenko V A. Phage Display. *Chem. Rev.* 1997; 97: 391-410.
18. Sidhu S S, Lowman H B, Cunningham B C, Wells J A. Phage display for selection of novel binding peptides. *Methods Enzymol.* 2000; 328: 333-63.
19. Cortese R, Monaci P, Nicosia A, Luzzago A, Felici F, Galfre G, Pessi A, Tramontano A, Sollazzo M. Identification of biologically active peptides using random libraries displayed on phage. *Curr. Opin. Biotechnol.* 1995; 6: 73-80.
20. O'Neil K T, Hoess R H, Jackson S A, Ramachandran N S, Mousa S A, DeGrado W F. Identification of novel peptide antagonists for GPIIb/IIIa from a conformationally constrained phage peptide library. *Proteins* 1992; 14: 509-15.
21. Koivunen E, Gay D A, Ruoslahti E. Selection of peptides binding to the alpha 5 beta 1 integrin from phage display library. *J. Biol. Chem.* 1993; 268: 20205-10.
22. Binetruy-Tournaire R, Demangel C, Malavaud B, Vassy R, Rouyre S, Kraemer M, Plouet J, Derbin C, Perret G, Mazie J C. Identification of a peptide blocking vascular endothelial growth factor (VEGF)-mediated angiogenesis. *EMBO J.* 2000; 19: 1525-33.
23. Szardenings M, Tornroth S, Mutulis F, Muceniece R, Keinanen K, Kuusinen A, Wikberg J E. Phage display selection on whole cells yields a peptide specific for melanocortin receptor 1. J. Biol. Chem. 1997; 272: 27943-8.
24. Rousch M, Lutgerink J T, Coote J, de Bruine A, Arends J W, Hoogenboom H R. Somatostatin displayed on filamentous phage as a receptor-specific agonist *Br. J. Pharmacol.* 1998; 125: 5-16.
25. Bikkavilli R K, Tsang S Y, Tang W M, Sun J X, Ngai S M, Lee S S, Ko W H, Wise H, Cheung W T. Identification and characterization of surrogate peptide ligand for orphan G protein-coupled receptor mas using phage-displayed peptide library. *Biochem. Pharmacol.* 2006; 71: 319-37.

26. Yin X, Ma Y, Liu M, Gao W, Wei D. Screening of a phage display library of exendin-4 mutants with the extracellular domain of rat GLP-1 receptor. *Protein Pept. Lett.* 2007; 14: 816-21.
27. Chen J, Bai G, Yang Y, Geng P, Cao Y, Zhu Y. Identifying glucagon-like peptide-1 mimetics using a novel functional reporter gene high-throughput screening assay. *Peptides* 2007; 28: 928-934.
28. Koth C M, Murray J M, Mukund S, Madjidi A, Minn A, Clarke H J, Wong T, Chiang V, Luis E, Estevez A, Rondon J, Zhang Y, Hötzel I, Allan B B. Molecular basis for negative regulation of the glucagon receptor. *Proc. Nat. Acad. Sci. U.S.A.* 2012; 109: 14393-14398.
29. Schwyzer R. Estimated conformation, orientation, and accumulation of dynorphin A-(1-13)-tridecapeptide on the surface of neutral lipid membranes. *Biochemistry* 1986; 25: 4281-6.
30. Schwyzer R. Membrane-assisted molecular mechanism of neurokinin receptor subtype selection. *EMBO J.* 1987; 6: 2255-9.
31. Schwyzer R. 100 years lock-and-key concept: are peptide keys shaped and guided to their receptors by the target cell membrane? *Biopolymers* 1995; 37: 5-16.
32. Siu F Y, He M, de Graaf C, Han G W, Yang D, Zhang Z, Zhou C, Xu Q, Wacker D, Joseph J S, Liu W, Lau J, Cherezov V, Katritch V, Wang M W, Stevens R C. Structure of the human glucagon class B G-protein-coupled receptor. *Nature* 2013; 499: 444-449.
33. Underwood C R, Garibay P, Knudsen L B, Hastrup S, Peters G H, Rudolph R, Reedtz-Runge S. Crystal Structure of Glucagon-like Peptide-1 in Complex with the Extracellular Domain of the Glucagon-like Peptide-1 Receptor. *J. Biol. Chem.* 2010; 285: 723-730.
34. Yagodkin A, Azhayev A, Roivainen J, Antopolsky M, Kayushin A, Korosteleva M, Miroshnikov A, Randolph J, Mackie H. Improved synthesis of trinucleotide phosphoramidites and generation of randomized oligonucleotide libraries. *Nucleos. Nucleot. Nucl. Ac.* 2007; 26: 473-97.
35. Gao Z, Tang Y, Chen J, Bai R, Zhang Q, Hou Y, Lu Y, Bai G. A novel DPP-IV-resistant analog of glucagon-like peptide-1 (GLP-1): KGLP-1 alone or in combination with long-acting PLGA microspheres. *Peptides* 2009; 30: 1874-81.
36. Harikumar K G, Wootten D, Pinon D I, Koole C, Ball A M, Furness S G B, Graham B, Dong M, Christopoulos A, Miller L J, Sexton P M. Glucagon-like peptide-1 receptor dimerization differentially regulates agonist signaling but does not affect small molecule allostery. *Proc. Nat. Acad. Sci. U.S.A.* 2012; 109: 18607-18612.
37. Roed S N, Nøhr A C, Wismann P, Iversen H, Bräuner-Osborne H, Knudsen S M, Waldhoer M. Functional Consequences of Glucagon-like Peptide-1 Receptor Cross-talk and Trafficking. *J. Biol. Chem.* 2015; 290: 1233-1243.
38. Jonas K C, Fanelli F, Huhtaniemi I T, Hanyaloglu A C. Single Molecule Analysis of Functionally Asymmetric G Protein-coupled Receptor (GPCR) Oligomers Reveals Diverse Spatial and Structural Assemblies. *J. Biol. Chem.* 2015; 290: 3875-3892.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

SEQUENCE LISTING

```
<160> NUMBER OF SEQ ID NOS: 68

<210> SEQ ID NO 1
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 1

His Ser Val Gly Asn Phe Trp Ser Asp Tyr Ser Lys Tyr Leu Asp Ser
1               5                   10                  15

Arg Arg Ala Gln Asp Phe Val Gln Trp Leu Met Leu Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 2
```

His Ser Gln Gly Thr Phe Thr Ser Asp Tyr Ser Lys Tyr Val Glu Asp
1               5                   10                  15

Arg Arg Ala His Asp Phe Val Gln Trp Leu Met Asn Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 3

His Ser Gln Gly Thr Phe Thr Ser Asp Tyr Arg Lys Tyr Leu Asp Glu
1               5                   10                  15

Arg Ala Ala Trp Asp Phe Val Gln Trp Leu Met Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 4

His Ser Gln Gly Thr Phe Thr Ser Asp Tyr Ser Lys Tyr Leu Asn Ser
1               5                   10                  15

Trp Met Thr Gln Asp Phe Val Gln Trp Leu Met Asn Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 5

His Ser Gln Gly Thr Phe Thr Ser Asp Tyr Ser Lys Tyr Leu Asp Ile
1               5                   10                  15

Gly Arg Ala Gln Asp Phe Val Gln Trp Leu Leu Asn Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 6

His Ser Gln Gly Thr Phe Thr Ser Asp Tyr Ser Lys Tyr Leu Asp Ser
1               5                   10                  15

Leu Met Ala Gln Asp Phe Val Gln Trp Leu Met Ser Thr
            20                  25

<210> SEQ ID NO 7
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 7

His Ser Gln Gly Thr Phe Thr Ser Asp Tyr Ser Lys Tyr Leu Asp Trp
1               5                   10                  15

Arg Arg Ala Gln Asp Phe Val Gln Trp Leu Leu Asn Thr
            20                  25

<210> SEQ ID NO 8
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 8

His Ser Gln Gly Thr Phe Thr Ser Asp Tyr Ile Lys Leu Leu Asp Ser
1               5                   10                  15

Arg Arg Ala Gln Asp Phe Val Gln Trp Leu Met Asn Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 9

His Ser Gln Gly Thr Phe Thr Ser Asp Tyr Ser Lys Tyr Leu Asp Ala
1               5                   10                  15

Arg Arg Ala Gln Asp Phe Val Gln Trp Leu Ile Arg Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

```
<400> SEQUENCE: 10

His Ser Gln Gly Thr Phe Thr Ser Asp Tyr Ser Lys Tyr Leu Asp Val
1               5                   10                  15

Arg Arg Ala Gln Asp Phe Val Gln Trp Leu Met Asn Thr
            20                  25

<210> SEQ ID NO 11
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 11

His Ser Gln Gly Thr Phe Thr Ser Asp Tyr Ser Lys Tyr Leu Asp Glu
1               5                   10                  15

Leu Arg Ala Tyr Asp Phe Val Gln Trp Leu Met Asn Thr
            20                  25

<210> SEQ ID NO 12
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 12

His Ser Gln Gly Thr Phe Thr Ser Asp Tyr Ser Lys Tyr Leu Asp Tyr
1               5                   10                  15

Met Arg Ala Tyr Asp Phe Val Gln Trp Leu Met Asn Thr
            20                  25

<210> SEQ ID NO 13
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 13

His Ser Gln Gly Thr Phe Thr Ser Asp Tyr Ser Lys Tyr Leu Asp Ser
1               5                   10                  15

Arg Arg Ala His Asp Phe Val Gln Trp Leu Leu Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide
```

```
<400> SEQUENCE: 14

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Pro
            20                  25

<210> SEQ ID NO 15
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 15

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Ile Asn Tyr
            20                  25

<210> SEQ ID NO 16
<211> LENGTH: 31
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 16

Ile Asn His Glu Gln Trp Ala Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 17
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 17

Ala Ser Met Phe Thr Phe Phe Ser Asp Tyr Ser Lys Tyr Leu Asp Ser
1               5                   10                  15

Arg Arg Ala Gln Asp Phe Val Gln Trp Leu Met Leu Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
```

<223> OTHER INFORMATION: C-terminal amide

<400> SEQUENCE: 18

His Ser Gln Gly Thr Phe Leu Ser Asp Tyr Ser Lys Leu Leu Asp Ser
1               5                   10                  15

Arg Arg Ala Gln Asp Phe Val Gln Trp Leu Met Gln Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (29)..(29)
<223> OTHER INFORMATION: C-terminal amide

<400> SEQUENCE: 19

His Ser Gln Gly Thr Phe Leu His Asp Tyr Tyr Tyr Tyr Leu Asp Ser
1               5                   10                  15

Arg Arg Ala Gln Asp Phe Val Gln Trp Leu Met Asp Thr
            20                  25

<210> SEQ ID NO 20
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 20

His Ser Gln Gly Thr Phe Thr Ser Asp Tyr Ser Lys Tyr Leu Asp Ser
1               5                   10                  15

Ile Arg Ala Gln Asp Phe Val Gln Trp Leu Met Asp Thr
            20                  25

<210> SEQ ID NO 21
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 21

His Ser Gln Gly Thr Phe Thr Ser Asp Tyr Ser Lys Tyr Leu Asp Asn
1               5                   10                  15

Lys Arg Ala Gln Asp Phe Val Gln Trp Leu Met Gln Thr
            20                  25

<210> SEQ ID NO 22
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE

```
<222> LOCATION: (29)..(29)
<223> OTHER INFORMATION: C-terminal amide

<400> SEQUENCE: 22

His Ser Gln Gly Thr Phe Thr Ser Asp Tyr Ser Lys Tyr Leu Asp Ser
1               5                   10                  15

Arg Arg Ala Gln Asp Phe Val Asp Trp Leu Met Asn Glu
            20                  25

<210> SEQ ID NO 23
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 23

His Ser Gln Gly Thr Phe Thr Ser Asp Tyr Ser Lys Tyr Leu Asp Ser
1               5                   10                  15

Arg Arg Ala Gln Glu Phe Val Glu Trp Leu Met Asp Glu
            20                  25

<210> SEQ ID NO 24
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 24

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Ile Asn Thr
            20                  25

<210> SEQ ID NO 25
<211> LENGTH: 31
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 25

Lys Ala Leu Gly Gln Phe Thr Phe Thr Ser Asp Tyr Ser Lys Tyr Leu
1               5                   10                  15

Asp Ser Arg Arg Ala Gln Asp Phe Val Gln Trp Leu Met Asn Thr
            20                  25                  30

<210> SEQ ID NO 26
<211> LENGTH: 29
<212> TYPE: PRT
<213> ORGANISM: Artificial Sequence
<220> FEATURE:
<223> OTHER INFORMATION: peptide
<220> FEATURE:
```

<221> NAME/KEY: MISC_FEATURE
<222> LOCATION: (29)..(29)
<223> OTHER INFORMATION: C-terminal amide

<400> SEQUENCE: 26

His Ser Gln Gly Thr Phe Phe His Asp Tyr Ser Lys Tyr Leu Asp Ser
1               5                   10                  15

Arg Arg Ala Gln Asp Phe Val Gln Trp Leu Leu Asn Thr
            20                  25

<210> SEQ ID NO 27
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 27

His Ser Gln Gly Thr Phe Phe Ser Asp Tyr Ser His Trp Leu Asp Ser
1               5                   10                  15

Arg Arg Ala Gln Asp Phe Val Gln Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 28

His Ser Gln Gly Thr Phe Thr Ser Asp Tyr Ser Lys Tyr Leu Asp Trp
1               5                   10                  15

Arg Arg Ala Gln Asp Phe Val Gln Trp Leu Gln Asn Thr
            20                  25

<210> SEQ ID NO 29
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 29

His Ser Gln Gly Thr Phe Thr Ser Asp Tyr Ser Lys Tyr Leu Asp Ser
1               5                   10                  15

Lys Arg Ala His Asp Phe Val Gln Trp Leu Leu Asn Thr
            20                  25

<210> SEQ ID NO 30
<211> LENGTH: 29
<212> TYPE: PRT
<213> ORGANISM: Artificial Sequence
<220> FEATURE:
<223> OTHER INFORMATION: peptide

```
<220> FEATURE:
<221> NAME/KEY: MISC_FEATURE
<222> LOCATION: (29)..(29)
<223> OTHER INFORMATION: C-terminal amide

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Trp Ile Asp Leu Met Asn Thr
            20                  25

<210> SEQ ID NO 31
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 31

His Ser Gln Gly Thr Phe Thr Ser Asp Tyr Ser Lys Tyr Leu Asp Ser
1               5                   10                  15

Arg Arg Ala Gln Asp Phe Val Met Thr Ser Met Asn Thr
            20                  25

<210> SEQ ID NO 32
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 32

His Ser Gln Gly Thr Phe Thr Ser Asp Tyr Ser Lys Tyr Leu Asp Ser
1               5                   10                  15

Arg Arg Ala Gln Asp Phe Val Asp Trp Leu Leu Asn Ala
            20                  25

<210> SEQ ID NO 33
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 33

His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Asn Asn
            20                  25

<210> SEQ ID NO 34
<211> LENGTH: 29
<212> TYPE: PRT
<213> ORGANISM: Artificial Sequence
<220> FEATURE:
```

```
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 34

His Ser Gln Gly Thr Phe Thr Ser Asp Tyr Ser Lys Tyr Leu Asp Ser
1               5                   10                  15

Arg Arg Ala Gln Asp Phe Val Asp Trp Leu Ile Asn Ser
            20                  25

<210> SEQ ID NO 35
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 35

His Ser His Gly Thr Phe Thr Ser Asp Tyr Ser Lys Tyr Leu Asp Ser
1               5                   10                  15

Arg Arg Ala Gln Asp Phe Val Gln Trp Leu Met Thr Thr
            20                  25

<210> SEQ ID NO 36
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 36

His Ser Gln Gly Ile Phe Phe Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 37
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 37

His Ser Gln Gly Thr Phe Leu Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 38
<211> LENGTH: 29
<212> TYPE: PRT
<213> ORGANISM: Artificial Sequence
```

```
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 38

His Ser Gln Gly Thr Phe Thr Ser Asp Tyr Ser Trp Tyr Leu Asp Ser
1               5                   10                  15

Arg Arg Ala Gln Asp Phe Val Gln Trp Leu Met Asn Thr
            20                  25

<210> SEQ ID NO 39
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 39

His Ser Gln Gly Thr Phe Thr Ser Asp Tyr Ser Lys Tyr Leu Asp Met
1               5                   10                  15

Gln Arg Ala His Asp Phe Val Gln Trp Leu Met Asn Thr
            20                  25

<210> SEQ ID NO 40
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 40

His Ser Gln Gly Thr Phe Thr Ser Asp Tyr Ser Lys Tyr Leu Asp Ser
1               5                   10                  15

Arg Met Ala Tyr Asp Phe Val Gln Trp Leu Met Asn Thr
            20                  25

<210> SEQ ID NO 41
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 41

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Gln
            20                  25

<210> SEQ ID NO 42
<211> LENGTH: 29
<212> TYPE: PRT
```

```
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 42

His Ser Gln Gly Thr Phe Phe Ser Asp Tyr Ser Lys Tyr Leu Asp Ser
1               5                   10                  15

Arg Arg Ala Gln Asp Phe Val Gln Trp Leu Leu Glu Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (29)..(29)
<223> OTHER INFORMATION: C-terminal amide

<400> SEQUENCE: 43

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Leu Asp Ser
            20                  25

<210> SEQ ID NO 44
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is D-Ser
<220> FEATURE:
<221> NAME/KEY: MISC_FEATURE
<222> LOCATION: (29)..(29)
<223> OTHER INFORMATION: C-terminal amide

<400> SEQUENCE: 44

His Ser Gln Gly Thr Phe Thr Ser Asp Lys Ser Lys Tyr Leu Asp Asn
1               5                   10                  15

Lys Arg Ala Gln Asp Phe Val Gln Trp Leu Met Gln Thr
            20                  25

<210> SEQ ID NO 45
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is D-Ser
<220> FEATURE:
<221> NAME/KEY: MISC_FEATURE
<222> LOCATION: (29)..(29)
<223> OTHER INFORMATION: C-terminal amide

<400> SEQUENCE: 45

His Xaa Gln Gly Thr Phe Thr Ser Asp Lys Ser Lys Tyr Leu Asp Ser
```

```
1               5                   10                  15
Arg Arg Ala His Asp Phe Val Gln Trp Leu Leu Asn Thr
            20                  25
```

<210> SEQ ID NO 46
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is D-Ser
<220> FEATURE:
<221> NAME/KEY: MISC_FEATURE
<222> LOCATION: (29)..(29)
<223> OTHER INFORMATION: C-terminal amide

<400> SEQUENCE: 46

```
His Xaa Gln Gly Thr Phe Leu Ser Asp Lys Ser Lys Leu Leu Asp Ser
1               5                   10                  15
Arg Arg Ala Gln Asp Phe Val Gln Trp Leu Met Gln Thr
            20                  25
```

<210> SEQ ID NO 47
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is D-Ser
<220> FEATURE:
<221> NAME/KEY: MISC_FEATURE
<222> LOCATION: (29)..(29)
<223> OTHER INFORMATION: C-terminal amide

<400> SEQUENCE: 47

```
His Xaa Gln Gly Thr Phe Leu Ser Asp Tyr Ser Lys Leu Leu Asp Ser
1               5                   10                  15
Arg Ala Ala Gln Asp Phe Val Gln Trp Leu Leu Gln Thr
            20                  25
```

<210> SEQ ID NO 48
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is D-Ser
<220> FEATURE:
<221> NAME/KEY: MISC_FEATURE
<222> LOCATION: (29)..(29)
<223> OTHER INFORMATION: C-terminal amide

<400> SEQUENCE: 48

```
His Xaa Gln Gly Thr Phe Thr Ser Asp Lys Ser Lys Tyr Leu Asp Ala
1               5                   10                  15
Arg Ala Ala His Asp Phe Val Gln Trp Leu Leu Asn Thr
            20                  25
```

<210> SEQ ID NO 49

```
<211> LENGTH: 31
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric (aib)
<220> FEATURE:
<221> NAME/KEY: MISC_FEATURE
<222> LOCATION: (10)..(10)
<223> OTHER INFORMATION: Lys is conjugated to gamma-Glu gamma-Glu C16
<220> FEATURE:
<221> NAME/KEY: MISC_FEATURE
<222> LOCATION: (31)..(31)
<223> OTHER INFORMATION: Xaa is gamma-Glu
<220> FEATURE:
<221> NAME/KEY: MISC_FEATURE
<222> LOCATION: (31)..(31)
<223> OTHER INFORMATION: C-terminal amide

<400> SEQUENCE: 49

His Xaa Gln Gly Thr Phe Thr Ser Asp Lys Ser Lys Tyr Leu Asp Ser
 1               5                  10                  15

Arg Arg Ala His Asp Phe Val Gln Trp Leu Leu Asn Thr Lys Xaa
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutyric (aib)
<220> FEATURE:
<221> NAME/KEY: MISC_FEATURE
<222> LOCATION: (10)..(10)
<223> OTHER INFORMATION: Lys is conjugated to gamma-Glu gamma-Glu C16
<220> FEATURE:
<221> NAME/KEY: MISC_FEATURE
<222> LOCATION: (31)..(31)
<223> OTHER INFORMATION: Xaa is gamma-Glu
<220> FEATURE:
<221> NAME/KEY: MISC_FEATURE
<222> LOCATION: (31)..(31)
<223> OTHER INFORMATION: C-terminal amide

<400> SEQUENCE: 50

His Xaa Gln Gly Thr Phe Thr Ser Asp Lys Ser Lys Tyr Leu Asp Ala
 1               5                  10                  15

Arg Ala Ala His Asp Phe Val Gln Trp Leu Leu Asn Thr Lys Xaa
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is alpha-aminoisobutryic (aib)
<220> FEATURE:
<221> NAME/KEY: MISC_FEATURE
<222> LOCATION: (10)..(10)
<223> OTHER INFORMATION: Lys is conjugated to gamma-Glu gamma-Glu C16
<220> FEATURE:
<221> NAME/KEY: MISC_FEATURE
```

```
<222> LOCATION: (31)..(31)
<223> OTHER INFORMATION: Xaa is gamma-Glu
<220> FEATURE:
<221> NAME/KEY: MISC_FEATURE
<222> LOCATION: (31)..(31)
<223> OTHER INFORMATION: C-terminal amide

<400> SEQUENCE: 51

His Xaa Gln Gly Thr Phe Thr Ser Asp Lys Ser Lys Tyr Leu Asp Asn
1               5                   10                  15

Lys Arg Ala Gln Asp Phe Val Gln Trp Leu Met Gln Thr Lys Xaa
            20                  25                  30

<210> SEQ ID NO 52
<211> LENGTH: 29
<212> TYPE: PRT
<213> ORGANISM: Homo sapiens

<400> SEQUENCE: 52

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 53
<211> LENGTH: 31
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(7)
<223> OTHER INFORMATION: Xaa is any amino acid with the proviso that for
      each position in 45% of the peptides the amino acid is maintained
      as the wild type amino acid while in 55% of the peptides the amino
      acid is any other amino acid except cysteine
<220> FEATURE:
<221> NAME/KEY: MISC_FEATURE
<222> LOCATION: (29)..(30)
<223> OTHER INFORMATION: Xaa is any amino acid with the proviso that for
      each position in 45% of the peptides the amino acid is maintained
      as the wild type amino acid while in 55% of the peptides the amino
      acid is any other amino acid except cysteine

<400> SEQUENCE: 53

Xaa Xaa Xaa Xaa Xaa Xaa Xaa Phe Thr Ser Asp Tyr Ser Lys Tyr Leu
1               5                   10                  15

Asp Ser Arg Arg Ala Gln Asp Phe Val Gln Trp Leu Xaa Xaa Thr
            20                  25                  30

<210> SEQ ID NO 54
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(7)
<223> OTHER INFORMATION: Xaa is any amino acid with the proviso that for
      each position in 45% of the peptides the amino acid is maintained
      as the wild type amino acid while in 55% of the peptides the amino
      acid is any other amino acid except cysteine
<220> FEATURE:
<221> NAME/KEY: MISC_FEATURE
<222> LOCATION: (27)..(28)
<223> OTHER INFORMATION: Xaa is any amino acid with the proviso that for
      each position in 45% of the peptides the amino acid is maintained
      as the wild type amino acid while in 55% of the peptides the amino
``` acid is any other amino acid except cysteine

<400> SEQUENCE: 54

Xaa Xaa Xaa Xaa Xaa Xaa Ser Asp Tyr Ser Lys Tyr Leu Asp Ser
1               5                   10                  15

Arg Arg Ala Gln Asp Phe Val Gln Trp Leu Xaa Xaa Thr
            20                  25

<210> SEQ ID NO 55
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (7)..(13)
<223> OTHER INFORMATION: Xaa is any amino acid with the proviso that for
      each position in 45% of the peptides the amino acid is maintained
      as the wild type amino acid while in 55% of the peptides the amino
      acid is any other amino acid except cysteine
<220> FEATURE:
<221> NAME/KEY: MISC_FEATURE
<222> LOCATION: (27)..(28)
<223> OTHER INFORMATION: Xaa is any amino acid with the proviso that for
      each position in 45% of the peptides the amino acid is maintained
      as the wild type amino acid while in 55% of the peptides the amino
      acid is any other amino acid except cysteine

<400> SEQUENCE: 55

His Ser Gln Gly Thr Phe Xaa Xaa Xaa Xaa Xaa Xaa Xaa Leu Asp Ser
1               5                   10                  15

Arg Arg Ala Gln Asp Phe Val Gln Trp Leu Xaa Xaa Thr
            20                  25

<210> SEQ ID NO 56
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (14)..(20)
<223> OTHER INFORMATION: Xaa is any amino acid with the proviso that for
      each position in 45% of the peptides the amino acid is maintained
      as the wild type amino acid while in 55% of the peptides the amino
      acid is any other amino acid except cysteine
<220> FEATURE:
<221> NAME/KEY: MISC_FEATURE
<222> LOCATION: (27)..(28)
<223> OTHER INFORMATION: Xaa is any amino acid with the proviso that for
      each position in 45% of the peptides the amino acid is maintained
      as the wild type amino acid while in 55% of the peptides the amino
      acid is any other amino acid except cysteine

<400> SEQUENCE: 56

His Ser Gln Gly Thr Phe Thr Ser Asp Tyr Ser Lys Tyr Xaa Xaa Xaa
1               5                   10                  15

Xaa Xaa Xaa Xaa Asp Phe Val Gln Trp Leu Xaa Xaa Thr
            20                  25

<210> SEQ ID NO 57
<211> LENGTH: 29
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (21)..(29)
<223> OTHER INFORMATION: Xaa is any amino acid with the proviso that for
each position in 45% of the peptides the amino acid is maintained
as the wild type amino acid while in 55% of the peptides the amino
acid is any other amino acid except cysteine

<400> SEQUENCE: 57

His Ser Gln Gly Thr Phe Thr Ser Asp Tyr Ser Lys Tyr Leu Asp Ser
1               5                   10                  15

Arg Arg Ala Gln Xaa Xaa Xaa Xaa Xaa Xaa Xaa Xaa Xaa
            20                  25

<210> SEQ ID NO 58
<211> LENGTH: 32
<212> TYPE: DNA
<213> ORGANISM: Artificial Sequence
<220> FEATURE:
<223> OTHER INFORMATION: oligonucleotide

<400> SEQUENCE: 58
gactgctagc accatgcccc cctgccagcc ac                                   32

<210> SEQ ID NO 59
<211> LENGTH: 31
<212> TYPE: DNA
<213> ORGANISM: Artificial Sequence
<220> FEATURE:
<223> OTHER INFORMATION: oligonucleotide

<400> SEQUENCE: 59
gactgctagc accatggccg gcgccccgg c                                     31

<210> SEQ ID NO 60
<211> LENGTH: 40
<212> TYPE: DNA
<213> ORGANISM: Artificial Sequence
<220> FEATURE:
<223> OTHER INFORMATION: oligonucleotide

<400> SEQUENCE: 60
atcgatcgat ttaaacctta tcgtcgtcat ccttgtaatc                           40

<210> SEQ ID NO 61
<211> LENGTH: 80
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (12)..(14)
<223> OTHER INFORMATION: wherein n12n13n14 have the triplet sequences
AAA, AAT, ACT, ATA, ATG,CAG, CAT, CCG, CGT, CTG, GAA, GAT, GCT,
GGT, GTT, TAC, TCT, TGG, or TTT in which each triplet is each
present 5.26% of the time
<220> FEATURE:
<221> NAME/KEY: misc_feature
<222> LOCATION: (15)..(17)
<223> OTHER INFORMATION: wherein n15n16n17 have the triplet sequences
AAA, AAT, ACT, ATA, ATG,CAG, CAT, CCG, CGT, CTG, GAA, GAT, GCT,
GGT, GTT, TAC, TCT, TGG, or TTT in which each triplet is each
present 5.26% of the time
<220> FEATURE:
<221> NAME/KEY: misc_feature
<222> LOCATION: (18)..(20)
<223> OTHER INFORMATION: wherein n18n19n20 have the triplet sequence CAT
present 45% percent of the time and the triplet sequences AAA,
AAT, ACT, ATA, ATG,CAG, CCG, CGT, GAA, GAT, GCT, GGT, GTT,
TAC, TCT, TGG, or TTT are each present 5.26% of the time
<220> FEATURE:

<221> NAME/KEY: misc_feature
<222> LOCATION: (21)..(23)
<223> OTHER INFORMATION: wherein n21n22n23 have the triplet sequence TCT
    which present 45% percent of the time and the triplet sequences
    AAA, AAT, ACT, ATA, ATG,CAG, CAT, CCG, CGT, CTG, GAA, GAT, GCT,
    GGT, GTT, TAC, TGG, or TTT are each present 5.26% of the time
<220> FEATURE:
<221> NAME/KEY: misc_feature
<222> LOCATION: (24)..(26)
<223> OTHER INFORMATION: wherein n24n25n26 have the triplet sequence CAG
    present 45% percent of the time and the triplet sequences AAA,
    AAT, ACT, ATA, ATG, CAT, CCG, CGT, CTG, GAA, GAT, GCT, GGT, GTT,
    TAC, TGG, TCT, or TTT are each present 5.26% of the time
<220> FEATURE:
<221> NAME/KEY: misc_feature
<222> LOCATION: (27)..(29)
<223> OTHER INFORMATION: wherein n27n28n29 have the triplet sequence GGT
    present 45% percent of the time and the triplet sequences AAA,
    AAT, ACT, ATA, ATG,CAG, CAT, CCG, CGT, CTG, GAA, GAT, GCT, GTT,
    TAC, TCT, TGG, or TTT are each present 5.26% of the time
<220> FEATURE:
<221> NAME/KEY: misc_feature
<222> LOCATION: (30)..(32)
<223> OTHER INFORMATION: wherein n30n31n32 have the triplet sequence ACT
    present 45% percent of the time and the triplet sequences AAA,
    AAT, ATA, ATG,CAG, CAT, CCG, CGT, CTG, GAA, GAT, GCT, GGT, GTT,
    TAC, TCT, TGG, or TTT are each present 5.26% of the time

<400> SEQUENCE: 61
gccggatggc annnnnnnnn nnnnnnnnnn nntttacctc tgattacagc aaatacctgg    60
attctagacg tgctcaagac                                                80

<210> SEQ ID NO 62
<211> LENGTH: 76
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (14)..(16)
<223> OTHER INFORMATION: wherein n14n15n16 have the triplet sequence CAT
    present 45% percent of the time and the triplet sequences AAA,
    AAT, ACT, ATA, ATG,CAG, CCG, CGT, CTG, GAA, GAT, GCT, GGT, GTT,
    TAC, TCT, TGG, or TTT are each present 5.26% of the time
<220> FEATURE:
<221> NAME/KEY: misc_feature
<222> LOCATION: (17)..(19)
<223> OTHER INFORMATION: wherein n17n18n19 have the triplet sequence TCT
    present 45% percent of the time and the triplet sequences AAA,
    AAT, ACT, ATA, ATG,CAG, CCG, CGT, CTG, CAT, GAA, GAT, GCT, GGT,
    GTT, TAC, TGG, or TTT are each present 5.26% of the time
<220> FEATURE:
<221> NAME/KEY: misc_feature
<222> LOCATION: (20)..(22)
<223> OTHER INFORMATION: wherein n20n21n22 have the triplet sequence CAG
    present 45% percent of the time and the triplet sequences AAA,
    AAT, ACT, ATA, ATG, CCG, CGT, CTG, CAT, GAA, GAT, GCT, GGT, GTT,
    TAC, TCT, TGG, or TTT are each present 5.26% of the time
<220> FEATURE:
<221> NAME/KEY: misc_feature
<222> LOCATION: (23)..(25)
<223> OTHER INFORMATION: wherein n23n24n25 have the triplet sequence GGT
    present 45% percent of the time and the triplet sequences AAA,
    AAT, ACT, ATA, ATG,CAG, CCG, CGT, CTG, CAT, GAA, GAT, GCT, GTT,
    TAC, TCT, TGG, or TTT are each present 5.26% of the time
<220> FEATURE:
<221> NAME/KEY: misc_feature
<222> LOCATION: (26)..(28)
<223> OTHER INFORMATION: wherein n26n27n28 have the triplet sequence ACT
    present 45% percent of the time and the triplet sequences AAA,
    AAT, ATA, ATG,CAG, CCG, CGT, CTG, CAT, GAA, GAT, GCT, GGT, GTT,
    TAC, TCT, TGG, or TTT are each present 5.26% of the time
<220> FEATURE:
<221> NAME/KEY: misc_feature
<222> LOCATION: (29)..(31)

```
<223> OTHER INFORMATION: wherein n29n30n31 have the triplet sequence TTT
      present 45% percent of the time and the triplet sequences AAA,
      AAT, ACT, ATA, ATG,CAG, CCG, CGT, CTG, CAT, GAA, GAT, GCT, GGT,
      GTT, TAC, TCT, OR TGG are each present 5.26% of the time
<220> FEATURE:
<221> NAME/KEY: misc_feature
<222> LOCATION: (32)..(34)
<223> OTHER INFORMATION: wherein n32n33n34 have the triplet sequence ACT
      present 45% percent of the time and the triplet sequences AAA,
      AAT, ATA, ATG,CAG, CCG, CGT, CTG, CAT, GAA, GAT, GCT, GGT, GTT,
      TAC, TCT, TGG, or TTT are each present 5.26% of the time

<400> SEQUENCE: 62
gccggccatg gcannnnnnn nnnnnnnnnn nnnntctgat tacagcaaat acctggattc      60
tagacgtgct caagac                                                      76

<210> SEQ ID NO 63
<211> LENGTH: 76
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (32)..(34)
<223> OTHER INFORMATION: wherein n32n33n34 have the triplet sequence ACT
      present 45% percent of the time and the triplet sequences AAA,
      AAT, ATA, ATG,CAG, CCG, CGT, CTG, CAT, GAA, GAT, GCT, GGT, GTT,
      TAC, TCT, TGG, or TTT are each present 5.26% of the time
<220> FEATURE:
<221> NAME/KEY: misc_feature
<222> LOCATION: (35)..(37)
<223> OTHER INFORMATION: wherein n35n36n37 have the triplet sequence TCT
      present 45% percent of the time and the triplet sequences AAA,
      AAT, ACT, ATA, ATG,CAG, CCG, CGT, CTG, CAT, GAA, GAT, GCT, GGT,
      GTT, TAC, TGG, or TTT are each present 5.26% of the time
<220> FEATURE:
<221> NAME/KEY: misc_feature
<222> LOCATION: (38)..(40)
<223> OTHER INFORMATION: wherein n38n39n40 have the triplet sequence GAT
      present 45% percent of the time and the triplet sequences AAA,
      AAT, ACT, ATA, ATG,CAG, CCG, CGT, CTG, CAT, GAA, GCT, GGT, GTT,
      TAC, TCT, TGG, or TTT are each present 5.26% of the time
<220> FEATURE:
<221> NAME/KEY: misc_feature
<222> LOCATION: (41)..(43)
<223> OTHER INFORMATION: wherein n41n42n43 have the triplet sequence TAC
      present 45% percent of the time and the triplet sequences AAA,
      AAT, ACT, ATA, ATG,CAG, CCG, CGT, CTG, CAT, GAA, GAT, GCT, GGT,
      GTT, TCT, TGG, or TTT are each present 5.26% of the time
<220> FEATURE:
<221> NAME/KEY: misc_feature
<222> LOCATION: (44)..(46)
<223> OTHER INFORMATION: wherein n44n45n46 have the triplet sequence TCT
      present 45% percent of the time and the triplet sequences AAA,
      AAT, ACT, ATA, ATG,CAG, CCG, CGT, CTG, CAT, GAA, GAT, GCT, GGT,
      GTT, TAC, TGG, or TTT are each present 5.26% of the time
<220> FEATURE:
<221> NAME/KEY: misc_feature
<222> LOCATION: (47)..(49)
<223> OTHER INFORMATION: wherein n47n48n49 have the triplet sequence AAA
      present 45% percent of the time and the triplet sequences AAT,
      ACT, ATA, ATG,CAG, CCG, CGT, CTG, CAT, GAA, GAT, GCT, GGT, GTT,
      TAC, TCT, TGG, or TTT are each present 5.26% of the time
<220> FEATURE:
<221> NAME/KEY: misc_feature
<222> LOCATION: (50)..(52)
<223> OTHER INFORMATION: wherein n50n151n52 have the triplet sequence
      TAC present 45% percent of the time and the triplet sequences AAA,
      AAT, ACT, ATA, ATG,CAG, CCG, CGT, CTG, CAT, GAA, GAT, GCT, GGT,
      GTT, TCT, TGG, or TTT are each present 5.26% of the time

<400> SEQUENCE: 63
gccggccatg gcacattctc agggtacctt tnnnnnnnnn nnnnnnnnnn nnctggattc      60
```

```
tagacgtgct caagac                                              76

<210> SEQ ID NO 64
<211> LENGTH: 52
<212> TYPE: DNA
<213> ORGANISM: Artificial Sequence
<220> FEATURE:
<223> OTHER INFORMATION: oligonucleotide

<400> SEQUENCE: 64
gccggccatg gcacattctc agggtaccttt caccagcgac tacagcaagt ac      52

<210> SEQ ID NO 65
<211> LENGTH: 67
<212> TYPE: DNA
<213> ORGANISM: Artificial Sequence
<220> FEATURE:
<223> OTHER INFORMATION: oligonucleotide

<400> SEQUENCE: 65
ccggccatgg cacattctca gggtaccttt acctctgatt atagcaagta tctggattct  60
cgtcgtg                                                         67

<210> SEQ ID NO 66
<211> LENGTH: 61
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (19)..(21)
<223> OTHER INFORMATION: wherein n19n20n21 have the triplet sequence GTT
      present 45% of the time and the triplet sequences TTT, CGT, AAT,
      CAT, CTG, ATG, CGG, TCT, CAG, TTC, ATC, TGC, ACC, AAC, ATA, ACT,
      CCA, or AAA are each present 5.36% of the time
<220> FEATURE:
<221> NAME/KEY: misc_feature
<222> LOCATION: (22)..(24)
<223> OTHER INFORMATION: wherein n19n20n21 have the triplet sequence CAT
      present 45% of the time and the triplet sequences TTT, GTT, CGT,
      AAT, CTG, ATG, CGG, TCT, CAG, TTC, ATC, TGC, ACC, AAC, ATA, ACT,
      CCA, or AAA are each present 5.36% of the time

<400> SEQUENCE: 66
ctgtgcggcc gcaccagtnn nnnncagcca ctgaacaaag tcttgagcac gtctagaatc  60
c                                                               61

<210> SEQ ID NO 67
<211> LENGTH: 85
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (19)..(21)
<223> OTHER INFORMATION: wherein n19n20n21 have the triplet sequence GTT
      present 45% percent of the time and the triplet sequences TTT,
      CGT, AAT, CAT, CTG, ATG, CGG, TCT, CAG, TTC, ATC, TGC, ACC, AAC,
      ATA, ACT, CCA, or AAA are each present 5.26% of the time
<220> FEATURE:
<221> NAME/KEY: misc_feature
<222> LOCATION: (22)..(24)
<223> OTHER INFORMATION: wherein n22n23n24 have the triplet sequence CAT
      present 45% percent of the time and the triplet sequences TTT,
      GTT, CGT, AAT, CTG, ATG, CGG, TCT, CAG, TTC, ATC, TGC, ACC, AAC,
      ATA, ACT, CCA, or AAA are each present 5.26% of the time
<220> FEATURE:
<221> NAME/KEY: misc_feature
```

```
<222> LOCATION: (43)..(45)
<223> OTHER INFORMATION: wherein n43n44n45 have the triplet sequence CTG
      present 45% percent of the time and the triplet sequences TTT,
      GTT, CGT, AAT, CAT, ATG, CGG, TCT, CAG, TTC, ATC, TGC, ACC, AAC,
      ATA, ACT, CCA, or AAA are each present 5.26% of the time
<220> FEATURE:
<221> NAME/KEY: misc_feature
<222> LOCATION: (46)..(48)
<223> OTHER INFORMATION: wherein n46n47n48 have the triplet sequence TGC
      present 45% percent of the time and the triplet sequences TTT,
      GTT, CGT, AAT, CAT, CTG, ATG, CGG, TCT, CAG, TTC, ATC, ACC, AAC,
      ATA, ACT, CCA, or AAA are each present 5.26% of the time
<220> FEATURE:
<221> NAME/KEY: misc_feature
<222> LOCATION: (49)..(51)
<223> OTHER INFORMATION: wherein n49n50n51 have the triplet sequence TCT
      present 45% percent of the time and the triplet sequences TTT,
      GTT, CGT, AAT, CAT, CTG, ATG, CGG, CAG, TTC, ATC, TGC, ACC, AAC,
      ATA, ACT, CCA, or AAA are each present 5.26% of the time
<220> FEATURE:
<221> NAME/KEY: misc_feature
<222> LOCATION: (52)..(54)
<223> OTHER INFORMATION: wherein n52n53n54 have the triplet sequence ACT
      present 45% percent of the time and the triplet sequences TTT,
      GTT, CGT, AAT, CAT, CTG, ATG, CGG, TCT, CAG, TTC, ATC, TGC, ACC,
      AAC, ATA, CCA, or AAA are each present 5.26% of the time
<220> FEATURE:
<221> NAME/KEY: misc_feature
<222> LOCATION: (55)..(57)
<223> OTHER INFORMATION: wherein n55n156n57 have the triplet sequence
      ATC present 45% percent of the time and the triplet sequences TTT,
      GTT, CGT, AAT, CAT, CTG, ATG, CGG, TCT, CAG, TTC, ATC, TGC, ACC,
      AAC, ATA, ACT, CCA, or AAA are each present 5.26% of the time
<220> FEATURE:
<221> NAME/KEY: misc_feature
<222> LOCATION: (58)..(60)
<223> OTHER INFORMATION: wherein n58n59n60 have the triplet sequence CAG
      present 45% percent of the time and the triplet sequences TTT,
      GTT, CGT, AAT, CAT, CTG, ATG, CGG, TCT, TTC, ATC, TGC, ACC, AAC,
      ATA, ACT, CCA, or AAA are each present 5.26% of the time
<220> FEATURE:
<221> NAME/KEY: misc_feature
<222> LOCATION: (61)..(63)
<223> OTHER INFORMATION: n is a, c, g, or t

<400> SEQUENCE: 67
ctgtgcggcc gcaccagtnn nnnncagcca ctgaacgaag tcnnnnnnnn nnnnnnnnnn      60
nnngtacttg ctgtagtcgc tggtg                                           85

<210> SEQ ID NO 68
<211> LENGTH: 70
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (16)..(18)
<223> OTHER INFORMATION: wherein n16n17n18 have the triplet sequence CGT
      present 45% percent of the time and the triplet sequences TTT,
      GTT, AAT, CAT, CTG, ATG, CGG, TCT, CAG, TTC, ATC, TGC, ACC, AAC,
      ATA, ACT, CCA, or AAA are each present 5.26% of the time
<220> FEATURE:
<221> NAME/KEY: misc_feature
<222> LOCATION: (19)..(21)
<223> OTHER INFORMATION: wherein n19n20n21 have the triplet sequence GTT
      present 45% percent of the time and the triplet sequences TTT,
      CGT, AAT, CAT, CTG, ATG, CGG, TCT, CAG, TTC, ATC, TGC, ACC, AAC,
      ATA, ACT, CCA, or AAA are each present 5.26% of the time
<220> FEATURE:
<221> NAME/KEY: misc_feature
<222> LOCATION: (22)..(24)
<223> OTHER INFORMATION: wherein n22n23n24 have the triplet sequence CAT
      present 45% percent of the time and the triplet sequences TTT,
      GTT, CGT, AAT, CTG, ATG, CGG, TCT, CAG, TTC, ATC, TGC, ACC, AAC,
      ATA, ACT, CCA, or AAA are each present 5.26% of the time
```

```
<220> FEATURE:
<221> NAME/KEY: misc_feature
<222> LOCATION: (25)..(27)
<223> OTHER INFORMATION: wherein n25n26n27 have the triplet sequence CAG
      present 45% percent of the time and the triplet sequences TTT,
      GTT, CGT, AAT, CAT, CTG, ATG, CGG, TCT, TTC, ATC, TGC, ACC, AAC,
      ATA, ACT, CCA, or AAA are each present 5.26% of the time
<220> FEATURE:
<221> NAME/KEY: misc_feature
<222> LOCATION: (28)..(30)
<223> OTHER INFORMATION: wherein n28n29n30 have the triplet sequence CCA
      present 45% percent of the time and the triplet sequences TTT,
      GTT, CGT, AAT, CAT, CTG, ATG, CGG, TCT, CAG, TTC, ATC, TGC, ACC,
      AAC, ATA, ACT, or AAA are each present 5.26% of the time
<220> FEATURE:
<221> NAME/KEY: misc_feature
<222> LOCATION: (31)..(33)
<223> OTHER INFORMATION: wherein n31n32n33 have the triplet sequence CTG
      present 45% percent of the time and the triplet sequences TTT,
      GTT, CGT, AAT, CAT, ATG, CGG, TCT, CAG, TTC, ATC, TGC, ACC, AAC,
      ATA, ACT, CCA, or AAA are each present 5.26% of the time
<220> FEATURE:
<221> NAME/KEY: misc_feature
<222> LOCATION: (34)..(36)
<223> OTHER INFORMATION: wherein n34n35n36 have the triplet sequence AAC
      present 45% percent of the time and the triplet sequences TTT,
      GTT, CGT, AAT, CAT, CTG, ATG, CGG, TCT, CAG, TTC, ATC, TGC, ACC,
      ATA, ACT, CCA, or AAA are each present 5.26% of the time
<220> FEATURE:
<221> NAME/KEY: misc_feature
<222> LOCATION: (37)..(39)
<223> OTHER INFORMATION: wherein n37n38n39 have the triplet sequence AAA
      present 45% percent of the time and the triplet sequences TTT,
      GTT, CGT, AAT, CAT, CTG, ATG, CGG, TCT, CAG, TTC, ATC, TGC, ACC,
      AAC, ATA, ACT, or CCA are each present 5.26% of the time
<220> FEATURE:
<221> NAME/KEY: misc_feature
<222> LOCATION: (40)..(42)
<223> OTHER INFORMATION: wherein n40n41n42 have the triplet sequence ATC
      present 45% percent of the time and the triplet sequences TTT,
      GTT, CGT, AAT, CAT, CTG, ATG, CGG, TCT, CAG, TTC, TGC, ACC, AAC,
      ATA, ACT, CCA, or AAA are each present 5.26% of the time

<400> SEQUENCE: 68
ctgtgcggcc gcactnnnnn nnnnnnnnnn nnnnnnnnnn nnctgagcac gacgagagtc    60
cagatacttg                                                           70
```

What is claimed:

1. A co-agonist peptide comprising a peptide selected from following peptides

| SEQ ID NO: | Name | Sequence |
|---|---|---|
| 1 | PD17 | HSVGNFWSDYSKYLDSRRAQDFVQWLMLT-CONH$_2$ |
| 2 | PD18 | HSQGTFTSDYSKYVEDRRAHDFVQWLMNT-CONH$_2$ |
| 3 | PD19 | HSQGTFTSDYRKYLDERAAWDFVQWLMNT-CONH$_2$ |
| 4 | PD20 | HSQGTFTSDYSKYLNSWMTQDFVQWLMNT-CONH$_2$ |
| 5 | PD21 | HSQGTFTSDYSKYLDIGRAQDFVQWLLNT-CONH$_2$ |
| 6 | PD22 | HSQGTFTSDYSKYLDSLMAQDFVQWLMST-CONH$_2$ |
| 7 | PD23 | HSQGTFTSDYSKYLDWRRAQDFVQWLLNT-CONH$_2$ |
| 8 | PD24 | HSQGTFTSDYIKLLDSRRAQDFVQWLMNT-CONH$_2$ |
| 9 | PD25 | HSQGTFTSDYSKYLDARRAQDFVQWLIRT-CONH$_2$ |
| 10 | PD26 | HSQGTFTSDYSKYLDVRRAQDFVQWLMNT-CONH$_2$ |
| 11 | PD27 | HSQGTFTSDYSKYLDELRAYDFVQWLMNT-CONH$_2$ |
| 12 | PD28 | HSQGTFTSDYSKYLDYMRAYDFVQWLMNT-CONH$_2$ |
| 13 | PD29 | HSQGTFTSDYSKYLDSRRAHDFVQWLLNT-CONH$_2$ |
| 14 | PD30 | HSQGTFTSDYSKYLDSRRAQDFVQWLMNP-CONH$_2$ |
| 15 | PD31 | HSQGTFTSDYSKYLDSRRAQDFVQWLINY-CONH$_2$ |
| 16 | PD32 | INHEQWAFTSDYSKYLDSRRAQDFVQWLMNT-CONH$_2$ |
| 17 | PD33 | ASMFTFFSDYSKYLDSRRAQDFVQWLMLT-CONH$_2$ |
| 18 | PD34 | HSQGTFLSDYSKLLDSRRAQDFVQWLMQT-CONH$_2$ |
| 19 | PD35 | HSQGTFLHDYYYYLDSRRAQDFVQWLMDT-CONH$_2$ |
| 20 | PD36 | HSQGTFTSDYSKYLDSIRAQDFVQWLMDT-CONH$_2$ |

| SEQ ID NO: | Name | Sequence |
|---|---|---|
| 21 | PD37 | HSQGTFTSDYSKYLDNKRAQDFVQWLMQT-CONH₂ |
| 22 | PD38 | HSQGTFTSDYSKYLDSRRAQDFVDWLMNE-CONH₂ |
| 23 | PD39 | HSQGTFTSDYSKYLDSRRAQEFVEWLMDE-CONH₂ |
| 24 | PD40 | HSQGTFTSDYSKYLDSRRAQDFVQWLINT-CONH₂ |
| 25 | PD41 | KALGQFTFTSDYSKYLDSRRAQDFVQWLMNT-CONH₂ |
| 26 | PD42 | HSQGTFFHDYSKYLDSRRAQDFVQWLLNT-CONH₂ |
| 27 | PD43 | HSQGTFFSDYSHWLDSRRAQDFVQWLMNT-CONH₂ |
| 28 | PD44 | HSQGTFTSDYSKYLDWRRAQDFVQWLQNT-CONH₂ |
| 29 | PD45 | HSQGTFTSDYSKYLDSKRAHDFVQWLLNT-CONH₂ |
| 30 | PD46 | HSQGTFTSDYSKYLDSRRAQDFWIDLMNT-CONH₂ |
| 31 | PD47 | HSQGTFTSDYSKYLDSRRAQDFVMTSMNT-CONH₂ |
| 32 | PD48 | HSQGTFTSDYSKYLDSRRAQDFVDWLLNA-CONH₂ |
| 33 | PD49 | HSQGTFTSDYSKYLDSRRAQDFVEWLMNN-CONH₂ |
| 34 | PD50 | HSQGTFTSDYSKYLDSRRAQDFVDWLINS-CONH₂ |
| 35 | PD51 | HSHGTFTSDYSKYLDSRRAQDFVQWLMTT-CONH₂ |
| 36 | PD52 | HSQGIFFSDYSKYLDSRRAQDFVQWLMNT-CONH₂ |
| 37 | PD53 | HSQGTFLSDYSKYLDSRRAQDFVQWLMNT-CONH₂ |
| 38 | PD54 | HSQGTFTSDYSWYLDSRRAQDFVQWLMNT-CONH₂ |
| 39 | PD55 | HSQGTFTSDYSKYLDMQRAHDFVQWLMNT-CONH₂ |
| 40 | PD56 | HSQGTFTSDYSKYLDSRMAYDFVQWLMNT-CONH₂ |
| 41 | PD57 | HSQGTFTSDYSKYLDSRRAQDFVQWLLNQ-CONH₂ |
| 42 | PD58 | HSQGTFFSDYSKYLDSRRAQDFVQWLLET-CONH₂ |
| 43 | PD59 | HSQGTFTSDYSKYLDSRRAQDFVQWLLDS-CONH₂ | wherein the L-Serine at position 2 is replaced with Val, Ile, Asp, Glu, Met, Trp, Asn, D-Ala, D-Ser, or α-aminoisobutyric acid (aib), the Tyrosine at position 10 is replaced with a Lysine residue conjugated to a fatty acid or fatty diacid via a linking moiety, wherein CONH₂ indicates the C-terminal amino acid carboxy group is amidated.

2. The co-agonist peptide of claim 1, wherein the fatty acid or fatty diacid comprises 14 to 20 methylene groups.

3. The co-agonist peptide of claim 1, wherein the fatty acid or fatty diacid comprises 16 carbon atoms.

4. The co-agonist peptide of claim 1, wherein the linking moiety comprises a PEG₂ (8-amino-3,6-dioxaoctanoic acid) Gamma-Glutamic acid (γGlu), a γGlu, a γGluγGlu, or a PEG₂PEG₂ γGlu.

5. A co-agonist peptide comprising a peptide selected from the following peptides

| SEQ ID NO: | Name | Sequence |
|---|---|---|
| 44 | TP534 | HsQGTFTSDK(γEγEC16)SKYLDNKRAQDFVQWLMQT-CONH₂ |
| 45 | TP535 | HsQGTFTSDK(γEγEC16)SKYLDSRRAHDFVQWLLNT-CONH₂ |
| 46 | TP536 | HsQGTFLSDK(γEγEC16)SKLLDSRRAQDFVQWLMQT-CONH₂ |
| 47 | TP552 | HsQGTFLSDYSKLLDSRAAQDFVQWLLQT-CONH₂ |
| 48 | TP559 | HsQGTFTSDK(γEγEC16)SKYLDARAAHDFVQWLLNT-CONH₂ |
| 49 | TP572 | HUQGTFTSDK(γEγEC16)SKYLDSRRAHDFVQWLLNTKγE-CONH₂ |
| 50 | TP573 | HUQGTFTSDK(γEγEC16)SKYLDARAAHDFVQWLLNTKγE-CONH₂ |
| 51 | TP574 | HUQGTFTSDK(γEγEC16)SKYLDNKRAQDFVQWLMQTKγE-CONH₂ | wherein U is aminoisobutyric acid, s is D-Ser, γE=γ-glutamic acid, and C16=—CO—(CH₂)₁₄—CH₃, and wherein CONH₂ indicates the C-terminal amino acid carboxy group is amidated.

6. A composition comprising one or more co-agonist peptides of claim 1 and a pharmaceutically acceptable carrier and/or pharmaceutically acceptable salt.

7. A method for treating a patient for a metabolic disease or disorder comprising administering the patient an effective amount of any one or more of the co-agonist peptides of claim 1 to treat the metabolic disease or disorder in the patient.

8. The method of claim 7, wherein the metabolic disease or disorder comprises diabetes, non-alcoholic fatty liver disease (NAFLD), non-alcoholic steatohepatitis (NASH), or obesity.

9. The method of claim 8, wherein the diabetes comprises Type I diabetes, Type II diabetes, or gestational diabetes.

10. The method of claim 7, wherein the patient has more than one metabolic disease or disorder.

11. The method of claim 10, wherein the metabolic disease or disorder comprises, diabetes and NASH, NAFLD, or obesity; obesity and NASH or NAFLD; diabetes, NASH, and obesity; diabetes, NAFLD, and obesity; or diabetes and obesity.

12. A method for treating a patient for a metabolic disease or disorder comprising administering the patient an effective amount of the composition of claim 6 to treat the metabolic disease or disorder in the patient.

13. The method of claim 12, wherein the metabolic disease or disorder comprises diabetes, non-alcoholic fatty liver disease (NAFLD), non-alcoholic steatohepatitis (NASH), or obesity.

14. The method of claim 12, wherein the patient has more than one metabolic disease or disorder.

15. The method of claim 14, wherein the metabolic disease or disorder comprises, diabetes and NASH, NAFLD, or obesity; obesity and NASH or NAFLD; diabetes, NASH, and obesity; diabetes, NAFLD, and obesity; or diabetes and obesity.

16. A method for treating a metabolic disease or disorder in a patient or individual comprising: administering to the patient or individual an effective amount of the composition of claim 6 and administering to the patient or individual an effective amount of a composition comprising an insulin or insulin analog to treat the metabolic disease or disorder in the patient or individual.

17. The method of claim 16, wherein the insulin analog comprises insulin detemir, insulin glargine, insulin levemir, insulin glulisine, insulin degludec, or insulin lispro.

18. The method of claim 17, wherein the metabolic disease or disorder comprises diabetes, non-alcoholic fatty liver disease (NAFLD), non-alcoholic steatohepatitis (NASH), or obesity.

19. The method of claim 18, wherein the diabetes comprises Type I diabetes, Type II diabetes, or gestational diabetes.

20. The method of claim 16, wherein the patient has more than one metabolic disease or disorder selected from diabetes and NASH, NAFLD, or obesity; obesity and NASH or NAFLD; diabetes, NASH, and obesity; diabetes, NAFLD, and obesity; or diabetes and obesity.

* * * * *